US011679066B2

(12) United States Patent
Song et al.

(10) Patent No.: US 11,679,066 B2
(45) Date of Patent: *Jun. 20, 2023

(54) DISSOLVABLE SOLID FIBROUS ARTICLES CONTAINING ANIONIC SURFACTANTS

(71) Applicant: The Procter & Gamble Company, Cincinnati, OH (US)

(72) Inventors: Brian Xiaoqing Song, Mason, OH (US); Jennifer Elaine Hilvert, Cincinnati, OH (US); Min Mao, Deerfield Township, OH (US); Dinah Achola Nyangiro, Mason, OH (US); Brandon Michael Taylor, Erlanger, KY (US); Mark William Hamersky, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/912,876

(22) Filed: Jun. 26, 2020

(65) Prior Publication Data

US 2020/0405587 A1 Dec. 31, 2020

Related U.S. Application Data

(60) Provisional application No. 62/928,415, filed on Oct. 31, 2019, provisional application No. 62/867,990, filed on Jun. 28, 2019.

(51) Int. Cl.
*A61K 8/02* (2006.01)
*A61K 8/73* (2006.01)
*A61K 8/41* (2006.01)
*A61K 8/81* (2006.01)

(52) U.S. Cl.
CPC ............ *A61K 8/027* (2013.01); *A61K 8/0216* (2013.01); *A61K 8/416* (2013.01); *A61K 8/731* (2013.01); *A61K 8/732* (2013.01); *A61K 8/8129* (2013.01); *A61K 2800/10* (2013.01); *A61K 2800/30* (2013.01); *A61K 2800/5426* (2013.01)

(58) Field of Classification Search
CPC .................................................. A61K 8/0216
See application file for complete search history.

(56) References Cited

U.S. PATENT DOCUMENTS

| 1,421,350 A | 6/1922 | Powell |
|---|---|---|
| 2,356,168 A | 8/1944 | Mabley |
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | Mannheimer |
| 2,613,185 A | 10/1952 | Marshall |
| 2,648,635 A | 8/1953 | Jacques et al. |
| 2,658,072 A | 11/1953 | Kosmin |
| 2,694,668 A | 11/1954 | Fricke |
| 2,809,971 A | 10/1957 | Jack et al. |
| 3,152,046 A | 10/1964 | Maria |
| 3,236,733 A | 2/1966 | Karsten et al. |
| 3,293,718 A | 12/1966 | Melvin |
| 3,321,425 A | 5/1967 | Kar-ludwig |
| 3,332,880 A | 7/1967 | Adriaan et al. |
| 3,426,440 A | 2/1969 | Shen et al. |
| 3,428,478 A | 2/1969 | Donaldson et al. |
| 3,452,382 A | 7/1969 | Kazdan |
| 3,463,308 A | 8/1969 | Deneke |
| 3,489,688 A | 1/1970 | Pospischil |
| 3,570,122 A | 3/1971 | Willimas |
| 3,589,007 A | 6/1971 | Walton |
| 3,653,383 A | 4/1972 | Wise |
| 3,695,989 A | 10/1972 | Albert |
| 3,753,196 A | 8/1973 | Kurtz et al. |
| 3,761,418 A | 9/1973 | Parran |
| 3,859,125 A | 1/1975 | Miller |
| 3,875,300 A | 4/1975 | Homm et al. |
| 3,904,543 A | 9/1975 | Knighten |
| 3,929,678 A | 12/1975 | Laughlin |
| 3,943,949 A | 3/1976 | Ashton et al. |
| 3,954,113 A | 5/1976 | Bohrer et al. |
| 3,967,921 A | 7/1976 | Haberli |
| 4,020,156 A | 4/1977 | Murray et al. |
| 4,024,078 A | 5/1977 | Gilbert et al. |
| 4,033,365 A | 7/1977 | Klepak et al. |
| 4,051,081 A | 9/1977 | Jabs et al. |
| 4,089,945 A | 5/1978 | Brinkman |

(Continued)

FOREIGN PATENT DOCUMENTS

| CA | 166297 | 5/2018 |
|---|---|---|
| CA | 169627 | 5/2018 |

(Continued)

OTHER PUBLICATIONS

CN109589279b, Google Patent Translation, downloaded in Mar. 2021 (Year: 2021).*
Michelle Villett, Why You Need a Sulfate-Free Shampoo, The Skincare Edit, updated date: Jan. 25, 2019, original publication date: Feb. 22, 2016 (Year: 2016).*
Mana Okasaka, Evaluation of anionic surfactants effects on the skin barrier function based on skin permeability, Pharmaceutical Development and Technology, 24:1,99-104, published online: Jan. 23, 2018 (Year: 2018).*
Dow, UCARE™ Polymer LR-400, Technical Data Sheet, downloaded in Mar. 2022 (Year: 2022).*

(Continued)

*Primary Examiner* — Mark V Stevens
*Assistant Examiner* — Alparslan Asan
(74) *Attorney, Agent, or Firm* — Alexandra S. Anoff

(57) ABSTRACT

A dissolvable fibrous solid shampoo article containing fibrous elements. The fibrous elements can contain a polymeric structurant, a surfactant, and optionally a cationic polymer. The fibrous article is substantially free of lamellar structures and can have a hand dissolution of less than 15 strokes.

19 Claims, 8 Drawing Sheets

(56) References Cited

U.S. PATENT DOCUMENTS

| | | |
|---|---|---|
| 4,149,551 A | 4/1979 | Benjamin et al. |
| 4,180,558 A | 12/1979 | Franklin |
| 4,185,125 A | 1/1980 | Kimura et al. |
| 4,196,190 A | 4/1980 | Gehman et al. |
| 4,197,865 A | 4/1980 | Jacquet et al. |
| 4,206,196 A | 6/1980 | Davis |
| 4,217,914 A | 8/1980 | Jacquet et al. |
| 4,272,511 A | 6/1981 | Papantoniou et al. |
| 4,286,016 A | 8/1981 | Dimond |
| 4,287,219 A | 9/1981 | Fabre |
| 4,315,965 A | 2/1982 | Mason |
| 4,323,525 A | 4/1982 | Bornat |
| 4,323,683 A | 4/1982 | Bolich, Jr. et al. |
| 4,340,583 A | 7/1982 | Wason |
| 4,342,813 A | 8/1982 | Erickson |
| 4,345,080 A | 8/1982 | Bolich, Jr. |
| 4,349,531 A | 9/1982 | Mlodozeniec |
| D266,829 S | 11/1982 | Yoshizawa et al. |
| 4,377,615 A | 3/1983 | Suzuki |
| 4,379,753 A | 4/1983 | Bolich, Jr. |
| 4,381,919 A | 5/1983 | Jacquet et al. |
| 4,415,617 A | 11/1983 | D Elia |
| 4,422,853 A | 12/1983 | Jacquet et al. |
| 4,448,699 A | 5/1984 | Barrat et al. |
| 4,470,982 A | 9/1984 | Winkler |
| 4,507,280 A | 3/1985 | Pohl et al. |
| 4,529,586 A | 7/1985 | De Marco et al. |
| 4,536,361 A | 8/1985 | Torobin |
| 4,565,647 A | 1/1986 | Llenado |
| D286,450 S | 10/1986 | Tovey |
| 4,635,351 A | 1/1987 | Koch et al. |
| 4,637,859 A | 1/1987 | Trokhan |
| 4,639,390 A | 1/1987 | Shoji |
| 4,663,158 A | 5/1987 | Wolfram et al. |
| 4,683,001 A | 7/1987 | Floyd |
| 4,710,374 A | 12/1987 | Grollier et al. |
| 4,723,362 A | 2/1988 | Boerger |
| 4,727,410 A | 2/1988 | Higgins, III |
| 4,822,613 A | 4/1989 | Rodero |
| 4,885,107 A | 12/1989 | Wetzel |
| 4,892,758 A | 1/1990 | Serbiak |
| 4,923,660 A | 5/1990 | Willenberg |
| 4,976,953 A | 12/1990 | Orr et al. |
| 4,990,280 A | 2/1991 | Thorengaard |
| 5,041,252 A | 8/1991 | Fujii |
| 5,055,384 A | 10/1991 | Kuehnert |
| 5,061,481 A | 10/1991 | Suzuki et al. |
| 5,062,889 A | 11/1991 | Hoehl |
| 5,062,994 A | 11/1991 | Imperatori |
| 5,094,853 A | 3/1992 | Hagarty |
| 5,098,636 A | 3/1992 | Balk |
| 5,100,657 A | 3/1992 | Ansher-jackson et al. |
| 5,100,658 A | 3/1992 | Bolich, Jr. et al. |
| 5,102,129 A | 4/1992 | Roberts |
| 5,104,646 A | 4/1992 | Bolich, Jr. |
| 5,106,609 A | 4/1992 | Bolich, Jr. |
| 5,110,678 A | 5/1992 | Narukawa |
| 5,120,888 A | 6/1992 | Nohr |
| 5,135,804 A | 8/1992 | Harpell |
| 5,158,810 A | 10/1992 | Oishi |
| 5,166,276 A | 11/1992 | Hayama et al. |
| D334,420 S | 3/1993 | Copeland et al. |
| 5,208,104 A | 5/1993 | Ueda |
| 5,220,033 A | 6/1993 | Kamei |
| 5,230,853 A | 7/1993 | Colegrove |
| 5,261,426 A | 11/1993 | Kellett |
| 5,280,079 A | 1/1994 | Allen |
| RE34,584 E | 4/1994 | Grote |
| 5,342,335 A | 8/1994 | Rhim |
| D351,345 S | 10/1994 | Geho |
| 5,362,532 A | 11/1994 | Famili |
| 5,364,627 A | 11/1994 | Song |
| 5,387,147 A | 2/1995 | Ohshima |
| 5,391,368 A | 2/1995 | Gerstein |
| D357,115 S | 4/1995 | Ashley et al. |
| 5,409,703 A | 4/1995 | Mcanalley |
| D358,025 S | 5/1995 | Martin et al. |
| 5,415,810 A | 5/1995 | Lee |
| 5,429,628 A | 7/1995 | Trinh et al. |
| 5,429,874 A | 7/1995 | Vanputte |
| 5,444,113 A | 8/1995 | Sinclair et al. |
| 5,455,114 A | 10/1995 | Ohmory |
| 5,457,895 A | 10/1995 | Thompson |
| 5,458,433 A | 10/1995 | Stastny |
| 5,470,424 A | 11/1995 | Isaac |
| 5,470,653 A | 11/1995 | Honeycutt |
| 5,476,597 A | 12/1995 | Sakata et al. |
| 5,486,418 A | 1/1996 | Ohmory |
| 5,501,238 A | 3/1996 | Borstel |
| 5,518,730 A | 5/1996 | Fuisz |
| 5,520,924 A | 5/1996 | Chapman |
| 5,533,638 A | 7/1996 | Reiker |
| 5,538,735 A | 7/1996 | Ahn |
| 5,580,481 A | 12/1996 | Sakata et al. |
| 5,582,786 A | 12/1996 | Brunskill et al. |
| 5,585,059 A | 12/1996 | Kobayashi |
| D378,180 S | 2/1997 | Hayes et al. |
| 5,651,987 A | 7/1997 | Fuisz |
| 5,660,845 A | 8/1997 | Trinh et al. |
| 5,672,576 A | 9/1997 | Behrens et al. |
| 5,673,576 A | 10/1997 | Chen et al. |
| 5,674,478 A | 10/1997 | Dodd |
| 5,691,015 A | 11/1997 | Tsukamoto |
| 5,705,183 A | 1/1998 | Phillips |
| 5,716,692 A | 2/1998 | Warner |
| 5,717,026 A | 2/1998 | Ikimine |
| 5,735,812 A | 4/1998 | Hardy |
| 5,750,122 A | 5/1998 | Evans |
| 5,780,047 A | 7/1998 | Kamiya et al. |
| 5,780,418 A | 7/1998 | Niinaka |
| D398,847 S | 9/1998 | Wyslotsky et al. |
| D399,260 S | 10/1998 | Thimote |
| 5,827,586 A | 10/1998 | Yamashita |
| 5,840,423 A | 11/1998 | Sano |
| 5,849,378 A | 12/1998 | Gask |
| 5,863,887 A | 1/1999 | Gillette |
| 5,879,493 A | 3/1999 | Johnson |
| D407,640 S | 4/1999 | Crasper et al. |
| D408,223 S | 4/1999 | Henry |
| 5,911,224 A | 6/1999 | Berger |
| 5,914,124 A | 6/1999 | Mahoney |
| 5,925,603 A | 7/1999 | D'Angelo |
| 5,942,179 A | 8/1999 | Tallentire |
| 5,955,419 A | 9/1999 | Barket, Jr. et al. |
| D416,103 S | 11/1999 | Hashmi |
| 5,976,454 A | 11/1999 | Sterzel et al. |
| D418,415 S | 1/2000 | Hayes et al. |
| D418,750 S | 1/2000 | Blin |
| 6,010,719 A | 1/2000 | Remon et al. |
| 6,028,016 A | 2/2000 | Yahiaoui et al. |
| 6,029,808 A | 2/2000 | Peck et al. |
| 6,034,043 A | 3/2000 | Fujiwara |
| 6,037,319 A | 3/2000 | Dickler |
| 6,066,396 A | 5/2000 | Inada |
| 6,080,346 A | 6/2000 | Jack |
| D427,902 S | 7/2000 | Hayes et al. |
| 6,106,849 A | 8/2000 | Malkan |
| 6,130,193 A | 10/2000 | Gillette |
| 6,175,054 B1 | 1/2001 | Jacques |
| 6,177,391 B1 | 1/2001 | Zafar |
| 6,197,238 B1 | 3/2001 | Wang |
| 6,200,949 B1 | 3/2001 | Reijmer et al. |
| 6,207,274 B1 | 3/2001 | Ferenc |
| D441,869 S | 5/2001 | Bloor et al. |
| D442,353 S | 5/2001 | Macias |
| D442,739 S | 5/2001 | Friesenhahn |
| D443,389 S | 6/2001 | Friesenhahn |
| 6,274,162 B1 | 8/2001 | Steffenino |
| D448,802 S | 10/2001 | Lariviere, Jr. et al. |
| D449,881 S | 10/2001 | Mock, Sr. |
| D450,378 S | 11/2001 | Minakuchi et al. |
| 6,319,510 B1 | 11/2001 | Yates |
| 6,365,142 B1 | 4/2002 | Tamura |
| 6,382,526 B1 | 5/2002 | Reneker et al. |

(56) References Cited

U.S. PATENT DOCUMENTS

| | | |
|---|---|---|
| 6,406,797 B1 | 6/2002 | Vanputte |
| 6,417,156 B1 | 7/2002 | Smith et al. |
| 6,420,625 B1 | 7/2002 | Jones |
| 6,426,091 B1 | 7/2002 | Okumura et al. |
| 6,440,926 B1 | 8/2002 | Spadoni et al. |
| D462,900 S | 9/2002 | Yamada et al. |
| 6,448,462 B2 | 9/2002 | Groitzsch |
| 6,458,754 B1 | 10/2002 | Velazquez et al. |
| 6,465,407 B2 | 10/2002 | Hayashi |
| D465,303 S | 11/2002 | Friesenhahn |
| 6,503,521 B1 | 1/2003 | Atis et al. |
| 6,525,034 B2 | 2/2003 | Dalrymple et al. |
| 6,552,123 B1 | 4/2003 | Katayama |
| 6,576,575 B2 | 6/2003 | Griesbach, III |
| 6,608,121 B2 | 8/2003 | Isozaki |
| D479,561 S | 9/2003 | Meyer |
| 6,623,694 B1 | 9/2003 | Ferguson et al. |
| 6,657,004 B2 | 12/2003 | Mizutani |
| D484,749 S | 1/2004 | Garraway |
| 6,699,826 B1 | 3/2004 | Saijo |
| 6,723,160 B2 | 4/2004 | Mackey et al. |
| D489,162 S | 5/2004 | Dings-plooij |
| 6,730,648 B2 | 5/2004 | Gorlin |
| 6,783,852 B2 | 8/2004 | Inada |
| 6,787,512 B1 | 9/2004 | Verrall |
| 6,790,814 B1 | 9/2004 | Marin |
| 6,800,295 B2 | 10/2004 | Fox |
| 6,802,295 B2 | 10/2004 | Bedwell et al. |
| 6,808,375 B2 | 10/2004 | Kloetzer |
| 6,808,598 B1 | 10/2004 | Takeuchi |
| 6,818,606 B1 | 11/2004 | Hanada |
| 6,825,161 B2 | 11/2004 | Shefer et al. |
| 6,831,046 B2 | 12/2004 | Carew et al. |
| 6,846,784 B2 | 1/2005 | Engel et al. |
| 6,878,368 B2 | 4/2005 | Ohta et al. |
| 6,898,819 B2 | 5/2005 | Tanaka et al. |
| 6,898,921 B2 | 5/2005 | Duffield |
| D509,935 S | 9/2005 | Burt |
| 6,943,200 B1 | 9/2005 | Corrand et al. |
| 6,949,498 B2 | 9/2005 | Murphy |
| 6,956,070 B2 | 10/2005 | Fujiwara |
| 6,977,116 B2 | 12/2005 | Cabell |
| D515,915 S | 2/2006 | Karim |
| 7,015,181 B2 | 3/2006 | Lambino |
| 7,026,049 B2 | 4/2006 | Endo |
| 7,041,369 B1 | 5/2006 | Mackey et al. |
| 7,067,575 B2 | 6/2006 | Kitamura |
| 7,083,047 B2 | 8/2006 | Bone |
| 7,094,744 B1 | 8/2006 | Kobayashi |
| 7,115,551 B2 | 10/2006 | Hasenoehrl |
| 7,125,828 B2 | 10/2006 | Catlin |
| 7,169,740 B2 | 1/2007 | Sommerville-roberts |
| 7,172,765 B2 | 2/2007 | Chu et al. |
| 7,196,026 B2 | 3/2007 | Di Luccio |
| RE39,557 E | 4/2007 | Moe |
| 7,208,460 B2 | 4/2007 | Shefer et al. |
| 7,226,899 B2 | 6/2007 | Cole |
| D549,051 S | 8/2007 | Nordwall |
| 7,285,520 B2 | 10/2007 | Krzysik |
| 7,291,300 B2 | 11/2007 | Chhabra et al. |
| 7,387,787 B2 | 6/2008 | Fox |
| 7,407,669 B2 | 8/2008 | Leung |
| D576,753 S | 9/2008 | Mukai |
| D577,332 S | 9/2008 | Moore |
| 7,429,273 B2 | 9/2008 | De Dominicis |
| D578,881 S | 10/2008 | Friedland et al. |
| 7,446,084 B2 | 11/2008 | Barthel |
| 7,491,407 B2 | 2/2009 | Pourdeyhimi |
| D588,332 S | 3/2009 | Phelan |
| 7,507,698 B2 | 3/2009 | Franzolin |
| 7,547,737 B2 | 6/2009 | Kochvar |
| 7,563,757 B2 | 7/2009 | Kouvroukoglou |
| 7,704,328 B2 | 4/2010 | Bailey et al. |
| 7,708,840 B2 | 5/2010 | Wiedemann |
| 7,727,946 B2 | 6/2010 | Catalfamo |
| 7,824,588 B2 | 11/2010 | Yang |
| 7,832,552 B2 | 11/2010 | Newman |
| 7,846,402 B2 | 12/2010 | Spadini et al. |
| 7,856,989 B2 | 12/2010 | Karles |
| 7,892,992 B2 | 2/2011 | Kamada et al. |
| 7,901,696 B2 | 3/2011 | Eknoian et al. |
| 7,967,801 B2 | 6/2011 | Hammons |
| D640,921 S | 7/2011 | Caldwell |
| D644,541 S | 9/2011 | Schrader et al. |
| D651,096 S | 12/2011 | Nakagiri |
| D655,154 S | 3/2012 | Amos |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr. |
| 8,288,332 B2 | 10/2012 | Fossum et al. |
| 8,309,505 B2 | 11/2012 | Fossum et al. |
| 8,349,232 B2 | 1/2013 | Pourdeyhimi |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,357,728 B2 | 1/2013 | Butter et al. |
| 8,367,596 B2 | 2/2013 | Fossum et al. |
| D680,882 S | 4/2013 | Logue |
| 8,415,287 B2 | 4/2013 | Glenn, Jr. et al. |
| D682,622 S | 5/2013 | Keys |
| 8,461,090 B2 | 6/2013 | Glenn, Jr. et al. |
| 8,461,091 B2 | 6/2013 | Glenn, Jr. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,541,081 B1 | 9/2013 | Ranganathan et al. |
| 8,546,640 B2 | 10/2013 | Popovsky et al. |
| D694,621 S | 12/2013 | Mccarthy |
| 8,723,333 B2 | 5/2014 | Park et al. |
| 8,765,170 B2 | 7/2014 | Glenn, Jr. |
| 8,785,361 B2 | 7/2014 | Sivik et al. |
| D712,159 S | 9/2014 | Clerici et al. |
| D712,822 S | 9/2014 | Brusaw et al. |
| 9,062,186 B2 | 6/2015 | Longdon et al. |
| 9,074,305 B2 | 7/2015 | Glenn, Jr. et al. |
| D739,227 S | 9/2015 | Mitchell |
| 9,139,802 B2 | 9/2015 | Weisman et al. |
| D740,928 S | 10/2015 | Bruining |
| 9,163,205 B2 | 10/2015 | Sivik et al. |
| 9,175,250 B2 | 11/2015 | Sivik et al. |
| 9,198,838 B2 | 12/2015 | Glenn, Jr. |
| D748,240 S | 1/2016 | Goode |
| 9,421,153 B2 | 8/2016 | Sivik et al. |
| D769,522 S | 10/2016 | Venet |
| D771,788 S | 11/2016 | Duckwitz |
| 9,480,628 B2 | 11/2016 | Sivik et al. |
| D774,086 S | 12/2016 | Montes et al. |
| D775,198 S | 12/2016 | Montes et al. |
| 9,539,444 B2 | 1/2017 | Kinoshita et al. |
| 9,545,364 B2 | 1/2017 | Glenn, Jr. et al. |
| D778,026 S | 2/2017 | Roetheli |
| D793,025 S | 8/2017 | Slusarczyk et al. |
| D797,551 S | 9/2017 | Chatterton et al. |
| D798,143 S | 9/2017 | Chatterton |
| D808,583 S | 1/2018 | Zietek |
| D811,922 S | 3/2018 | Lefave |
| D811,935 S | 3/2018 | Hughes |
| D819,836 S | 6/2018 | Noël |
| 10,045,915 B2 | 8/2018 | Glenn, Jr. et al. |
| D848,102 S | 5/2019 | Carlson et al. |
| D850,041 S | 5/2019 | Endle |
| 10,294,586 B2 * | 5/2019 | Sivik .................. D01F 6/66 |
| D851,344 S | 6/2019 | Carlson et al. |
| D857,156 S | 8/2019 | Hani |
| D857,242 S | 8/2019 | Darrow et al. |
| D857,929 S | 8/2019 | Darrow et al. |
| D862,020 S | 10/2019 | Gorrell et al. |
| D863,600 S | 10/2019 | Chao |
| D864,507 S | 10/2019 | Stoughton |
| D866,105 S | 11/2019 | Carlson et al. |
| D866,891 S | 11/2019 | Carlson et al. |
| D866,892 S | 11/2019 | Hunt et al. |
| D866,893 S | 11/2019 | Hunt et al. |
| D867,717 S | 11/2019 | Chavez |

(56) References Cited

U.S. PATENT DOCUMENTS

| | | |
|---|---|---|
| D868,159 S | 11/2019 | Swisher et al. |
| D868,953 S | 12/2019 | Mckendree |
| 10,569,286 B2 | 2/2020 | Anderson et al. |
| D878,694 S | 3/2020 | Carlson et al. |
| 10,646,413 B2 | 5/2020 | Sivik et al. |
| 10,694,917 B2 | 6/2020 | Dreher et al. |
| D901,115 S | 11/2020 | Carlson et al. |
| D903,152 S | 11/2020 | Chao |
| 10,821,056 B2 | 11/2020 | Swartz et al. |
| D906,802 S | 1/2021 | Chi |
| 10,894,005 B2 | 1/2021 | Sivik et al. |
| D910,434 S | 2/2021 | Tan |
| D910,457 S | 2/2021 | Lee |
| D921,166 S | 6/2021 | Meyers |
| D933,095 S | 10/2021 | Heiner et al. |
| 2001/0037851 A1 | 11/2001 | Mortellite |
| 2002/0177621 A1 | 1/2002 | Hanada et al. |
| 2002/0018906 A1 | 2/2002 | Clark |
| 2002/0044968 A1 | 4/2002 | Van Lengerich |
| 2002/0064510 A1 | 5/2002 | Dalrymple et al. |
| 2002/0077264 A1 | 6/2002 | Roberts et al. |
| 2002/0081732 A1 | 6/2002 | Bowlin et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0161088 A1 | 10/2002 | Kochvar |
| 2002/0169092 A1 | 11/2002 | Alexandre et al. |
| 2002/0173213 A1 | 11/2002 | Chu |
| 2002/0175449 A1 | 11/2002 | Chu et al. |
| 2002/0176827 A1 | 11/2002 | Rajaiah |
| 2002/0187181 A1 | 12/2002 | Godbey et al. |
| 2003/0013369 A1 | 1/2003 | Soane et al. |
| 2003/0017208 A1 | 1/2003 | Ignatious |
| 2003/0018242 A1 | 1/2003 | Harsh et al. |
| 2003/0032573 A1 | 2/2003 | Tanner |
| 2003/0045441 A1 | 3/2003 | Hsu et al. |
| 2003/0045446 A1 | 3/2003 | Dihora |
| 2003/0069154 A1 | 4/2003 | Hsu et al. |
| 2003/0080150 A1 | 5/2003 | Cowan et al. |
| 2003/0099691 A1 | 5/2003 | Lydzinski et al. |
| 2003/0099692 A1 | 5/2003 | Lydzinski et al. |
| 2003/0114332 A1 | 6/2003 | Ramcharan et al. |
| 2003/0141662 A1 | 7/2003 | Kost |
| 2003/0166489 A1 | 9/2003 | Van Asten et al. |
| 2003/0166495 A1 | 9/2003 | Wang |
| 2003/0180242 A1 | 9/2003 | Eccard et al. |
| 2003/0185872 A1 | 10/2003 | Kochinke |
| 2003/0186826 A1 | 10/2003 | Eccard et al. |
| 2003/0194416 A1 | 10/2003 | Shefer |
| 2003/0199412 A1 | 10/2003 | Gupta |
| 2003/0207776 A1 | 11/2003 | Shefer et al. |
| 2003/0209166 A1 | 11/2003 | Vanmaele et al. |
| 2003/0215522 A1 | 11/2003 | Johnson et al. |
| 2003/0216098 A1 | 11/2003 | Carlyle |
| 2003/0224959 A1 | 12/2003 | Smith |
| 2003/0232183 A1 | 12/2003 | Dutton |
| 2004/0029762 A1 | 2/2004 | Hensley |
| 2004/0032859 A1 | 2/2004 | Miao |
| 2004/0048759 A1 | 3/2004 | Ribble et al. |
| 2004/0048771 A1 | 3/2004 | Mcdermott et al. |
| 2004/0053808 A1 | 3/2004 | Raehse et al. |
| 2004/0059055 A1 | 3/2004 | Inada et al. |
| 2004/0071742 A1 | 4/2004 | Popplewell |
| 2004/0071755 A1 | 4/2004 | Fox |
| 2004/0082239 A1 | 4/2004 | Di Luccio et al. |
| 2004/0092635 A1 | 5/2004 | Kitamura |
| 2004/0108615 A1 | 6/2004 | Foley |
| 2004/0110656 A1 | 6/2004 | Casey et al. |
| 2004/0118852 A1 | 6/2004 | Barmore et al. |
| 2004/0126585 A1 | 7/2004 | Kerins et al. |
| 2004/0167256 A1 | 8/2004 | Verrall |
| 2004/0170836 A1 | 9/2004 | Bond |
| 2004/0175404 A1 | 9/2004 | Shefer |
| 2004/0180597 A1 | 9/2004 | Kamada |
| 2004/0202632 A1 | 10/2004 | Gott et al. |
| 2004/0204543 A1 | 10/2004 | Yang |
| 2004/0206270 A1 | 10/2004 | Vanmaele et al. |
| 2004/0242097 A1 | 12/2004 | Hasenoehri |
| 2004/0242772 A1 | 12/2004 | Huth et al. |
| 2004/0253434 A1 | 12/2004 | Patel |
| 2004/0254086 A1 | 12/2004 | Hedges et al. |
| 2005/0003048 A1 | 1/2005 | Pearce |
| 2005/0003991 A1 | 1/2005 | Macquarrie |
| 2005/0008776 A1 | 1/2005 | Chhabra |
| 2005/0010010 A1 | 1/2005 | Kitamura |
| 2005/0069575 A1 | 3/2005 | Fox |
| 2005/0118237 A1 | 6/2005 | Krzysik et al. |
| 2005/0136112 A1 | 6/2005 | Gonzales |
| 2005/0136772 A1 | 6/2005 | Chen et al. |
| 2005/0136780 A1 | 6/2005 | Clark et al. |
| 2005/0137115 A1 | 6/2005 | Cole et al. |
| 2005/0137272 A1 | 6/2005 | Gaserod |
| 2005/0159730 A1 | 7/2005 | Kathrani et al. |
| 2005/0180962 A1 | 8/2005 | Raz et al. |
| 2005/0186256 A1 | 8/2005 | Dihel |
| 2005/0202992 A1 | 9/2005 | Grandio Portabales et al. |
| 2005/0209574 A1 | 9/2005 | Boehringer |
| 2005/0220745 A1 | 10/2005 | Lu |
| 2005/0232954 A1 | 10/2005 | Yoshinari et al. |
| 2005/0253297 A1 | 11/2005 | Pedmo et al. |
| 2005/0267005 A1 | 12/2005 | Dasque et al. |
| 2005/0272836 A1 | 12/2005 | Yaginuma et al. |
| 2005/0281757 A1 | 12/2005 | Ibrahim |
| 2005/0287106 A1 | 12/2005 | Legendre |
| 2006/0002880 A1 | 1/2006 | Peffly et al. |
| 2006/0013869 A1 | 1/2006 | Ignatious |
| 2006/0035042 A1 | 2/2006 | Morken |
| 2006/0052263 A1 | 3/2006 | Roreger |
| 2006/0064510 A1 | 3/2006 | Low et al. |
| 2006/0078528 A1 | 4/2006 | Yang et al. |
| 2006/0078529 A1 | 4/2006 | Uchida et al. |
| 2006/0083784 A1 | 4/2006 | Ignatious |
| 2006/0089276 A1 | 4/2006 | Klotz |
| 2006/0127458 A1 | 6/2006 | Kiser |
| 2006/0128592 A1 | 6/2006 | Ross et al. |
| 2006/0134412 A1 | 6/2006 | Mackey |
| 2006/0135026 A1 | 6/2006 | Arendt et al. |
| 2006/0159730 A1 | 7/2006 | Simon |
| 2006/0160453 A1 | 7/2006 | Suh |
| 2006/0189772 A1 | 8/2006 | Scheibel |
| 2006/0228319 A1 | 10/2006 | Vona, Jr. et al. |
| 2006/0254013 A1 | 11/2006 | Konishi |
| 2006/0254014 A1 | 11/2006 | Konishi |
| 2006/0258251 A1 | 11/2006 | Konishi |
| 2006/0264130 A1 | 11/2006 | Karles |
| 2006/0274263 A1 | 12/2006 | Yacktman et al. |
| 2007/0028939 A1 | 2/2007 | Mareri et al. |
| 2007/0054579 A1 | 3/2007 | Baker, Jr. |
| 2007/0098749 A1 | 5/2007 | Eknoian et al. |
| 2007/0099813 A1 | 5/2007 | Luizzi et al. |
| 2007/0110792 A9 | 5/2007 | Simon |
| 2007/0128256 A1 | 6/2007 | Aubrun-sonneville |
| 2007/0134304 A1 | 6/2007 | Aubrun-sonneville |
| 2007/0134481 A1 | 6/2007 | Aubrun-sonneville |
| 2007/0135528 A1 | 6/2007 | Butler et al. |
| 2007/0149435 A1 | 6/2007 | Koenig et al. |
| 2007/0225388 A1 | 9/2007 | Cooper et al. |
| 2007/0253926 A1 | 11/2007 | Tadrowski |
| 2007/0259170 A1 | 11/2007 | Brown |
| 2007/0259996 A1 | 11/2007 | Vicari |
| 2007/0298064 A1 | 12/2007 | Koslow |
| 2008/0008906 A1 | 1/2008 | Catalfamo |
| 2008/0019935 A1 | 1/2008 | Khan |
| 2008/0035174 A1 | 2/2008 | Aubrun-sonneville et al. |
| 2008/0083420 A1 | 4/2008 | Glenn et al. |
| 2008/0087293 A1 | 4/2008 | Glenn et al. |
| 2008/0090939 A1 | 4/2008 | Netravali et al. |
| 2008/0095828 A1 | 4/2008 | Privitera et al. |
| 2008/0108748 A1 | 5/2008 | Buckley |
| 2008/0118727 A1 | 5/2008 | Andersen |
| 2008/0131695 A1 | 6/2008 | Aouad et al. |
| 2008/0138492 A1 | 6/2008 | Cingotti |
| 2008/0146481 A1 | 6/2008 | Brown |
| 2008/0149119 A1 | 6/2008 | Shen |

(56) References Cited

U.S. PATENT DOCUMENTS

| | | |
|---|---|---|
| 2008/0152894 A1 | 6/2008 | Beihoffer et al. |
| 2008/0153730 A1 | 6/2008 | Tsaur |
| 2008/0215023 A1 | 9/2008 | Scavone et al. |
| 2008/0220054 A1 | 9/2008 | Shastri |
| 2008/0226919 A1 | 9/2008 | Hosoda |
| 2008/0242572 A1 | 10/2008 | Icht |
| 2008/0269095 A1 | 10/2008 | Aubrun-sonneville |
| 2008/0276178 A1 | 11/2008 | Fadell |
| 2008/0292669 A1 | 11/2008 | Deng et al. |
| 2008/0293839 A1 | 11/2008 | Stobby |
| 2009/0004254 A1 | 1/2009 | Maibach |
| 2009/0041820 A1 | 2/2009 | Wu et al. |
| 2009/0061225 A1 | 3/2009 | Bailey et al. |
| 2009/0061496 A1 | 3/2009 | Kuhn |
| 2009/0061719 A1 | 3/2009 | Shibutani |
| 2009/0155326 A1 | 6/2009 | Mack |
| 2009/0155383 A1 | 6/2009 | Kitko et al. |
| 2009/0181587 A1 | 7/2009 | Kang |
| 2009/0197787 A1 | 8/2009 | Venet et al. |
| 2009/0232873 A1 | 9/2009 | Glenn, Jr. et al. |
| 2009/0247036 A1 | 10/2009 | Shi et al. |
| 2009/0249558 A1 | 10/2009 | Fileccia |
| 2009/0258099 A1 | 10/2009 | Brown et al. |
| 2009/0263342 A1 | 10/2009 | Glenn, Jr. |
| 2009/0285718 A1 | 11/2009 | Privitera |
| 2009/0286437 A1 | 11/2009 | Cunningham et al. |
| 2009/0291282 A1 | 11/2009 | Kitamura et al. |
| 2009/0312220 A1 | 12/2009 | Boutoille |
| 2010/0018641 A1 | 1/2010 | Branham |
| 2010/0021517 A1 | 1/2010 | Ahlers |
| 2010/0098745 A1 | 4/2010 | Staab |
| 2010/0105821 A1 | 4/2010 | Verrall |
| 2010/0135921 A1 | 6/2010 | Hughes et al. |
| 2010/0150976 A1 | 6/2010 | Schnitzler |
| 2010/0166854 A1 | 7/2010 | Michniak-kohn |
| 2010/0167971 A1 | 7/2010 | Glenn, Jr. et al. |
| 2010/0173817 A1 | 7/2010 | Glenn, Jr. et al. |
| 2010/0179083 A1 | 7/2010 | Glenn, Jr. et al. |
| 2010/0196440 A1 | 8/2010 | Stark |
| 2010/0266668 A1 | 10/2010 | Coffee |
| 2010/0279905 A1 | 11/2010 | Glenn, Jr. |
| 2010/0285101 A1 | 11/2010 | Moore |
| 2010/0286011 A1 | 11/2010 | Glenn, Jr. et al. |
| 2010/0291165 A1 | 11/2010 | Glenn, Jr. et al. |
| 2010/0298188 A1 | 11/2010 | Glenn, Jr. et al. |
| 2011/0014252 A1 | 1/2011 | Sagel et al. |
| 2011/0023240 A1 | 2/2011 | Fossum |
| 2011/0027328 A1 | 2/2011 | Baig et al. |
| 2011/0028373 A1 | 2/2011 | Fossum et al. |
| 2011/0028374 A1 | 2/2011 | Fossum et al. |
| 2011/0033509 A1 | 2/2011 | Simon |
| 2011/0129510 A1 | 6/2011 | Liebmann |
| 2011/0136719 A1 | 6/2011 | Jalbert |
| 2011/0159267 A1 | 6/2011 | Lee |
| 2011/0165110 A1 | 7/2011 | Kinoshita et al. |
| 2011/0182956 A1 | 7/2011 | Glenn, Jr. et al. |
| 2011/0189246 A1 | 8/2011 | Glenn, Jr. et al. |
| 2011/0189247 A1 | 8/2011 | Glenn, Jr. |
| 2011/0195098 A1* | 8/2011 | Glenn, Jr ............ A61K 8/02 424/401 |
| 2011/0223381 A1 | 9/2011 | Sauter |
| 2011/0230112 A1 | 9/2011 | Rose |
| 2011/0250256 A1 | 10/2011 | Hyun-oh et al. |
| 2011/0287687 A1 | 11/2011 | Kramer et al. |
| 2011/0301070 A1 | 12/2011 | Ochomogo |
| 2012/0021026 A1 | 1/2012 | Glenn, Jr. |
| 2012/0027838 A1 | 2/2012 | Gordon et al. |
| 2012/0048769 A1 | 3/2012 | Sivik |
| 2012/0052036 A1 | 3/2012 | Glenn, Jr. |
| 2012/0052037 A1 | 3/2012 | Sivik et al. |
| 2012/0053103 A1 | 3/2012 | Sivik |
| 2012/0053108 A1 | 3/2012 | Glenn, Jr. |
| 2012/0058100 A1 | 3/2012 | Shastri et al. |
| 2012/0058166 A1 | 3/2012 | Glenn, Jr. |
| 2012/0082037 A1 | 4/2012 | Wang |
| 2012/0107534 A1 | 5/2012 | Wnuk et al. |
| 2012/0172831 A1 | 7/2012 | Darcy |
| 2012/0215148 A1 | 8/2012 | Ewert |
| 2012/0237576 A1 | 9/2012 | Gordon |
| 2012/0258902 A1 | 10/2012 | Parrish et al. |
| 2012/0270029 A1 | 10/2012 | Glenn, Jr. et al. |
| 2012/0288693 A1 | 11/2012 | Stanley et al. |
| 2012/0294823 A1 | 11/2012 | Aramwit |
| 2012/0321580 A1 | 12/2012 | Glenn, Jr. |
| 2013/0236520 A1 | 9/2013 | Popovsky et al. |
| 2013/0303419 A1 | 11/2013 | Glenn, Jr. et al. |
| 2014/0105946 A1 | 4/2014 | Glenn, Jr. et al. |
| 2014/0127145 A1 | 5/2014 | Deckner |
| 2014/0287973 A1 | 9/2014 | Sivik |
| 2014/0329428 A1 | 11/2014 | Glenn, Jr. |
| 2015/0044157 A1 | 2/2015 | Kulkarni et al. |
| 2015/0102307 A1 | 4/2015 | Tajima et al. |
| 2015/0297494 A1* | 10/2015 | Mao .................. A61K 8/81 |
| 2015/0313803 A1 | 11/2015 | Lynch et al. |
| 2015/0313804 A1 | 11/2015 | Lynch et al. |
| 2015/0313805 A1 | 11/2015 | Lynch et al. |
| 2015/0313806 A1 | 11/2015 | Lynch et al. |
| 2015/0313807 A1 | 11/2015 | Lynch et al. |
| 2015/0313808 A1 | 11/2015 | Lynch et al. |
| 2015/0313809 A1 | 11/2015 | Lynch et al. |
| 2015/0315350 A1 | 11/2015 | Mao et al. |
| 2016/0008235 A1 | 1/2016 | Sivik et al. |
| 2016/0010041 A1 | 1/2016 | Sivik et al. |
| 2016/0101026 A1 | 4/2016 | Pratt |
| 2016/0101204 A1 | 4/2016 | Lynch et al. |
| 2016/0143827 A1 | 5/2016 | Castan Barberan et al. |
| 2016/0250109 A1 | 9/2016 | Dreher et al. |
| 2016/0324741 A1 | 11/2016 | Baig |
| 2016/0367104 A1 | 12/2016 | Dreher et al. |
| 2017/0121641 A1 | 5/2017 | Smith |
| 2017/0335080 A1 | 11/2017 | Mao et al. |
| 2018/0015643 A1 | 1/2018 | Patel et al. |
| 2018/0110710 A1 | 4/2018 | Zhao et al. |
| 2018/0140469 A1 | 5/2018 | Kane et al. |
| 2018/0163325 A1 | 6/2018 | Glenn, Jr. et al. |
| 2018/0258555 A1 | 9/2018 | Glenn, Jr. |
| 2018/0311135 A1* | 11/2018 | Chang ................ A61K 8/81 |
| 2018/0333339 A1 | 11/2018 | Hamersky |
| 2018/0334644 A1* | 11/2018 | Hamersky ............ C11D 17/04 |
| 2018/0338890 A1 | 11/2018 | Glenn, Jr. |
| 2019/0015875 A1 | 1/2019 | Gardner, Jr. et al. |
| 2019/0282457 A1 | 9/2019 | Pratt |
| 2019/0282461 A1 | 9/2019 | Glassmeyer |
| 2019/0350819 A1 | 11/2019 | Hamersky et al. |
| 2020/0071851 A1 | 3/2020 | Glenn, Jr. et al. |
| 2020/0093710 A1 | 3/2020 | Hamersky |
| 2020/0214946 A1 | 7/2020 | Chan |
| 2020/0261326 A1 | 8/2020 | Sivik et al. |
| 2020/0275818 A1 | 9/2020 | Dreher et al. |
| 2020/0308360 A1 | 10/2020 | Mao |
| 2021/0000733 A1 | 1/2021 | Hilvert et al. |
| 2021/0094744 A1 | 4/2021 | Benson et al. |
| 2021/0107263 A1 | 4/2021 | Bartolucci et al. |
| 2021/0128417 A1 | 5/2021 | Sivik et al. |
| 2021/0137798 A1 | 5/2021 | Sivik et al. |
| 2021/0147763 A1 | 5/2021 | Tan et al. |
| 2021/0189602 A1 | 6/2021 | Glenn, Jr. et al. |
| 2021/0401677 A1 | 12/2021 | Song |
| 2022/0257476 A1 | 8/2022 | Hamersky et al. |
| 2022/0323309 A1 | 10/2022 | Pratt et al. |

FOREIGN PATENT DOCUMENTS

| | | |
|---|---|---|
| CN | 1138091 | 12/1996 |
| CN | 1219388 | 6/1999 |
| CN | 1288558 | 10/2000 |
| CN | 1357613 A | 7/2002 |
| CN | 1454231 A | 11/2003 |
| CN | 1473194 A | 2/2004 |
| CN | 1530431 A | 9/2004 |
| CN | 1583991 A | 2/2005 |
| CN | 1726074 A | 1/2006 |
| CN | 3648760 | 5/2007 |
| CN | 301666535 | 9/2011 |

(56) References Cited

FOREIGN PATENT DOCUMENTS

| | | | |
|---|---|---|---|
| CN | 103735428 | | 4/2014 |
| CN | 304115833 | | 4/2017 |
| CN | 106726834 | A | 5/2017 |
| CN | 106728834 | A | 5/2017 |
| CN | 304537587 | | 3/2018 |
| CN | 109589279 | B * | 4/2019 ........... A61K 8/0216 |
| DE | 19607851 | A1 | 9/1997 |
| DE | 10331787 | A1 | 2/2005 |
| DE | 100932 | | 4/2018 |
| DE | 100938 | | 4/2018 |
| DE | 101063 | | 5/2018 |
| DE | 101100 | | 5/2018 |
| DE | 101101 | | 5/2018 |
| EP | 0392608 | A2 | 10/1990 |
| EP | 609808 | A1 | 8/1994 |
| EP | 0858828 | A1 | 8/1998 |
| EP | 0948960 | A2 | 10/1999 |
| EP | 1214879 | A2 | 6/2002 |
| EP | 1217987 | B1 | 12/2004 |
| EP | 1574561 | A1 | 9/2005 |
| EP | 1160311 | B1 | 3/2006 |
| EP | 1958532 | A2 | 8/2008 |
| EP | 2085434 | A1 | 8/2009 |
| EP | 1317916 | B1 | 10/2010 |
| FR | 2871685 | A1 | 12/2005 |
| FR | 2886845 | A1 | 12/2006 |
| GB | 2235204 | A | 2/1991 |
| GB | 2355008 | A | 4/2001 |
| GB | 2378407 | A | 2/2003 |
| JP | S4912158 | A | 2/1974 |
| JP | 58021608 | | 2/1983 |
| JP | S58216109 | A | 12/1983 |
| JP | S59163458 | A | 9/1984 |
| JP | S6272609 | A | 4/1987 |
| JP | S6272610 | A | 4/1987 |
| JP | S6281432 | A | 4/1987 |
| JP | S6281462 | A | 4/1987 |
| JP | 62156348 | | 7/1987 |
| JP | H01172319 | A | 12/1987 |
| JP | S6346251 | A | 2/1988 |
| JP | S63156715 | A | 6/1988 |
| JP | H01313418 | A | 12/1989 |
| JP | H0243268 | A | 2/1990 |
| JP | 0275650 | A | 3/1990 |
| JP | H02280771 | A | 11/1990 |
| JP | 3040879 | A | 2/1991 |
| JP | 3101618 | A | 4/1991 |
| JP | H05344873 | A | 12/1993 |
| JP | H0617083 | A | 1/1994 |
| JP | H06116568 | A | 4/1994 |
| JP | 0753349 | A | 2/1995 |
| JP | H0789852 | A | 4/1995 |
| JP | H08325133 | A | 12/1996 |
| JP | H09216809 | A | 8/1997 |
| JP | H09216909 | A | 8/1997 |
| JP | 09279457 | | 10/1997 |
| JP | H101824 | A | 1/1998 |
| JP | 10158700 | A | 6/1998 |
| JP | H10251371 | A | 9/1998 |
| JP | H10512929 | A | 12/1998 |
| JP | H11505569 | A | 5/1999 |
| JP | H11513053 | A | 11/1999 |
| JP | 2000053998 | A | 2/2000 |
| JP | 2000169896 | A | 6/2000 |
| JP | 2000229841 | A | 8/2000 |
| JP | 2001519376 | A | 10/2001 |
| JP | 2001520983 | A | 11/2001 |
| JP | 2002201531 | A | 7/2002 |
| JP | 2002226895 | A | 8/2002 |
| JP | 2003073700 | A | 3/2003 |
| JP | 2003082397 | A | 3/2003 |
| JP | 2003532554 | A | 11/2003 |
| JP | 2004509198 | A | 3/2004 |
| JP | 2004256799 | A | 9/2004 |
| JP | 2004533551 | A | 11/2004 |
| JP | 2004345983 | A | 12/2004 |
| JP | 2005171063 | A | 6/2005 |
| JP | 2005534716 | A | 11/2005 |
| JP | 2005538202 | A | 12/2005 |
| JP | 2006056835 | A | 3/2006 |
| JP | 2006511732 | A | 4/2006 |
| JP | 3828217 | B2 | 7/2006 |
| JP | 2006249029 | A | 9/2006 |
| JP | 2007001889 | A | 1/2007 |
| JP | 2007091954 | A | 4/2007 |
| JP | 2007197365 | A | 8/2007 |
| JP | 2007197540 | A | 8/2007 |
| JP | 2007528748 | A | 10/2007 |
| JP | 2007533763 | A | 11/2007 |
| JP | 2008156807 | A | 7/2008 |
| JP | 2008525436 | A | 7/2008 |
| JP | 2009079329 | A | 4/2009 |
| JP | 2009533569 | A | 9/2009 |
| JP | 2013505375 | A | 2/2013 |
| JP | 5344873 | B2 | 8/2013 |
| JP | 2013531145 | A | 8/2013 |
| JP | 2013531748 | A | 8/2013 |
| JP | 2015509147 | A | 3/2015 |
| JP | 5821609 | B2 | 10/2015 |
| JP | 6272610 | B2 | 1/2018 |
| KR | 20020003442 | A | 1/2002 |
| KR | 20040094520 | A | 11/2004 |
| RU | 19735 | U1 | 10/2001 |
| RU | 2192451 | C2 | 11/2002 |
| RU | 2300196 | C2 | 6/2007 |
| RU | 2347557 | C2 | 2/2009 |
| TW | 232027 | B | 10/1994 |
| WO | 8301943 | A1 | 6/1983 |
| WO | 1992006603 | A1 | 4/1992 |
| WO | 1994002377 | A1 | 2/1994 |
| WO | 9404656 | A2 | 3/1994 |
| WO | 9514495 | A1 | 6/1995 |
| WO | 9523888 | A1 | 9/1995 |
| WO | 9951715 | A1 | 10/1999 |
| WO | 9957155 | A1 | 11/1999 |
| WO | 2000013680 | A2 | 3/2000 |
| WO | 0042992 | A2 | 7/2000 |
| WO | 0107194 | A1 | 2/2001 |
| WO | 0110421 | A1 | 2/2001 |
| WO | 0119948 | A1 | 3/2001 |
| WO | 0125322 | A1 | 4/2001 |
| WO | 0125393 | A1 | 4/2001 |
| WO | 200125322 | A1 | 4/2001 |
| WO | 2001024770 | A1 | 4/2001 |
| WO | 200154667 | A1 | 8/2001 |
| WO | 2001054667 | A1 | 8/2001 |
| WO | 0238722 | A2 | 5/2002 |
| WO | 03044153 | A1 | 5/2003 |
| WO | 03060007 | A1 | 7/2003 |
| WO | 2004009335 | A1 | 1/2004 |
| WO | 2004032859 | A1 | 4/2004 |
| WO | 2004041991 | A1 | 5/2004 |
| WO | 2004081162 | A1 | 9/2004 |
| WO | 2005003423 | A1 | 1/2005 |
| WO | 2005068604 | A1 | 7/2005 |
| WO | 2005070374 | A1 | 8/2005 |
| WO | 2005075547 | A1 | 8/2005 |
| WO | 2006106514 | A2 | 10/2006 |
| WO | 2006130647 | A1 | 12/2006 |
| WO | 2007022229 | A1 | 2/2007 |
| WO | 2007033598 | A1 | 3/2007 |
| WO | 2007089259 | A1 | 8/2007 |
| WO | 2007093558 | A1 | 8/2007 |
| WO | 2007093619 | A1 | 8/2007 |
| WO | 2007102119 | A1 | 9/2007 |
| WO | 2008049242 | A1 | 5/2008 |
| WO | 2008104954 | A1 | 9/2008 |
| WO | 2008149248 | A2 | 12/2008 |
| WO | 2009019571 | A2 | 2/2009 |
| WO | 2009022761 | A1 | 2/2009 |
| WO | 2007014221 | A3 | 4/2009 |
| WO | 2009095891 | A1 | 8/2009 |
| WO | 2009103576 | A1 | 8/2009 |
| WO | 2009121900 | A1 | 10/2009 |

(56) References Cited

FOREIGN PATENT DOCUMENTS

| | | |
|---|---|---|
| WO | 2010006708 A1 | 1/2010 |
| WO | 2010015709 A2 | 2/2010 |
| WO | 2010077627 A2 | 7/2010 |
| WO | 2010085569 A1 | 7/2010 |
| WO | 2011153023 A1 | 12/2011 |
| WO | 2012120199 A1 | 9/2012 |
| WO | 2019001940 A1 | 1/2019 |

OTHER PUBLICATIONS

Karen Duis et al., Environmental fate and effects of water-soluble synthetic organic polymers used in cosmetic products, Environmental Sciences Europe vol. 33, Article No. 21, 2021, Supplementary Information (Year: 2021).*
Sesame Shop, Low pH shampoo?!—Pyunkang Yul Shampoo Review, publication date: Sep. 23, 2018 (Year: 2018).*
U.S. Appl. No. 16/589,504, filed Oct. 1, 2019, Benson et al.
U.S. Appl. No. 15/981,096, filed May 16, 2018, Hamersky et al.
U.S. Appl. No. 16/918,292, filed Jul. 1, 2020, Hilvert et al.
U.S. Appl. No. 29/672,822, filed Dec. 10, 2018, Tan et al.
U.S. Appl. No. 29/676,338, filed Jan. 10, 2019, Tan et al.
U.S. Appl. No. 29/728,687, filed Mar. 20, 2020, Cook et al.
U.S. Appl. No. 29/728,688, filed Mar. 20, 2020, Cook et al.
U.S. Appl. No. 29/707,807, filed Oct. 1, 2019, Washington et al.
U.S. Appl. No. 29/707,809, filed Oct. 1, 2019, Washington et al.
All final and non-final office actions for U.S. Appl. No. 16/431,028.
All final and non-final office actions for U.S. Appl. No. 16/431,115.
All final and non-final office actions for U.S. Appl. No. 16/577,120.
All final and non-final office actions for U.S. Appl. No. 16/589,504.
All final and non-final office actions for U.S. Appl. No. 16/918,292.
All final and non-final office actions for U.S. Appl. No. 29/672,822.
All final and non-final office actions for U.S. Appl. No. 29/676,338.
All final and non-final office actions for U.S. Appl. No. 29/707,807.
All final and non-final office actions for U.S. Appl. No. 29/707,809.
All final and non-final office actions for U.S. Appl. No. 29/728,687.
All final and non-final office actions for U.S. Appl. No. 29/728,688.
All final and non-final Office Actions, U.S. Appl. No. 15/979,961.
All final and non-final Office Actions, U.S. Appl. No. 15/981,096.
PCT International Search Report and Written Opinion for PCT/US2018/015363 dated Jun. 4, 2018.
PCT International Search Report and Written Opinion for PCT/US2018/015364 dated Oct. 1, 2018.
PCT International Search Report and Written Opinion for PCT/US2018/030762 dated Aug. 7, 2018.
All Office Actions; U.S. Appl. No. 29/819,499, filed Dec. 15, 2021.
Color Keeper [online], [site visited Oct. 18, 2021], Available from internet, URL: https://shopgemz.com/products/color-keeper?variant=13094595002434&utm_source=google&utm_medium=cpc&utm_campaign=Shopping&gclid=CjOKCQjw5JSLBhCxARIsAHgO2SdAT7LTehpyxM1qTGtnFETDa1Nuo9_cQSOpPwCmsmmdGA1Y0USekQEaAh0iEALw_wcB (Year: 2021).
Paper Pieces Hexagons, announced 2018 [online], [site visited Oct. 14, 2021]. Available from internet, URL:https://www.amazon.com/Paper-Pieces-HEX100B-Hexagons-1200pc/dp/B07DVYV2HN/ (Year 2018).
Rounded hexagon shape, announced 2016 [online], [site visited Oct. 20, 2021], Available from internet, URL:https://www.vexels.com/png-svg/preview/1 39199/rounded-hexagon-shape (Year: 2016).
15658M PCT Search Report and Written Opinion for PCT/ US2020/070191 dated Aug. 28, 2020,14 pages.
Adhesives Research (Pennsylvania, http://12.4.33.51/news/apresmed.him).
All Office Actions; U.S. Appl. No. 14/690,593, filed Apr. 20, 2015.
All Office Actions; U.S. Appl. No. 15/665,886, filed Aug. 1, 2017.
All Office Actions; U.S. Appl. No. 16/901,548, filed Jun. 15, 2020.
All Office Actions; U.S. Appl. No. 16/953,975, filed Nov. 20, 2020.
All Office Actions; U.S. Appl. No. 17/070,205, filed Oct. 14, 2020.
All Office Actions; U.S. Appl. No. 17/357,119, filed Jun. 24, 2021.
All Office Actions; U.S. Appl. No. 29/766,885, filed Jan. 19, 2021.
All Office Actions; U.S. Appl. No. 29/815,500, filed Nov. 16, 2021.
Amerilab Technologies, Inc. (Minnesota. http://www.amerilabtech.comm/).
Anonymous "P8136 Poly(vinyl alcohol)" Internet article, [Online] XP002538935, Retrieved from the Internet: URL hllp/20 NWW.sigmaaldrich.com/catalog/ProductDetail.do?D7=0%N25-SEARCH_CONCAT PNOIBRAND KEY% N4=P8136%7SCIAL% N25=0%QS=ON%F=SPEC retrieved on Jul. 28, 2009, year 2009. 1 pg.
Briscoe et al. "The effects of hydrogen bonding upon the viscosity of aqueous poly( vinyl alcohol) solutions," from Polymer, 41 (2000), pp. 3851-3860.
Cardinal Health (Dublin, Ohio, http://spd.cardinal.com/).
Cima Labs, Inc. (Minnesota, http://www.cimalabs.com/).
Definition of Derivative by Merriam Webster Online Dictionary, Year, 2021.
Design of "Detergent tablets" (Design Registration No. 000634142-0003), (No. of Publicly known information: HH 18274488), Registered Community Designs Bulletin, published by EUIPO on Jan. 9, 2007, 4 pgs.
Design of "Detergent tablets" (Design Registration No. 000634142-0004), (No. of Publicly known information HH18274489), Registered Community Designs Bulletin, published by EUIPO on Jan. 9, 2007, 4 pgs.
Design of "Soaps" accepted on Jul. 11, 1986, Publishing Office: Korean Intellectual Property Office (KIPO), Document Name: Design Gazette (Application No. 3019850005996), Publication Date: Jun. 9, 1986, (No. of Publicly known information: HG21900612), 3 pgs.
Dissolving Soap Strips (Ranir LLC, Michigan, www.ranir.com).
Encyclopedia of Polymer Science and Engineering, vol. 15. 2nd ed., p. 204 308 Silicones, year 1989.
Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.
Hexagon 4 ward soap mold, Soap, Cosmetics, NEW Silicon mold, Published on Sep. 29, 2016, Retrieved from Internet: http://candle-box.com/product/%EC%9C%A1%EA%B0%81-4%EA%B5%AC-%EB%B9%84%Eb%88%84%EB%AA%B0 %EB%93%9C/2206/?page_4=3#none, dated Sep. 10, 2019, 16 pgs.
Hildebrand, T., et al., "Quantification of bone microarchitecture with the structure mode index", Computer Methods in Biomechanics and Biomedical Engineering, vol. 1, Jan. 14, 1997, pp. 15-23.
How Gemz work?, Gemz Hair Care, published on Oct. 1, 2018, retrieved on Apr. 27, 2021, retrieved from the Internet URL: https://www.youtube.com/watch?v=ts1waYk43g4, 3 pgs.
Japanese Paper Soap (http://www.wishingfish.com/papersoap.html).
Kuraray: "Mowiol—Technical data sheet", Jun. 1, 2010 (Jun. 1, 2010), pp. 1-4, XP055119891, Retrieved from the Internet: URL:http://www.kuraray.eu/fileadmin/Downloads/mowiol/TDS_Mowiol_an_20110624.pdf [retrieved on May 23, 2014].
Le Laboratoire du Bain (France, http://www.laboudubain.com/).
M.K. Industries (Gujarat India, http://www.soapstrips.com).
Megulars CarWash Strips: Megulars Inc. California, http://www.automotivedigesl.com/view_art.asp?articles!D=12414.
MOVA Pharmaceutical and Kosmas (USA, http:/lww.icon-pr.com/news/news/prinl.cfm?inv_id=256-1).
Product Review: Gemz Solid Shampoo, Travel As Much, published on Mar. 19, 2019, retrieved on Apr. 27, 2021, retrieved from the Internet URL: https://travelasmuch.com/gemz-solid-shampoo-review/, 14 pgs.
Pure Soap Leafe: (Soap UNLTD. Netherlands, http://www.upandunder.com.uk/eshop/catalogue/testbs.asp?Manufacturer_ID=252&Activity_ID=33&Description_ID).
Raymond C Rowe et al., Polyvinyl Alcohol, Handbook of Pharmaceutical Excipients, 2009, Sixth Edition, Pharmaceutical Press, 564-566.
"Hexagon 4 ward Soap" Retrieved from: https ://www.craftcuts.com/hexagon-craft-shape. html Hexagon wood cutouts, www.craftcuts.com, 1 page, reviewed as early as May 2018 (Year: 2018), 16 pgs.
Sahin et al. "A Study on Physical and Chemical Properties of Cellulose Paper Immersed in Various Solvent Mixtures" International Journal of Molecular Sciences, Jan. 2008; 9(1): 78-88.

(56) References Cited

OTHER PUBLICATIONS

Sanipro Sanitary Products (Italy, http://www.sanipro.iit).
Solution (Toyohashi Japan, http://www.solublon.com).
SPI Pharma (Delaware, http://wwwspipharma.com).
Travelers Passport Paper Soap Sheets (http://www.weddingflavornow.com/index.asp?PageAction=VIEWPROD&PROD&ProdID=510).
Vaughan, C.D. "Solubility, Effects in Product. Package, Penetration and Preservation", Cosmetics and Toiletries, vol. 103, Oct. 1988, 24 pgs.
Vesterby, A.: "Star Volume in Bone Research: A Histomorphometric Analysis of Trabecular Bone Structure Using Vertical Sections", Anal Rec: Feb. 1993, 232(2), pp. 325-334.
Wenda (China, http://www.wenda.com).
Wermuth et al. Drug Discovery, "Drug Discovery Today, 2006", vol. 11 7/8, 348-354, Year 2006.
Zhang et al. "Study on Morphology of Electrospun Poly( vinyl alcohol) Mats," European Polymer Journal 41 (2005), pp. 423-432.
"Green Chemistry", Huazhong University of Science and Technology Press, published on Jun. 30, 2008, pp. 6.
Ni Genshan et al. "Drug Classification and Pharmacology Summary", PLA Press, published on Apr. 30, 1988, pp. 3.
All Office Actions; U.S. Appl. No. 13/173,639, filed Jun. 30, 2011.
All Office Actions; U.S. Appl. No. 13/229,825, filed Sep. 12, 2011.
All Office Actions; U.S. Appl. No. 14/334,862, filed Jul. 18, 2014.
All Office Actions; U.S. Appl. No. 15/170,125, filed Jun. 1, 2016.
All Office Actions; U.S. Appl. No. 15/374,486, filed Dec. 9, 2016.
All Office Actions; U.S. Appl. No. 15/978,503, filed May 14, 2018.
All Office Actions; U.S. Appl. No. 16/674,837, filed Nov. 5, 2019.
All Office Actions; U.S. Appl. No. 17/184,712, filed Feb. 25, 2021.
All Office Actions; U.S. Appl. No. 17/979,407, filed Feb. 11, 2022.
Hiroshi Yagi & 4 Others, Research Study of a Friction Protector for Preventing a Tow Line From Breaking,Working Papers for Fiscal 2006 1 Japan 1 Japan Coast Guard IDec. 2007, pp. 1-8.
Latorre Carmen, Nanotribological Effects of Hair Careproducts and Environment on Human Hair Using Atomic Forcemicroscopy,Journal of Vacuum Science and Technology: Part A, U.S.A, AVS/AIP , Jun. 28, 2005 , V2 3 N 4, p. 1034-1045.
L'Alimentation article, Dizolve Group Corporation, Nov. 2010, p. 28.
Makadia, et al., "Poly Lactic-co-Glycolic Acid (PLGA) as Biodegradable Controlled Drug Delivery Carrier", Polymers, 3, pp. 1377-1397 (2011).
Menard et al., "Gnotobiotic Mouse Immune Response Induced by *Bifidobacterium* sp. Strains Isolated from Infants", Applied and Environmental Microbiology, vol. 74, Issue 3, Feb. 1, 2008, pp. 660-666.
Minifibers, Inc., accessed on line at http://www.minifibers.com/documents/Choosing-the-Proper-Short-Cut-Fiber.pdf Oct. 3, 2016.
Overview of pharmaceutical excipients used in tablets and capsules in Drug Topics, dated Oct. 24, 2008. Downloaded Sep. 20, 2016 from http://drugtopics.modernmedicine.com/drugtopics/news/modernmedicine/modernmedicinenews/overviewpharmaceuticalexcipientsusedtablets.
Smith, et al., "Nanofibrous Scaffolds and Their Biological Effects", Nantechnologiesfor the Life Sciences, vol. 9, pp. 188-215 (2006).
Unpublished U.S. Appl. No. 17/979,407, filed Feb. 11, 2022 to Hongsing Tan et al.
W S Ratnayake and D S Jackson. Gelatinization and solubility of corn starch during heating in excess water. Facultyu Publications in Food Science and Technology, Jan. 1, 2006. Also published in Journal of Agricultural and Food Chemistry 54:1 0(2006), pp. 3712-3716.
Wang, et al., "A Novel Controlled Release Drug Delivery System for Multiple DrugsBased on Electrospun Nanofibers Containing Nanoparticles", Journal ofPharmaceutical Sciences, vol. 99, No. 12 (Dec. 2010).
Yasuhiro Hiramatsu et al. "Bifidobacterium Components Have Immunomodulatory Characteristics Dependent on the Method of Preparation" Cytotechnology, Kluwer Academic Publishers, Do, vol. 55, Issue No. 2-3, Nov. 1, 2007, p. 79-87.

\* cited by examiner

DISSOLVABLE SOLID FIBROUS ARTICLES CONTAINING ANIONIC SURFACTANTS

FIELD OF THE INVENTION

The present invention relates to fibrous articles, more particularly to fibrous articles comprising one or more anionic surfactants where the fibrous article lacks a lamellar structure.

BACKGROUND OF THE INVENTION

Many personal care and other consumer products, including shampoos, in the market today are sold in liquid form. While widely used, liquid products often have tradeoffs in terms of packaging, storage, transportation, and convenience of use. For example, these products are generally formulated with a substantial amount of water (e.g. ~80% or more), preservatives, and stabilizers, that add significant bulk and translates to inefficient, costly shipping and storage. Also, liquid personal care products can be difficult to use in terms of controlling dosage and the delivery of the product.

In order to overcome some of these drawbacks, it can be desirable to formulate personal care products as solid articles that can include dissolvable films, compressed powders in a solid, fibrous articles, porous foams, soluble deformable solids, powders, bars or prills. However, many of these executions are not ideal for consumers. For example, some products including many bars or prills, do not hydrate and dissolve fast enough when exposed to water to satisfy the consumer's desire to quickly apply a homogeneous liquid product to the hair, scalp, and/or body, without undue effort to dissolve the product. Other executions, including some fibrous articles, dissolve quickly, but form a lumpy liquid shampoo composition, resembling curdled milk, instead of a smooth, homogenous, creamy liquid shampoo.

As such, there remains a need for solid fibrous shampoo articles where the article has consumer acceptable hydration and rapidly disintegrates into a smooth, creamy liquid shampoo.

SUMMARY OF THE INVENTION

A dissolvable solid fibrous shampoo article comprising fibrous elements comprising: (a) from about 1% to about 50%, by weight on a dry article basis of a polymeric structurant; (b) from about 10% to about 90%, by weight on a dry article basis, of a surfactant system wherein the surfactant system is substantially free of sulfate-based surfactants; (c) optionally a cationic polymer comprising a weight average molecular weight from about 100,000 g/mol to about 2.5 million g/mol as measured by gel permeation chromatography and a charge density of greater than 0.5 meq/g as measured according to the Charge Density Test Method;
  wherein the fibrous article is substantially free of a lamellar structure as determined by the Lamellar Structure Test Method; wherein the fibrous article comprises a hand dissolution of less than 15 strokes according to the Hand Dissolution Test Method.

A dissolvable solid fibrous shampoo article comprising fibrous elements comprising: (a) from about 1% to about 50%, by weight on a dry article basis, polymeric structurant; (b) from about 20% to about 70%, by weight on a dry article basis, of a surfactant system comprising: (i) from about 35% to about 90%, by weight of the surfactant system on a dry article basis, of a primary anionic surfactant; and (ii) from about from about 10% to about 65%, by weight of the surfactant system on a dry article basis, of a co-surfactant; wherein the fibrous article is substantially free of a lamellar structure as determined by the Lamellar Structure Test Method; wherein the fibrous article comprises a hand dissolution of less than 15 strokes.

A dissolvable solid fibrous shampoo article comprising fibrous elements comprising: (a) from about 10% to about 40%, on a dry article basis, of a polyvinyl alcohol; (b) from about 20% to about 80%, on a dry article basis, of a surfactant system comprising: (i) from about 45% to about 80%, by weight of the surfactant system on a dry article basis, of a primary anionic surfactant selected from the group consisting of disodium cocoyl glutamate, disodium laureth sulfosuccinate, and combinations thereof; (ii) from about 20% to about 55%, by weight of the surfactant system on a dry article basis, of a co-surfactant selected from the group consisting of lauramidopropyl betaine, sodium cocoyl isethionate, lauryl hydroxysyltaine and combinations thereof; (c) from about 0.1% to about 2%, on a dry article basis, of a cationic polymer comprising a weight average molecular weight from about 500,000 g/mol to about 2.5 million g/mol as measured by gel permeation chromatography and a charge density of greater than 0.5 meq/g; wherein the cationic polymer is selected from the group consisting of Polyquaternium-6, Polyquaternium-10, cationic guars comprising a molecular weight greater than and combinations thereof.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

When articles containing fibrous elements include shampoo actives, consumers have little patience to wait for the article to dissolve in their palms. Furthermore, they want the dissolved article to be a homogeneous, smooth, creamy shampoo composition, that looks and feels like a traditional liquid shampoo.

Figure 1:
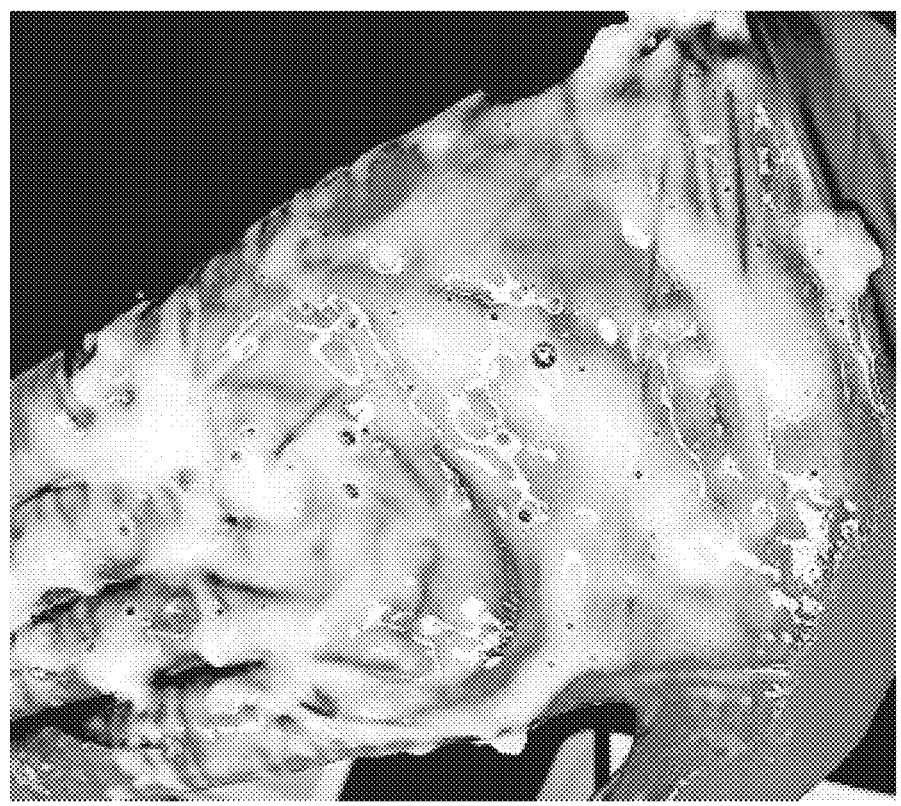
FIG. 1 is a photograph of a liquid shampoo that formed after hydration of a comparative fibrous article where the shampoo has a lumpy texture.

However, some articles containing fibrous elements dissolve into a shampoo with a chunky consistency that can resemble curdled milk. While not willing to be bound by theory, the surfactant system in current fibrous articles can form lamellar structures. Articles with lamellar structures can be difficult to hydrate and when hydrated and diluted can form high viscosity shampoo compositions with a lumpy consistency. FIG. 1 is a photograph of a liquid shampoo composition that was formed after hydration and dilution of a fibrous article and rubbing the fibrous article six times between the palms. The liquid shampoo has visible lumps, which may not be consumer preferred. FIG. 1 corresponds to Comparative Example A, described in Table 1, hereafter, and contains a surfactant system with a sulfate-based surfactant, sodium laureth 1 sulfate, as the primary surfactant.

Figure 2:
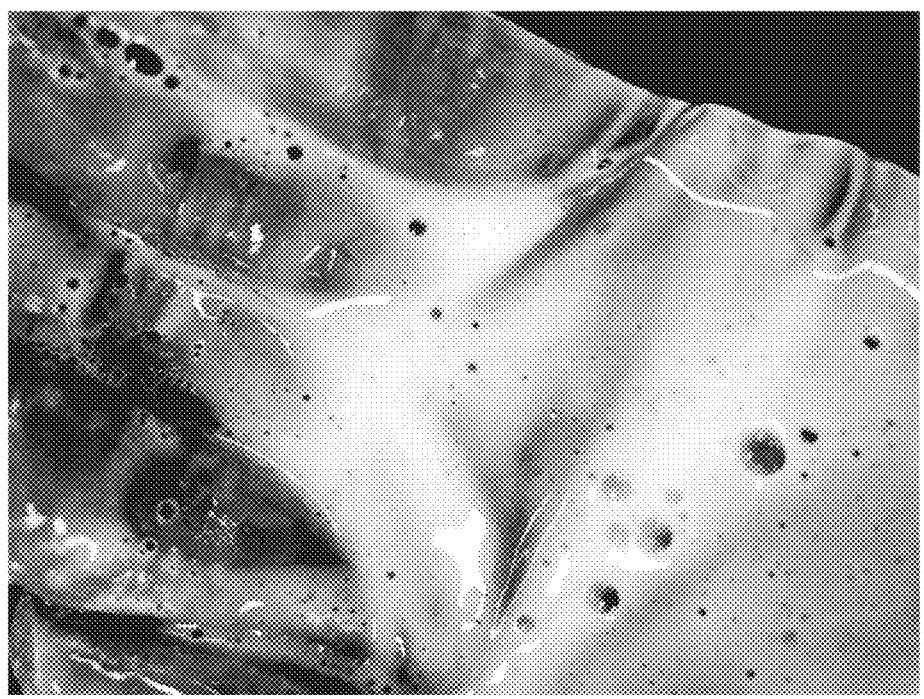
FIG. 2 is a photograph of a liquid shampoo that formed after hydration of an inventive fibrous article where the shampoo has a smooth texture.

It was surprisingly found that when the fibrous articles lacked a lamellar structure, as determined by the Lamellar Structure Test Method, described hereafter, the resulting shampoo composition was smooth, creamy, and homogeneous. FIG. 2 is a photograph of a liquid shampoo composition, which corresponds to Example A, described in Table 1, hereafter, that was formed after hydration and dilution of a fibrous article and rubbing the fibrous article six times between the palms. In this example, the liquid shampoo has a smooth, creamy texture that may be consumer preferred, since it looks, feels, and performs like traditional liquid shampoo products. It was also found that the water diffusion rate, as determined by the Diffusion Coefficient Measurement, described hereafter, was significantly faster when the solid articles lacked a lamellar structure. Solid articles that lack a lamellar structure can be formed by careful selection of primary surfactants (e.g. disodium cocoyl glutamate and/or disodium laureth sulfosuccinate).

The dissolvable solid article can have a hand dissolution value (as determined by the Hand Dissolution Method, described hereafter) of less than about 25 strokes, alternatively less than about 15 strokes, alternatively less than 12 strokes, alternatively less than 10 strokes, alternatively from about 1 to about 25 strokes, alternatively from about 2 to about 15 strokes, alternatively from about 3 to about 10 strokes, and alternatively from about 3 to about 9 strokes.

The dissolvable solid article can have a diffusion coefficient (as determined by the Diffusion Coefficient Measurement, described hereafter) of greater than 5.5e-13, alternatively greater than 5.2e-13, alternatively greater than 5e-13, alternatively greater than 7e-13, alternatively greater than 1e-12, alternatively greater than 1.5e-12, alternatively greater than 1.7e-12, alternatively greater than 2e-12. The dissolvable solid article can have a diffusion coefficient from about 5.5e-13 to about 1e-11, alternatively from about 5.4e-13 to about 7e-12, alternatively from about 5.3e-13 to about 6e-12, alternatively from about 1e-12 to about 5e-12, alternatively from about 1.3e-12 to about 4.5e-12, alternatively from about 1.5e-12 to about 2.5e-12.

Figure 3:
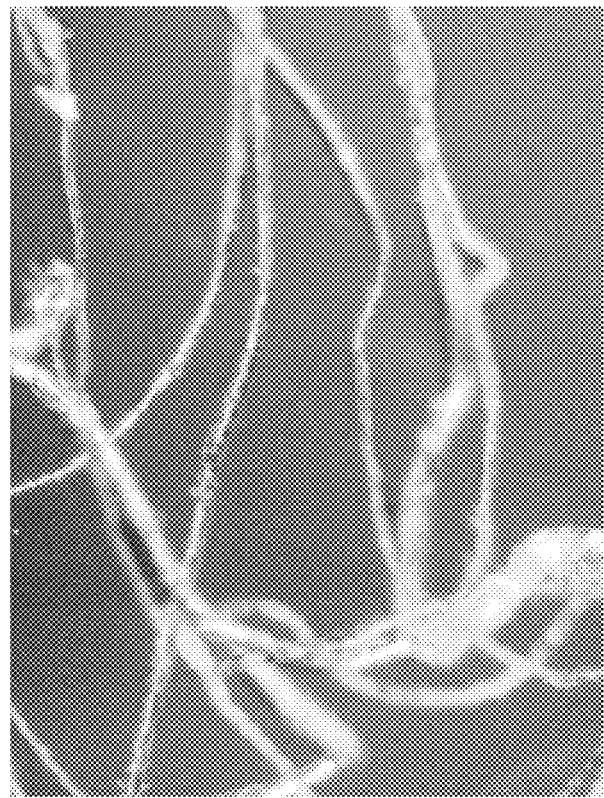
FIG. 3 is a photograph of a fibrous web of comparative example under a light microscope at 10×.

FIG. 3 is a photograph of the fibrous web of Comparative Example A in Table 1, described hereafter, under a light microscope at 10×. The primary surfactant is sodium laureth 1 sulfate, a sulfate-based surfactant. The filaments appear opaque and rough, due to a crystal-like structure within the filaments and on the surface of the filaments. It is hypothesized that the crystal-like appearance is the surfactants in the lamellar structure crystallizing and migrating to the surface of the filaments.

Figure 4:
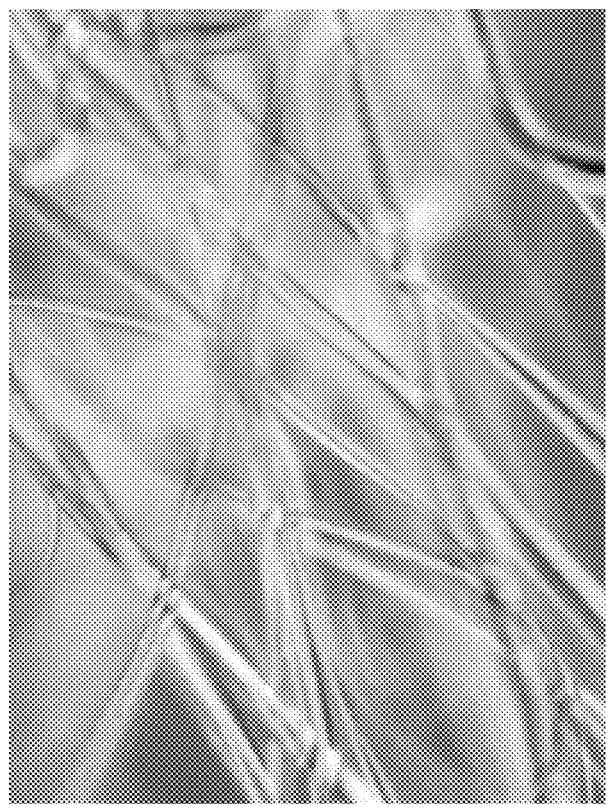
FIG. 4 is a photograph of an inventive fibrous web under a light microscope at 10×.

FIG. 4 is a photograph of a fibrous web of Example A in Table 1, described hereafter, under a light microscope at 10×. The surfactant system in Example A comprises disodium cocoyl glutamate as the primary surfactant and lauramidopropyl betaine (LAPB) and sodium cocoyl isethionate co-surfactants. Example A has a surfactant system that is substantially free of sulfate-based surfactants. The filaments appear translucent with smooth edges. Example A lacks a lamellar structure. It is hypothesized that surfactant in Example A forms spherical micelles that are small and are not crystalizing or migrating, as compared to the lamellar structures in FIG. 3.

Figure 5:
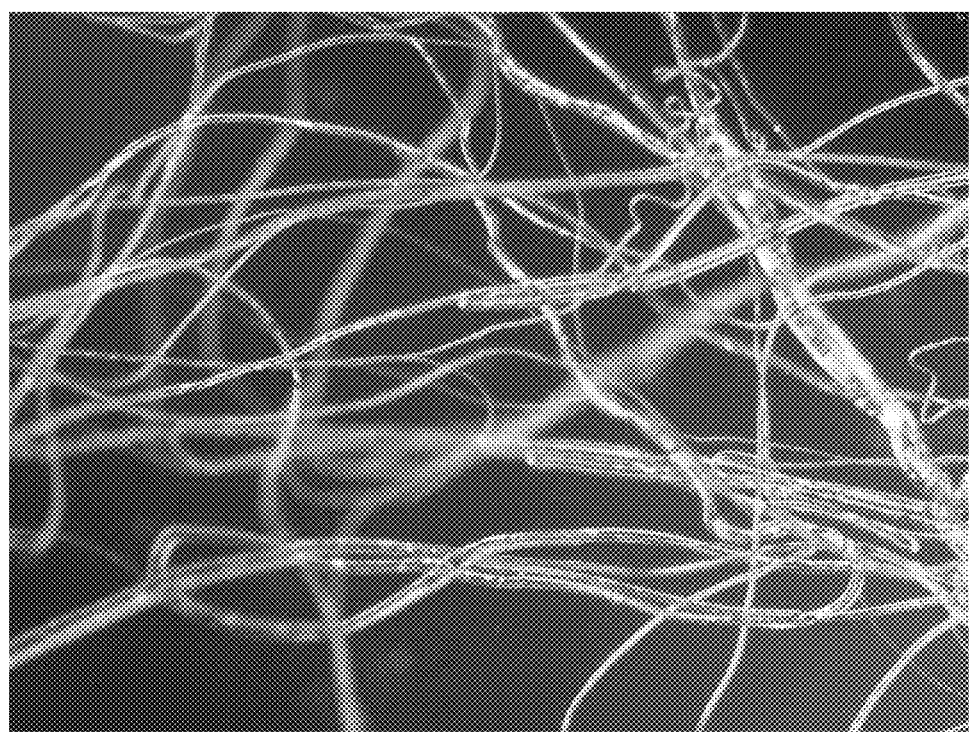
FIG. 5 is a photograph of a fibrous web, with the same composition as the fibrous web of FIG. 4 after four months of storage in a Ziploc® bag at ambient temperature.

FIG. 5 is a photograph of a fibrous web, with the same composition as the fibrous web of FIG. 4 after four months of storage in a quart-size Ziploc® bag at ambient conditions. Even after storage, the filaments in FIG. 5 look similar to the filaments in FIG. 4, since they are substantially translucent and have a substantially smooth surface.

In addition to a smooth consistency, consumers also want a shampoo to provide a creamy lather with enough volume that is easy to distribute throughout the hair and provides a signal of excellent cleaning. However, not all surfactants that lack a lamellar structure have good lather. For instance, a formula that contained a highly branched surfactant C12-13 alkyl sulfate (see Table 1, Comparative Example B, hereafter) hydrates quickly but may not form sufficient lather and therefore it may not contain a preferred primary surfactant.

The dissolvable article can have a lather score of greater than 2, alternatively greater than 3, alternatively greater than 4, and alternatively greater than 5 according to the Lather Method, described herein. The dissolvable article can have a lather score of from about 2 to about 8, alternatively from about 3 to about 7, and alternatively from about 4 to about 6.

Finally, it may be desirable to incorporate relatively high weight average molecular weight cationic polymers and/or cationic polymers with a relatively high charge density (e.g. polydiallyldimethylammonium chloride (polyDADMAC), Polyquaternium-10 and/or guar hydroxypropyltrimonium chloride (e.g. Jaguar® Excel available from Solvay® and N-Hance 3196 available from Ashland™), into shampoo formulations to provide wet conditioning by forming coacervates with the anionic surfactant(s) and to help with deposition of actives, such as silicones or antidandruff actives, onto the hair. However, in fibrous articles with certain surfactants, including many common sulfate-based surfactants, it can be difficult to incorporate these cationic polymers into the filaments because the melt composition is not phase stable, which makes it extremely difficult to spin the composition to form homogeneous filaments.

It was found that surfactant systems that lack a lamellar structure, can be compatible with relatively high weight average molecular weight cationic polymers with relatively high charge density and form a stable melt composition (i.e. no phase separation or precipitate is formed) with an acceptable rheology that can be spun into homogeneous filaments. These same surfactants can be used in fibrous articles that can easily disperse into a smooth, creamy shampoo that provides some conditioning to the hair.

Definitions

"Dissolvable" means that the Dissolvable Solid article is completely soluble in water or it provides a uniform dispersion upon mixing in water according to the Hand Dissolution Test, described hereafter. The Dissolvable Solid article can have a hand dissolution value of from about 1 to about 30 strokes, alternatively from about 2 to about 25 strokes, alternatively from about 3 to about 20 strokes, and alternatively from about 4 to about 15 strokes, as measured by the Hand Dissolution Method.

"Fibrous article" as used herein means a structure that comprises one or more fibrous elements and optionally, one or more particles. In one example, a fibrous article according to the present invention means an association of fibrous elements and optionally, particles that together form a structure, such as a unitary structure, capable of performing a function.

Figure 6:
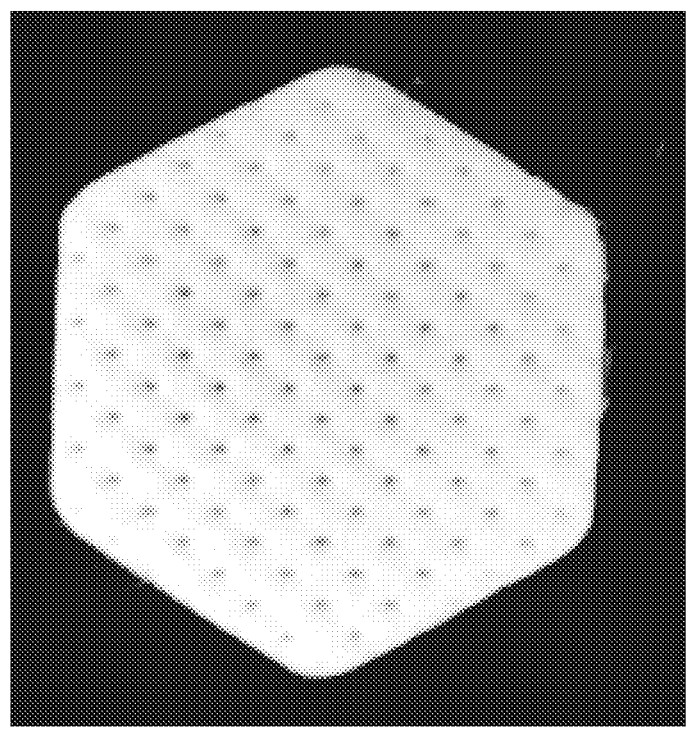
FIG. 6 is an example of a fibrous article containing filaments.

FIG. 6 is an example of a fibrous article containing filaments.

The fibrous articles of the present invention may be homogeneous or may be layered. If layered, the fibrous articles may comprise at least two and/or at least three and/or at least four and/or at least five layers, for example one or more fibrous element layers, one or more particle layers and/or one or more fibrous element/particle mixture layers. A layer may comprise a particle layer within the fibrous article or between fibrous element layers within a fibrous article. A layer comprising fibrous elements may sometimes be referred to as a ply. A ply may be a fibrous article which may be homogeneous or layered as described herein.

In one example, a single-ply fibrous article according to the present invention or a multi-ply fibrous article comprising one or more fibrous article plies according to the present invention may exhibit a basis weight of less than 5000 g/m² as measured according to the Basis Weight Test Method described herein. In one example, the single- or multi-ply fibrous article according to the present invention may exhibit a basis weight of greater than 10 g/m² to about 5000 g/m² and/or greater than 10 g/m² to about 3000 g/m² and/or greater than 10 g/m² to about 2000 g/m² and/or greater than 10 g/m² to about 1000 g/m² and/or greater than 20 g/m² to about 800 g/m² and/or greater than 30 g/m² to about 600 g/m² and/or greater than 50 g/m² to about 500 g/m² and/or greater than 100 g/m² to about 800 g/m² and/or greater than 200 g/m² to about 600 g/m² as measured according to the Basis Weight Test Method.

In one example, the fibrous article of the present invention can be a "unitary fibrous article." "Unitary fibrous article" as used herein is an arrangement comprising a plurality of two or more and/or three or more fibrous elements that are inter-entangled or otherwise associated with one another to form a fibrous article. The unitary fibrous article can optionally contain particles. A unitary fibrous article of the present invention may be one or more plies within a multi-ply fibrous article. In one example, a unitary fibrous article of the present invention may comprise three or more different fibrous elements. In another example, a unitary fibrous article of the present invention may comprise two different fibrous elements, for example a co-formed fibrous article, upon which a different fibrous element is deposited to form a fibrous article comprising three or more different fibrous elements.

"Article" as used herein refers to a consumer use unit, a consumer unit dose unit, a consumer use saleable unit, a single dose unit, or other use form comprising a unitary fibrous article and/or comprising one or more fibrous articles of the present invention.

"By weight on a dry filament basis" means that the weight of the filament measured immediately after the filament has been conditioned in a conditioned room at a temperature of 22° C.±2° C. and a relative humidity of 42%±4% for 2 hours. Similarly, "by weight on a dry fibrous element basis" or "by weight on a dry fibrous article basis" means the weight of the fibrous element or structure after the fibrous element has been conditioned in a conditioned room at a temperature of 22° C.±2° C. and a relative humidity of 42%±4% for 2 hours.

"Fibrous element" as used herein means an elongate particulate having a length greatly exceeding its average diameter, i.e. a length to average diameter ratio of at least about 10. A fibrous element may be a filament or a fiber. In one example, the fibrous element can be a single fibrous element rather than a yarn comprising a plurality of fibrous elements.

The fibrous elements of the present invention may be spun from a filament-forming composition also referred to as fibrous element-forming compositions via suitable spinning process operations, such as meltblowing, spunbonding, electro-spinning, and/or rotary spinning.

The fibrous elements of the present invention may be monocomponent and/or multicomponent. For example, the fibrous elements may comprise bicomponent fibers and/or filaments. The bicomponent fibers and/or filaments may be in any form, such as side-by-side, core and sheath, islands-in-the-sea and the like.

"Filament" as used herein means an elongate particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments.

"Fiber" as used herein means an elongate particulate as described above that exhibits a length of less than 5.08 cm (2 in.) and/or less than 3.81 cm (1.5 in.) and/or less than 2.54 cm (1 in.).

Fibers are typically considered discontinuous in nature. Non-limiting examples of fibers include staple fibers produced by spinning a filament or filament tow of the present invention and then cutting the filament or filament tow into segments of less than 5.08 cm (2 in.) thus producing fibers.

In one example, one or more fibers may be formed from a filament of the present invention, such as when the filaments are cut to shorter lengths (such as less than 5.08 cm in length). Thus, in one example, the present invention also includes a fiber made from a filament of the present invention, such as a fiber comprising one or more polymeric structurants and one or more other ingredients, such as surfactants and high melting point fatty materials. Therefore, references to filament and/or filaments of the present invention herein also include fibers made from such filament and/or filaments unless otherwise noted. Fibers are typically considered discontinuous in nature relative to filaments, which are considered continuous in nature.

Figure 7:
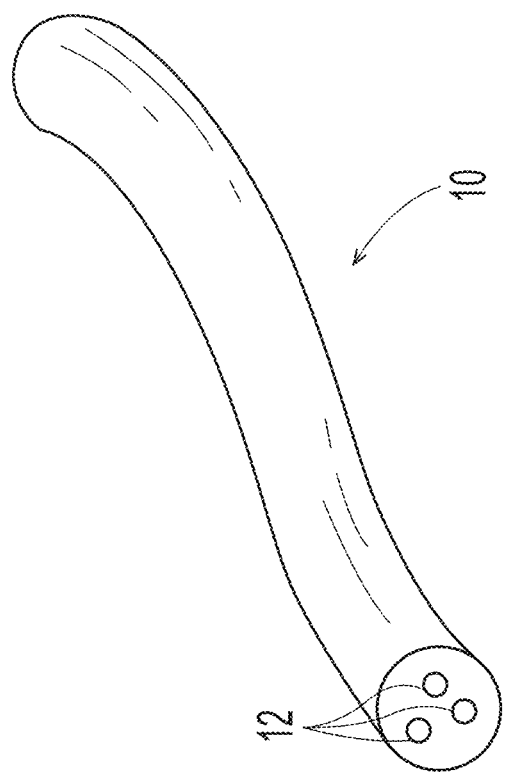
FIG. 7 is a schematic representation of an example of a fibrous element according to the present invention.

"Filament-forming composition" and/or "fibrous element-forming composition" as used herein means a composition that can be suitable for making a fibrous element of the present invention such as by meltblowing and/or spunbonding. The filament-forming composition comprises one or more polymeric structurants that exhibit properties that make them suitable for spinning into a fibrous element. In addition, the filament-forming composition may comprise one or more polar solvents, such as water, into which one or more, for example all, of the polymeric structurant and/or one or more, for example all, of surfactants are dissolved and/or dispersed prior to spinning a fibrous element, such as a filament from the filament-forming composition. In one example as shown in FIG. 7, a filament 10 of the present invention made from a filament-forming composition of the present invention is such that one or more additives 12, for example one or more active agents, may be present in the filament rather than on the filament, such as a coating composition comprising one or more active agents, which may be the same or different from the active agents in the fibrous elements and/or particles.

In one example, one or more additives, such as active agents, may be present in the fibrous element and one or more additional additives, such as active agents, may be present on a surface of the fibrous element. In another example, a fibrous element of the present invention may comprise one or more additives, such as active agents, that are present in the fibrous element when originally made, but then bloom to a surface of the fibrous element prior to and/or when exposed to conditions of intended use of the fibrous element.

As used herein, "vinyl pyrrolidone copolymer" (and "copolymer" when used in reference thereto) refers to a polymer of the following structure (I):

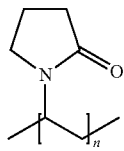

(I)

In structure (I), n is an integer such that the polymeric structurant has the degree of polymerization such that it possesses characteristics described herein. For purposes of clarity, the use of the term "copolymer" is intended to convey that the vinyl pyrrolidone monomer can be copolymerized with other non-limiting monomers such as vinyl acetate, alkylated vinyl pyrrolidone, vinyl caprolactam, vinyl valerolactam, vinyl imidazole, acrylic acid, methacrylate, acrylamide, methacrylamide, dimethacrylamide, alkylaminomethacrylate, and alkylaminomethacrylamide monomers.

As used herein, "vinyl acetate-vinyl alcohol copolymer" (and "copolymer" when used in reference thereto) refers to a polymer of the following structure (I):

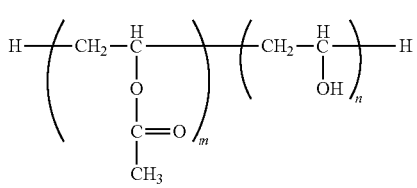

(I)

In structure (I), m and n are integers such that the polymeric structurant has the degree of polymerization and percent alcohol characteristics described herein. For purposes of clarity, this use of the term "copolymer" is intended to convey that the partially hydrolyzed polyvinyl acetate of the present invention comprises vinyl alcohol and vinyl acetate units. As discussed below, the polymeric structurant is routinely prepared by polymerizing vinyl acetate monomer followed by hydrolysis of some of the acetate groups to alcohol groups, as opposed to polymerization of vinyl acetate and vinyl alcohol monomer units (due in-part to the instability of vinyl alcohol).

"Conditions of intended use" as used herein means the temperature, physical, chemical, and/or mechanical conditions that a fibrous element and/or particle and/or fibrous article of the present invention is exposed to when the fibrous element and/or particle and/or fibrous article is used for one or more of its designed purposes. For instance, if a fibrous element and/or a particle and/or a fibrous article comprising a fibrous element is designed to be used by a human as a shampoo for hair care purposes, the conditions of intended use will include those temperature, chemical, physical and/or mechanical conditions present during the shampooing of the human's hair. Likewise, if a fibrous element and/or a particle and/or a fibrous article comprising a fibrous element is designed to be used in a dishwashing operation, by hand or by a dishwashing machine, the conditions of intended use will include the temperature, chemical, physical and/or mechanical conditions present in a dishwashing water and/or dishwashing machine, during the dishwashing operation.

"Active agent" as used herein means an additive that produces an intended effect in an environment external to a fibrous element and/or a particle and/or a fibrous article comprising a fibrous element of the present invention, such as when the fibrous element and/or a particle and/or fibrous article is exposed to conditions of intended use of the fibrous element and/or a particle and/or a fibrous article comprising a fibrous element. In one example, an active agent comprises an additive that treats a surface, including a soft surface (i.e., hair, skin). In another example, an active agent comprises an additive that creates a chemical reaction (i.e., foaming, fizzing, coloring, warming, cooling, lathering, disinfecting and/or clarifying and/or chlorinating, such as in clarifying water and/or disinfecting water and/or chlorinating water). In yet another example, an active agent comprises an additive that treats an environment (i.e., deodorizes, purifies, perfumes). In one example, the active agent is formed in situ, such as during the formation of the fibrous element and/or particle containing the active agent, for example the fibrous element and/or particle may comprise a dissolvable polymer (e.g., starch) and/or a surfactant (e.g., anionic surfactant), which may create a polymer complex or coacervate that functions as the active agent used to treat the hair and/or scalp.

"Treats" as used herein with respect to treating a surface means that the active agent provides a benefit to a surface or environment. Treats includes regulating and/or immediately improving a surface's, cleanliness, smell, purity and/or feel. In one example treating in reference to treating a keratinous tissue (for example skin and/or hair) surface means regulating and/or immediately improving the keratinous tissue's cosmetic appearance and/or feel. For instance, "regulating skin, hair, or nail (keratinous tissue) condition" includes: thickening of skin, hair, or nails (e.g, building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair.

"Weight ratio" as used herein means the ratio between two materials on their dry basis.

"Water-soluble material" as used herein means a material that is miscible in water. In other words, a material that is capable of forming a stable (does not separate for greater than 5 minutes after forming the homogeneous solution) homogeneous solution with water at ambient conditions.

"Water-insoluble" as used herein is meant that the material, particle, and/or substrate that does not dissolve in or readily break apart upon immersion in water. In some instances, water-insoluble materials swell when exposed to water.

"Ambient conditions" as used herein means 22° C.±2° C. and a relative humidity of 42%±4%.

As used herein, "molecular weight" or "M.Wt." refers to the weight average molecular weight unless otherwise stated. Molecular weight is measured using industry standard method, gel permeation chromatography ("GPC").

"Length" as used herein, with respect to a fibrous element, means the length along the longest axis of the fibrous element from one terminus to the other terminus. If a fibrous element has a kink, curl or curves in it, then the length is the length along the entire path of the fibrous element from one terminus to the other terminus.

"Diameter" as used herein, with respect to a fibrous element, is measured according to the Diameter Test Method described herein. In one example, a fibrous element of the present invention exhibits a diameter of less than 100 μm and/or less than 75 μm and/or less than 50 μm and/or less than 25 μm and/or less than 20 μm and/or less than 15 μm and/or less than 10 μm and/or less than 6 μm and/or greater than 1 μm and/or greater than 3 μm.

"Triggering condition" as used herein in one example means anything, as an act or event, that serves as a stimulus and initiates or precipitates a change in the fibrous element and/or particle and/or fibrous article of the present invention, such as a loss or altering of the fibrous element's and/or fibrous article's physical structure and/or a release of an additive, such as an active agent therefrom. In another example, the triggering condition may be present in an environment, such as water, when a fibrous element and/or particle and/or fibrous article of the present invention is added to the water. In other words, nothing changes in the water except for the fact that the fibrous element and/or fibrous article of the present invention is added to the water.

"Morphology changes" as used herein with respect to a fibrous element's and/or particle's morphology changing means that the fibrous element experiences a change in its physical structure. Non-limiting examples of morphology changes for a fibrous element and/or particle of the present invention include dissolution, melting, swelling, shrinking, breaking into pieces, exploding, lengthening, shortening, and combinations thereof. The fibrous elements and/or particles of the present invention may completely or substantially lose their fibrous element or particle physical structure or they may have their morphology changed or they may retain or substantially retain their fibrous element or particle physical structure as they are exposed to conditions of intended use.

"By weight on a dry fibrous element basis" and/or "by weight on a dry fibrous article basis" means the weight of the fibrous element and/or particle and/or fibrous article, respectively, measured immediately after the fibrous element and/or particle and/or fibrous article, respectively, has been conditioned in a conditioned room at a temperature of 22° C.±2° C. and a relative humidity of 42%±4% for 2 hours. In one example, by weight on a dry fibrous element basis and/or dry fibrous article basis means that the fibrous element and/or particle and/or fibrous article comprises less than 20% and/or less than 15% and/or less than 10% and/or less than 7% and/or less than 5% and/or less than 3% and/or to 0% and/or to greater than 0% based on the dry weight of the fibrous element and/or particle and/or fibrous article of moisture, such as water, for example free water, as measured according to the Water Content Test Method described herein.

"Total level" as used herein, for example with respect to the total level of one or more active agents present in the fibrous element and/or particle and/or fibrous article, means the sum of the weights or weight percent of all of the subject materials, for example active agents. In other words, a fibrous element and/or particle and/or fibrous article may comprise 25% by weight on a dry fibrous element basis and/or dry fibrous article basis of an anionic surfactant, 15% by weight on a dry fibrous element basis and/or dry fibrous article basis of a nonionic surfactant, 10% by weight of a chelant on a dry fibrous element basis and/or dry fibrous article basis, and 5% by weight of a perfume a dry fibrous element basis and/or dry fibrous article basis so that the total level of active agents present in the fibrous element and/or particle and/or fibrous article is greater than 50%; namely 55% by weight on a dry fibrous element basis and/or dry fibrous article basis.

"Fibrous article product" as used herein means a solid form, for example a rectangular solid, sometimes referred to as a sheet, that comprises one or more active agents, for example a hair care active agent, a shampoo active agent, a conditioning active agent, and mixtures thereof. In one example, a fibrous article product of the present invention comprises one or more surfactants, one or more enzymes (such as in the form of an enzyme prill), one or more perfumes and/or one or more suds suppressors. In another example, a fibrous article product of the present invention comprises a builder and/or a chelating agent. In another example, a fibrous article product of the present invention comprises a bleaching agent (such as an encapsulated bleaching agent).

"Associate," "Associated," "Association," and/or "Associating" as used herein with respect to fibrous elements and/or particle means combining, either in direct contact or in indirect contact, fibrous elements and/or particles such that a fibrous article is formed. In one example, the associated fibrous elements and/or particles may be bonded together for example by adhesives and/or thermal bonds. In another example, the fibrous elements and/or particles may be associated with one another by being deposited onto the same fibrous article making belt and/or patterned belt.

"Ply" or "Plies" as used herein means an individual fibrous article optionally to be disposed in a substantially contiguous, face-to-face relationship with other plies, forming a multiple ply fibrous article. It is also contemplated that a single fibrous article can effectively form two "plies" or multiple "plies", for example, by being folded on itself.

The term "free of" as used herein means that the composition, or the fibrous article, or the personal cleansing product comprises 0% of an ingredient by total weight of the composition, or by total weight of the fibrous article, or by total weight of the article, thus no detectable amount of the stated ingredient.

The term "substantially free of" as used herein means less than 1%, less than 0.8%, less than 0.5%, less than 0.3%, less than 0.1%, or less than an immaterial amount of a stated ingredient by total weight of the composition, or by total weight of the fibrous article, or by total weight of the personal cleansing product.

As used herein, the articles "a" and "an" when used herein, for example, "an anionic surfactant" or "a fiber" is understood to mean one or more of the material that is claimed or described.

As used herein, the terms "include," "includes," and "including," are meant to be non-limiting.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise noted, all component or composition levels are in reference to the active level of that component or composition, and are exclusive of impurities, for example, residual solvents or by-products, which may be present in commercially available sources.

Fibrous Article

The fibrous article of the present invention can comprise a plurality of fibrous elements, for example a plurality of filaments.

The fibrous article can include: fibrous elements containing a polymeric structurant, a surfactant system, and a relatively high weight average molecular weight cationic surfactant.

FIG. 7 shows a fibrous article according to the present invention. The fibrous article comprises a plurality of fibrous elements, in this case filaments. The filaments contain the polymeric structurant, the surfactant system, and optionally the relatively high molecular weight cationic surfactant, when present. The filament can be homogenous.

Even though the fibrous element and/or fibrous article of the present invention are in solid form, the filament-forming composition used to make the fibrous elements of the present invention may be in the form of a liquid.

In one example, the fibrous article comprises a plurality of identical or substantially identical from a compositional perspective of fibrous elements according to the present invention. In another example, the fibrous article may comprise two or more different fibrous elements according to the present invention. Non-limiting examples of differences in the fibrous elements may be physical differences such as differences in diameter, length, texture, shape, rigidness, elasticity, and the like; chemical differences such as cross-linking level, solubility, melting point, Tg, active agent, polymeric structurant, color, level of active agent, basis weight, level of polymeric structurant, presence of any coating on fibrous element, biodegradable or not, hydrophobic or not, contact angle, and the like; differences in whether the fibrous element loses its physical structure when the fibrous element is exposed to conditions of intended use; differences in whether the fibrous element's morphology changes when the fibrous element is exposed to conditions of intended use; and differences in rate at which the fibrous element releases one or more of its active agents when the fibrous element is exposed to conditions of intended use. In one example, two or more fibrous elements and/or particles within the fibrous article may comprise different active agents. This may be the case where the different active agents may be incompatible with one another, for example an anionic surfactant (such as a shampoo active agent) and a cationic surfactant (such as a hair conditioner active agent).

In another example, the fibrous article may exhibit different regions, such as different regions of basis weight, density and/or caliper. In yet another example, the fibrous article may comprise texture on one or more of its surfaces. A surface of the fibrous article may comprise a pattern, such as a non-random, repeating pattern. The fibrous article may be embossed with an emboss pattern. In another example, the fibrous article may comprise apertures. The apertures may be arranged in a non-random, repeating pattern.

The fibrous article of the present invention may be used as is or may be coated with one or more active agents.

In one example, the fibrous article of the present invention exhibits a thickness of greater than 0.01 mm and/or greater than 0.05 mm and/or greater than 0.1 mm and/or to about 100 mm and/or to about 50 mm and/or to about 20 mm and/or to about 10 mm and/or to about 5 mm and/or to about 2 mm and/or to about 0.5 mm and/or to about 0.3 mm as measured by the Thickness Test Method described herein.

For fibrous articles, the structure can comprise a significant number of dissolvable fibers with an average diameter less than about 150 micron, alternatively less than about 100 micron, alternatively less than about 10 micron, and alternatively less than about 1 micron with a relative standard deviation of less than 100%, alternatively less than 80%, alternatively less than 60%, alternatively less than 50%, such as in the range of 10% to 50%, for example. As set forth herein, the significant number means at least 10% of all the dissolvable fibers, alternatively at least 25% of all the dissolvable fibers, alternatively at least 50% of all the dissolvable fibers, alternatively at least 75% of all the dissolvable fibers. The significant number may be at least 99% of all the dissolvable fibers. Alternatively, from about 50% to about 100% of all the dissolvable fibers may have an average diameter less than about 10 micron. The dissolvable fibers produced by the method of the present disclosure can have a significant number of dissolvable fibers with an average diameter less than about 1 micron, or sub-micron fibers. In an embodiment, fibrous article may have from about 25% to about 100% of all the dissolvable fibers with an average diameter less than about 1 micron, alternatively from about 35% to about 100% of all the dissolvable fibers with an average diameter less than about 1 micron, alternatively from about 50% to about 100% of all the dissolvable fibers with an average diameter less than about 1 micron, and alternatively from about 75% to about 100% of all the dissolvable fibers with an average diameter less than about 1 micron.

The structure can be characterized in one aspect by its Specific Surface Area. The structure can have a Specific Surface Area of from about 0.03 $m^2/g$ to about 0.25 $m^2/g$, alternatively from about 0.035 m²/g to about 0.22 m²/g, alternatively from about 0.04 m²/g to about 0.19 m²/g, and alternatively from about 0.045 m²/g to about 0.16 m²/g.

The structure can be a flat, flexible structure in the form of a pad, a strip, or tape and having a thickness of from about 0.5 mm to about 10 mm, alternatively from about 1 mm to about 9 mm, alternatively from about 2 mm to about 8 mm, and alternatively from about 3 mm to about 7 mm as measured by the below methodology. The Structure can be a sheet having a thickness from about 5 mm to about 6.5 mm. Alternatively, two or more sheets are combined to form a Structure with a thickness of about 5 mm to about 10 mm.

The structure can have a basis weight of from about 200 grams/m² to about 2,000 grams/m², alternatively from about 400 g/m² to about 1,200 g/m², alternatively from about 600 g/m² to about 2,000 g/m², and alternatively from about 700 g/m² to about 1,500 g/m².

The structure can have a dry density of from about 0.08 g/cm³ to about 0.40 g/cm³, alternatively from about 0.08 g/cm³ to about 0.38 g/cm³, alternatively from about 0.10 g/cm³ to about 0.25 g/cm³, and alternatively from about 0.12 g/cm³ to about 0.20 g/cm³.

Non-limiting examples of other fibrous articles suitable for the present invention are disclosed in U.S. Pat. Nos. 8,980,816 and 9,139,802 and U.S. Pub. No. 2013/0171421 are hereby incorporated by reference.

Fibrous Elements

The fibrous element, such as a filament and/or fiber, of the present invention comprises one or more polymeric structurants. In addition to the polymeric structurants, the fibrous element may further comprise a surfactant system and optional ingredients including relatively high weight average molecular weight cationic polymers. Examples of fibrous elements can be found at U.S. patent application Ser. No. 16/431,115, incorporated by reference.

Polymeric Structurant

The dissolvable fibrous article and/or fibrous elements can contain from about 1% to 90%, alternatively 10% to about 80%, alternatively from about 20% to about 70%, alternatively from about 30% to about 65%, and alternatively from about 35% to about 60%, of a polymeric structurant by weight on a dry fibrous element basis and/or a dry dissolvable fibrous article basis and/or by weight of the fibrous element-forming composition.

Non-limiting examples of fibrous-element forming polymeric structurant materials include water-soluble polymers. The water-soluble polymers may be synthetic or natural original and may be chemically and/or physically modified. The polar solvent-soluble polymers may exhibit a weight average molecular weight of from about 10,000 g/mol to about 40,000,000 g/mol, preferably from about 20,000 g/mol to about 30,000,000 g/mol, more preferably from about 35,000 g/mol to about 20,000,000 g/mol, even more preferably from about 40,000 g/mol to about 5,000,000 g/mol, most preferably from about 40,000 g/mol to about 500,000 g/mol.

The one or more fibrous-element forming polymeric structurants comprise one or more polyvinyl alcohols. The one or more polyvinyl alcohols may exhibit a weight average molecular weight of from about 10,000 g/mol to about 40,000,000 g/mol, alternatively from about 20,000 g/mol to about 30,000,000 g/mol, alternatively from about 35,000 g/mol to about 20,000,000 g/mol, alternatively from about 40,000 g/mol to about 5,000,000 g/mol, alternatively from about 40,000 g/mol to about 500,000 g/mol.

The one or more fibrous-element forming polymeric structurant materials may comprise two or more polyvinyl alcohols. One of the two or more polyvinyl alcohols may exhibit a weight average molecular weight of from about 10,000 g/mol to about 100,000 g/mol, alternatively from about 20,000 g/mol to about 50,000 g/mol, alternatively from about 25,000 g/mol to about 45,000 g/mol, and the other of two or more polyvinyl alcohols may exhibit a weight average molecular weight of from about 105,000 g/mol to about 40,000,000 g/mol, preferably from about 110,000 g/mol to about 20,000,000 g/mol, more preferably from about 120,000 g/mol to about 500,000 g/mol.

Non-limiting examples of fibrous-element forming polymeric structurant include water-soluble hydroxyl polymers, water-soluble thermoplastic polymers, water-soluble biodegradable polymers, water-soluble non-biodegradable polymers and mixtures thereof.

The one or more fibrous-element forming polymeric structurant materials may further comprise starch. Preferably, the one or more fibrous-element forming polymeric structurant materials may comprise one or more polyvinyl alcohols and starch.

The one or more fibrous-element forming materials may further comprise carboxymethyl cellulose. The one or more fibrous-element forming polymeric structurant materials may comprise one or more polyvinyl alcohols and carboxymethyl cellulose.

Surfactants

The dissolvable fibrous article and/or fibrous elements can contain from about 10% to about 90%, alternatively from about 20% to about 80%, alternatively from about 30% to about 70%, and alternatively from about 40% to about 65%, of a surfactant system on by weight on a dry fibrous element basis and/or a dry dissolvable fibrous article basis and/or by weight of the fibrous element-forming composition.

The surfactant system can be substantially free or free of sulfate-based surfactants including alkyl sulfate and alkyl ether sulfate type of surfactant. Alternatively, the dissolvable fibrous article does not comprise any alkyl sulfate which comprises $C_{10}$-C18 alkyl sulfate or any alkyl ether sulfate including alkyl glyceryl ether sulfates.

The dissolvable fibrous article may not comprise any alkyl ether sulfates which have the formula:

wherein R is an alkyl or alkenyl having 8 to 18 carbons, alternatively 12 to 18 carbons, n has an average value of greater than at least 0.5, alternatively between 2 and 3; and M is a solubilizing cation such as sodium, potassium, ammonium or substituted ammonium.

The dissolvable fibrous article may not comprise any ammonium and sodium lauryl ether sulfates.

If the dissolvable fibrous article does contain alkyl sulfate and/or alkyl ether sulfate type of surfactant, its content of such a weight proportion of: alkyl sulfates or alkyl ether sulfate type surfactant is less than or equal to the sum of 0.6, alternatively less than or equal to the sum of 0.2, alternatively equal to 0.

Also, the product may be substantially free of alkyl sulfate and alkyl ether sulfate type of surfactant, as described hereinbefore.

The one or more active agents comprise one or more surfactants, wherein the one or more surfactants comprise at least one glutamate surfactant according to the general formula (I):

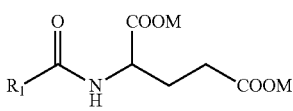

(I)

wherein R₁can be saturated or unsaturated, straight or branched alkyl or alkenyl chain with from 5 to 20 carbon atoms, alternatively with from 7 to 17 carbon atoms, alternatively with from 9 to 13 carbon atoms; and M can be H, ammonium, triethanolammonium (TEA), sodium or potassium and mixtures thereof.

As set out above, the dissolvable fibrous article can be substantially free of alkyl sulfate and alkyl ether sulfate type of surfactants.

The surfactant system can contain from an anionic primary surfactant. The article can contain from about 5% to about 60%, alternatively from about 10% to about 55%, alternatively from about 15% to about 50%, alternatively from about 20% to about 45% primary surfactant by weight of by weight on a dry fibrous element basis and/or a dry dissolvable fibrous article basis and/or by weight of the fibrous element-forming composition.

The surfactant system can contain an anionic primary surfactant. The article can contain from about 35% to about 100%, alternatively from about 37% to about 90%, alternatively from about 40% to about 85%, alternatively from about 45% to about 80%, alternatively from about 48% to about 76% primary surfactant by weight of the surfactant system on a dry fibrous element basis and/or a dry dissolvable fibrous article basis and/or by weight of the fibrous element-forming composition.

The primary surfactant can be an anionic surfactant with two or more negatively charged hydrophilic groups, particularly, two negatively charged hydrophilic groups where the surfactant is substantially free of sulfate-based surfactants. The primary surfactant can include disodium cocoyl glutamate, disodium laureth sulfosuccinate, disodium cocoamphodiacetate, disodium lauroamphodiacetate, and combinations thereof.

The primary anionic surfactant can comprise at least one glutamate surfactant. Non-limiting examples of glutamate surfactants can include sodium cocoyl glutamate, disodium cocoyl glutamate, potassium cocoyl glutamate, dipotassium cocoyl glutamate, ammonium cocoyl glutamate, diammonium cocoyl glutamate, sodium lauroyl glutamate, disodium lauroyl glutamate, potassium lauroyl glutamate, dipotassium lauroyl glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallowoyl glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallowoyl glutamate, sodium cocoyl/palmoyl/sunfloweroyl glutamate, sodium hydrogenated tallowoyl glutamate, sodium olivoyl glutamate, disodium olivoyl glutamate, sodium palmoyl glutamate, disodium palmoyl glutamate, TEA-cocoyl glutamate, TEA-hydrogenated tallowoyl glutamate, TEA-lauroyl glutamate, and mixtures thereof.

The at least one glutamate surfactant may be selected from the group consisting of sodium cocoyl glutamate, disodium cocoyl glutamate, potassium cocoyl glutamate, dipotassium cocoyl glutamate, ammonium cocoyl glutamate, diammonium cocoyl glutamate, sodium lauroyl glutamate, disodium lauroyl glutamate, potassium lauroyl glutamate, dipotassium lauroyl glutamate, sodium capryloyl glutamate, disodium capryloyl glutamate, potassium capryloyl glutamate, dipotassium capryloyl glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, TEA-cocoyl glutamate, and mixtures thereof.

In some examples, the at least one glutamate surfactant may be selected from the group consisting of sodium cocoyl glutamate, disodium cocoyl glutamate, potassium cocoyl glutamate, dipotassium cocoyl glutamate, ammonium cocoyl glutamate, diammonium cocoyl glutamate, TEA-cocoyl glutamate, and mixtures thereof.

The total level of the at least one glutamate surfactant may be from about 8% to about 100%, alternatively from about 8% to about 85%, alternatively from about 12% to about 70%, alternatively from about 17% to about 55%, and alternatively from about 20% to about 45%, by weight of the article. The glutamate level can be by weight on a dry fibrous element basis and/or a dry dissolvable fibrous article basis and/or by weight of the fibrous element-forming composition.

The total level of the at least one glutamate surfactant can be from about 40% to about 100%, alternatively from about 40% to about 85%, alternatively from about 45% to about 80%, alternatively from about 50% to about 75%, by weight of the surfactant system on a dry fibrous element basis and/or a dry dissolvable fibrous article basis and/or by weight of the fibrous element-forming composition.

The one or more surfactants of the one or more active agents may also comprise a co-surfactant by weight of the composition, wherein the co-surfactant can be selected from the group consisting of an additional anionic surfactant, a non-ionic surfactant, an amphoteric surfactant, a zwitterionic surfactant, and mixtures thereof.

The article can optionally contain a co-surfactant. The total level of the co-surfactant can be from about 0.5% to about 50%, alternatively from about 2% to about 30%, alternatively from about 5% to about 25%, alternatively from about 7% to about 20%, by weight of the article on a dry fibrous element basis and/or a dry dissolvable fibrous article basis and/or by weight of the fibrous element-forming composition.

The total level of the co-surfactant can be from about 10% to about 65%, alternatively from about 15% to about 55%, alternatively from about 23% to about 50%, by weight of the surfactant system on a dry fibrous element basis and/or a dry dissolvable fibrous article basis and/or by weight of the fibrous element-forming composition.

The additional anionic surfactant may be selected from the group consisting of an isethionate surfactant, a sarcosinate surfactant, a glycinate surfactant, an alaniate surfactant, a sulfosuccinate surfactant, a sulfonate surfactant, a sulfoacetate surfactant, a glucose carboxylate surfactant, an alkyl ether carboxylate surfactant, a taurate surfactant, and mixtures thereof. Each anionic surfactant just listed above will be described in more details below.

The one or more surfactants of the one or more active agents may also comprise at least one isethionate surfactant according to the general formula (II):

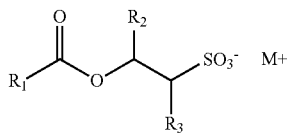
(II)

wherein $R_1$ can be a saturated or unsaturated, straight or branched, alkyl or alkenyl chain with from 6 to 30 carbon atoms, alternatively from 8 to 22 carbon atoms, alternatively from 9 to 18 carbon atoms, $R_2$ and $R_3$ are each independently H or ($C_1$-$C_4$) alkyl, alternatively wherein ($C_1$-$C_4$) alkyl can be methyl, and $M^+$ can be an alkali metal, alternatively lithium, sodium, potassium; or $M^+$ can be an alkali-earth metal, alternatively magnesium; or $M^+$ can be an ammonium or a substituted ammonium cation.

The isethionate surfactant may be selected from the group consisting of sodium lauroyl isethionate, sodium lauroyl methyl isethionate, sodium oleoyl isethionate, sodium oleoyl methyl isethionate, sodium stearoyl isethionate, sodium stearoyl methyl isethionate, sodium myristoyl isethionate, sodium myristoyl methyl isethionate, sodium palmitoyl isethionate, sodium palmitoyl methyl isethionate, sodium cocoyl isethionate, sodium cocoyl methyl isethionate, a blend of stearic acid and sodium cocoyl isethionate, ammonium cocoyl isethionate, ammonium cocoyl methyl isethionate, and mixtures thereof.

The isethionate surfactant may be selected from the group consisting of sodium lauroyl isethionate, sodium lauroyl methyl isethionate, sodium oleoyl isethionate, sodium stearoyl isethionate, sodium myristoyl isethionate, sodium palmitoyl isethionate, sodium cocoyl isethionate, ammonium cocoyl isethionate, and mixtures thereof.

The isethionate surfactant may be selected from the group consisting of sodium lauroyl isethionate, sodium lauroyl methyl isethionate, sodium stearoyl isethionate, sodium myristoyl isethionate, sodium cocoyl isethionate, ammonium cocoyl isethionate, and mixtures thereof.

The isethionate surfactant may be selected from the group consisting of sodium lauroyl isethionate, sodium cocoyl isethionate, ammonium cocoyl isethionate, and mixtures thereof.

Corresponding commercial products are available, for example, from the company Innospec under the trade name "Iselux®" and from Clariant or Uniquema under the trade names "Hostapon®" or Arlatone®. Examples of other commercial fatty acyl isethionates that may be used can be Hostapon® surfactants from Clariant such as for sodium cocoyl isethionate: Hostapon® SCI-85C, Hostapon® SCI-78C, or a blend of stearic acid with sodium cocoyl isethionate: Hostapon® SCI-65C. Examples of other commercial fatty acyl isethionates that may be used can be "Jordapon®" surfactants from BASF such as Jordapon® CI prill or Jordapon® CI65; and sodium cocoyl isethionate from Yongan Daily Chemical Co. such as YA-SCI-85® or YA-SCI-65®.

The sarcosinate surfactant may have the general formula (III):

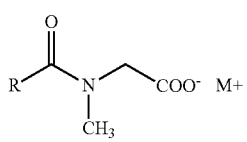
(III)

wherein R can be a saturated or unsaturated, straight or branched alkyl or alkenyl, alternatively alkyl chain with 7 to 17 carbon atoms, alternatively with 9 to 13 carbon atoms and $M^+$ can be H, a sodium, potassium, ammonium or triethanolammonium cation.

The sarcosinate surfactant may be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroyl glutamate/lauroyl sarcosinate, disodium lauroamphodiacetate, lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and mixtures thereof.

Alternatively, the sarcosinate surfactant may be selected from the group consisting of sodium lauroyl sarcosinate, sodium myristoyl sarcosinate, sodium cocoyl sarcosinate, and mixtures thereof.

The glycinate surfactant may be selected from the group consisting of sodium cocoyl glycinate, sodium lauroyl glycinate, and mixture thereof.

The alaninate surfactant may be selected from the group consisting of sodium cocoyl alaninate, sodium lauroyl alaninate, sodium N-dodecanoyl-1-alaninate, and mixture thereof.

The sulfosuccinate surfactant may be selected from the group consisting of disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and mixtures thereof.

The sulfonate surfactant may be selected from the group consisting of alpha olefin sulfonates, linear alkylbenzene sulfonates, sodium laurylglucosides hydroxypropylsulfonate, and mixtures thereof.

The sulfoacetate surfactant may be selected from the group consisting of sodium lauryl sulfoacetate, ammonium lauryl sulfoacetate, and mixture thereof.

The glucose carboxylate surfactant may be selected from the group consisting of sodium lauryl glucoside carboxylate, sodium cocoyl glucoside carboxylate, and mixtures thereof.

The alkyl ether carboxylate surfactant may be selected from the group consisting of sodium laureth-4 carboxylate, laureth-5 carboxylate, laureth-13 carboxylate, sodium C12-13 pareth-8 carboxylate, sodium C12-15 pareth-8 carboxylate and mixtures thereof.

The taurate surfactant may be selected from the group consisting of sodium methyl cocoyl taurate, sodium methyl lauroyl taurate, sodium methyl oleoyl taurate, and mixtures thereof.

The anionic surfactant being not a glutamate surfactant may comprise a lactate or lactylate. Non-limiting example of lactates can include sodium lactate. Non-limiting examples of lactylates can include sodium lauroyl lactylate, sodium cocoyl lactylate, and mixture thereof.

The total level of additional anionic surfactant may be from about 0% to about 20% by weight of the fibrous element-forming composition or on a dry fibrous element basis and/or a dry dissolvable fibrous article basis. Alternatively, the total level of the anionic surfactant being not a glutamate surfactant may be from about 0.5% to about 15% by weight of the fibrous element-forming composition or on a dry fibrous element basis and/or a dry dissolvable fibrous article basis.

The one or more surfactants of the one or more active agents may comprise a non-ionic surfactant. The non-ionic surfactant may be selected from the group consisting alkyl polyglucoside, alkyl glycoside, acyl glucamide and mixtures thereof.

In that case, alkyl can be defined as a saturated or unsaturated, straight or branched alkyl chain with 6 to 30 carbon atoms, alternatively with 8 to 22 carbon atoms, alternatively with 9 to 18 carbon atoms. In that case, acyl can be defined as of formula R—C(O)—, wherein R can be a saturated or unsaturated, straight or branched alkyl or alkenyl, alternatively alkyl chain with 6 to 30 carbon atoms, alternatively with 8 to 22 carbon atoms, alternatively with 9 to 18 carbon atoms.

The alkyl glucoside may be selected from the group consisting of decyl glucoside, cocoyl glucoside, lauroyl glucoside, and mixtures thereof.

The acyl glucamide may be selected from the group consisting of lauroyl/myristoyl methyl glucamide, capryloyl/capryloyl methyl glucamide, cocoyl methyl glucamide and mixtures thereof.

Alternatively, the non-ionic surfactant may be selected from the group consisting of cocoamide monoethanolamine, lauramide monoethanolamine, cocoyl glucoside, lauroyl glucoside, decyl glucoside, and mixtures thereof.

The total level of the non-ionic surfactant may be from about 0% to about 25% by weight of the fibrous element-forming composition or on a dry fibrous element basis and/or a dry dissolvable fibrous article basis. Alternatively, the total level of the non-ionic surfactant may be from about 0.1% to about 15% by weight of the fibrous element-forming composition or on a dry fibrous element basis and/or a dry dissolvable fibrous article basis. Alternatively, the total level of the non-ionic surfactant may be from about 0.5% to about 10% by weight of the fibrous element-forming composition or on a dry fibrous element basis and/or a dry dissolvable fibrous article basis.

Suitable amphoteric or zwitterionic surfactants can include those described in U.S. Pat. Nos. 5,104,646 and 5,106,609.

Amphoteric surfactants can include those that can be broadly described as derivatives of aliphatic secondary and tertiary amines in which an aliphatic radical can be straight or branched chain and wherein an aliphatic substituent can contain from 8 to 18 carbon atoms such that one carbon atom can contain an anionic water solubilizing group, e.g., carboxy, sulfonate, phosphate, or phosphonate. Examples of compounds falling within this definition can be sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378.

The amphoteric surfactant described herein may be selected from the group consisting of sodium lauroamphoacetate, sodium cocoamphoacetate, disodium lauroamphodiacetate, disodium cocodiamphoacetate, and mixtures thereof.

Zwitterionic surfactants suitable for use in the co-surfactants of the one or more active agents described herein may include those that are broadly described as derivatives of aliphatic quaternary ammonium, phosphonium, and sulfonium compounds, in which the aliphatic radicals can be straight or branched chains, and wherein one of the aliphatic substituents can contain from 8 to 18 carbon atoms and one can contain an anionic group, e.g., carboxy, sulfonate, phosphate, or phosphonate.

Hence, the one or more surfactants of the one or more active agents may comprise at least an amphoteric or zwitterionic surfactant selected from the group consisting of cocamidopropyl betaine, lauramidopropyl betaine, cocobetaine, lauryl betaine, lauryl hydroxysultaine, cocamidopropyl hydroxysultaine, coco-hydroxysultaine, coco-sultaine, lauryl sultaine, sodium cocoamphoacetate, disodium cocoamphodiacetate, sodium lauroamphoacetate, disodium lauroamphodiacetate, lauramine oxide, lauryl hydroxysultaine, and mixtures thereof.

Examples of betaine zwitterionic surfactants may include coco dimethyl carboxymethyl betaine, cocoamidopropyl betaine (CAPB), coco-betaine, lauryl amidopropyl betaine (LAPB), oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine, and mixtures thereof.

The total level of the zwitterionic surfactant may be from about 0.5% to about 20% by weight of the fibrous element-forming composition or on a dry fibrous element basis and/or a dry dissolvable fibrous article basis. Alternatively, the total level of the non-ionic surfactant may be from about 2% to about 15% by weight of the fibrous element-forming composition or on a dry fibrous element basis and/or a dry dissolvable fibrous article basis. Alternatively, the total level of the non-ionic surfactant may be from about 4% to about 13% by weight of the fibrous element-forming composition or on a dry fibrous element basis and/or a dry dissolvable fibrous article basis.

Cationic Polymers

The fibrous article can contain from about 0.05% to about 5% cationic polymer, from about 0.1% to about 2% cationic polymer, from about 0.2% to about 1.5% cationic polymer, from about 0.3% to about 1.0% cationic polymer, from about 0.4% to about 0.75% cationic polymer, by weight of the fibrous element-forming composition or on a dry fibrous element basis and/or a dry dissolvable fibrous article basis.

The cationic polymers can have a weight average molecular weight from about 50,000 g/mol to about 2.5 million g/mol, 500,000 g/mol to about 2.5 million g/mol, alternatively from about 125,000 g/mol to about 2 million g/mol, alternatively from about 500,000 g/mol to about 2 million g/mol, alternatively from about 500,000 g/mol to about 1.5 million, alternatively about 500,000 g/mol to about 1 million as measured by gel permeation chromatography. The cationic polymers can have a weight average molecular weight greater than 500,000 g/mol, alternatively greater than 1 million g/mol as measured by gel permeation chromatography.

The cationic polymers can have a weight average charge density greater than 0.2 meq/g, alternatively greater than 0.4 meq/g, alternatively 0.6 meq/g, alternatively 0.8 meq/g, alternatively 1 meq/g, alternatively 1.2 meq/g, alternatively 1.5 meq/g, alternatively 2 meq/g, alternatively greater than 3 meq/g, alternatively greater than 5 meq/g as measured according to the Charge Density Test Method. The cationic polymers can have a weight average charge density from about 0.4 meg/g to about 5 meg/g, alternatively from about 1 meg/g to about 3 meg/g, alternatively from about 1 meg/g to about 2.5 meg/g as measured according to the Charge Density Test Method.

Cationic Guar Polymer

The hair care composition can comprise (a) a cationic guar polymer. Cationic guar polymers are cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

The cationic guar polymer can have a weight average M.Wt. of less than 2.2 million g/mol, or from about 150 thousand g/mol to about 2 million g/mol, or from about 200 thousand to about 1.9 million g/mol, or from about 300 thousand to about 1.8 million g/mol, or from about 400 thousand to about 1.7 million g/mol, or from about 500,000 g/mol to about 1.6 million g/mol. The cationic guar polymer can have a weight average M.Wt. of greater than about 150,000 g/mol, alternatively greater than about 1 million g/mol, alternatively greater than about 1.5 million g/mol, alternatively greater than about 2 million g/mol, and alternatively greater than about 2.5 million g/mol.

The cationic guar polymer can have a weight average charge density of from about 0.2 meq/g to about 2.2 meg/g, or from about 0.3 meq/g to about 2.0 meg/g, or from about 0.4 meq/g to about 1.9 meg/g, or from about 0.5 meq/g to about 1.8 meg/g, or from about 0.6 meq/g to about 1.7 meg/g, or from about 0.6 meq/g to about 1.5 meq/g, or from about 0.6 meq/g to about 1.3 meq/g, and/or from about 0.7 meq/g to about 1.0 meg/g.

The cationic guar polymer may be formed from quaternary ammonium compounds. The quaternary ammonium compounds for forming the cationic guar polymer can conform to the general formula 1:

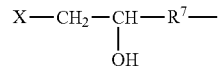

wherein where $R^3$, $R^4$ and $R^5$ are methyl or ethyl groups; $R^6$ is either an epoxyalkyl group of the general formula 2:

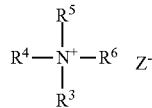

or $R^6$ is a halohydrin group of the general formula 3:

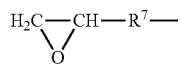

wherein $R^7$ is a $C_1$ to $C_3$ alkylene; X is chlorine or bromine, and Z is an anion such as Cl-, Br-, I- or $HSO_4$—.

The cationic guar polymer can conform to the general formula 4:

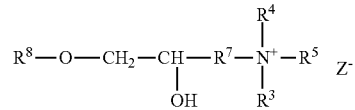

wherein $R^8$ is guar gum; and wherein $R^4$, $R^5$, $R^6$ and $R^7$ are as defined above; and wherein Z is a halogen. The cationic guar polymer can conform to Formula 5:

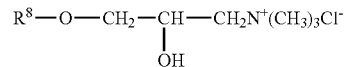

Suitable cationic guar polymers can include cationic guar gum derivatives, such as guar hydroxypropyltrimonium chloride. The cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a weight average molecular weight of 500,000 g/mol. Another guar hydroxypropyltrimonium chloride with a charge density of about 1.1 meq/g and a weight average molecular weight of about 500,000 g/mol is available from Ashland. A further guar hydroxypropyltrimonium chloride with a charge density of about 1.5 meq/g and a weight average molecular weight of about 500,000 g/mole is available from Ashland.

Other suitable guar hydroxypropyltrimonium chloride are: Hi-Care 1000, which has a charge density of about 0.7 meq/g and a weight average molecular weight of about 600,000 g/mole is available from Rhodia; N-Hance 3269 and N-Hance 3270, which have a charge density of about 0.7 meq/g and a weight average molecular weight of about 425,000 g/mol are available from Ashland; N-Hance 3271 which has a charge density of about 0.7 meq/g and a weight average molecular weight of about 500,000 g/mol and is available from Ashland; BF-13, which is a borate (boron) free guar of charge density of about 1.1 meq/g and weight average molecular weight of about 800,000 and BF-17, which is a borate (boron) free guar of charge density of about 1.7 meq/g and M. W.t of about 800,000 both available from Ashland; N-Hance CG17 has a charge density of about 1.0 meq/g and a weight average molecular weight of about 1,600,000 g/mol and is available from Ashland; and N-Hance 3196 has a charge density of about 0.7 meq/g and a weight average molecular weight of 1,700,000 g/mol and is available from Ashland.

Cationic Synthetic Polymer

The hair care composition can include (b) a cationic synthetic polymer, wherein the cationic synthetic polymer can have a weight average M.Wt. of from about 1,000 g/mol to about 2.0 million g/mol, and wherein the cationic guar polymer can have a charge density of from about 2 meq/g to about 10 meq/g. The hair care composition can comprise a cationic synthetic polymer from about 0.01% to about 2.5% by total weight of the composition.

The cationic synthetic polymers may be formed from i) one or more cationic monomer units, and optionally ii) one or more monomer units bearing a negative charge, and/or iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and cationic synthetic polymers having the following structure:

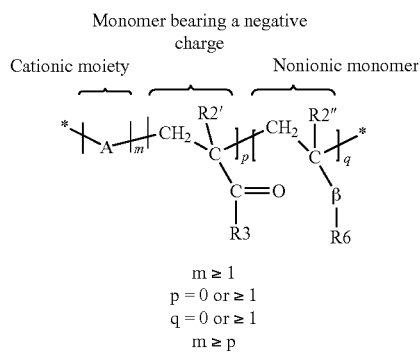

where A, may be one or more of the following cationic moieties:

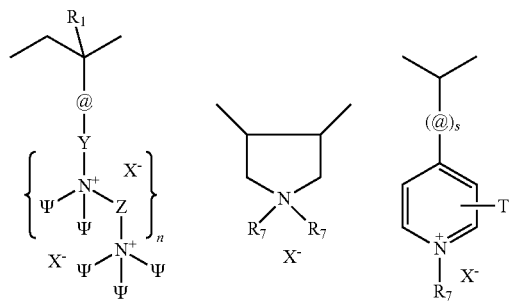

where @=amido, alkylamido, ester, ether, alkyl or alkylaryl;

where Y=C1-C22 alkyl, alkoxy, alkylidene, alkyl or aryloxy;

where ψ=C1-C22 alkyl, alkyloxy, alkyl aryl or alkyl arylox;

where Z=C1-C22 alkyl, alkyloxy, aryl or aryloxy;

where R1=H, C1-C4 linear or branched alkyl;

where s=0 or 1, n=0 or ≥1;

where T and R7=C1-C22 alkyl; and where X—=halogen, hydroxide, alkoxide, sulfate or alkylsulfate.

Where the monomer bearing a negative charge is defined by R2'=H, C1-C4 linear or branched alkyl and R3 as:

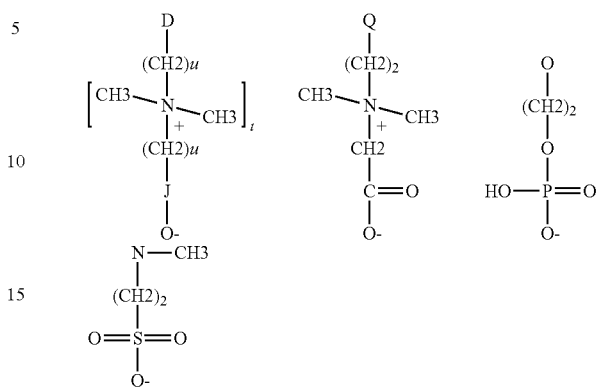

where D=O, N, or S;
where Q=NH2 or 0;
where u=1-6;
where t=0-1; and
where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as

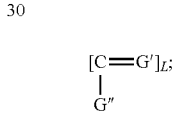

and where G' and G" are, independently of one another, 0, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyl-dialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula $—NR_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X−) in association with the cationic synthetic polymers may be any known counterion so long as the polymers remain soluble or dispersible in water, in the hair care composition, or in a coacervate phase of the hair care composition, and so long as the counterions are physically and chemically compatible with the essential components of the hair care composition or do not otherwise unduly impair product performance, stability or aesthetics. Non limiting examples of such counterions include halides (e.g., chlorine, fluorine, bromine, iodine), sulfate and methylsulfate.

The cationic synthetic polymer can have a weight average M.Wt. of from about 1,500 g/mol to about 1.8 million g/mol, or from about 2,000 g/mol to about 1.7 million g/mol, or from about 3,000 g/mol to about 1.6 million g/mol, or from about 4,000 g/mol to about 1.5 million g/mol, or from about 5,000 g/mol to about 1.6 million g/mol, or from about 6,000 g/mol to about 1.5 million g/mol, or from about 7,000 g/mol to about 1.4 million g/mol, or from about 8,000 g/mol to about 1.4 million g/mol, or from about 9,000 g/mol to about 1.3 million g/mol, or from about 10,000 g/mol to about 1.2 million g/mol or from about 11,000 g/mol to about 1.1 million g/mol, or from about 25,000 g/mol to about 750,000 g/mol, or from about 50,000 g/mol to about 500,000 g/mol, or from about 75,000 g/mol to about 300,000 g/mol, and/or from about 100,000 g/mol to about 200,000 g/mol.

The cationic synthetic polymer can have a weight average charge density of from about 2.2 meq/g to about 9.5 meg/g, or from about 2.5 meq/g to about 8 meg/g, or from about 3 meq/g to about 8 meg/g, or from about 3.5 meq/g to about 7.5 meg/g, and/or from about 4 meq/g to about 7 meg/g.

The cationic synthetic polymer can comprise polydiallyldimethylammonium chloride (polyDADMAC). PolyDADMAC is also known as polyquaternium-6. Specific examples of polyDADMAC are Mirapol® 100 series from Solvay, Merquat™ 100 series from Lubrizol and Salcare® SC 30 from BASF. For example, Mirapol® 100s has a charge density of 6.2 meq/g and a weight average molecular weight of 150,000 g/mol, is available from Solvay.

The hair care composition may further comprise (c) a cationic non-guar galactomannan polymer, (d) a cationic starch polymer, (e) a cationic copolymer of acrylamide monomers and cationic monomers, (f) a cationic cellulose polymer or (g) a mixture of such polymers Cationic Non-Guar Galactomannan Polymers The dispersion compositions can comprise a galactomannan polymer derivative having a mannose to galactose ratio of between 5:1 and 1:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and also is affected by climate. Non Guar Galactomannan polymer derivatives can have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and *Cassia* gum (5 parts mannose/1 part galactose).

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

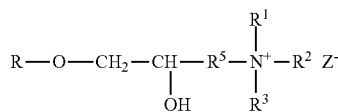

wherein R is the gum. The cationic galactomannan derivative can be a gum hydroxypropyltrimethylammonium chloride, which can be more specifically represented by the general formula 7:

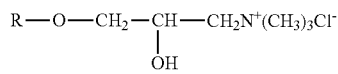

The galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose that is greater than about 4:1. The dispersion compositions may comprise a galactomannan polymer derivative, by weight, of the composition. The hair care compositions can comprise from about 0.05% to about 2%, by weight, of the composition, of a galactomannan polymer derivative.

(d) Cationically Modified Starch Polymer

The dispersion compositions can comprise water-soluble cationically modified starch polymers. As used herein, the term "cationically modified starch" refers to a starch to which a cationic group is added prior to degradation of the starch to achieve a relatively small weight average molecular weight, or wherein a cationic group is added after modification of the starch to achieve a desired weight average molecular weight. The definition of the term "cationically modified starch" also includes amphoterically modified starch. The term "amphoterically modified starch" refers to a starch hydrolysate to which a cationic group and an anionic group are added.

The dispersion compositions can comprise cationically modified starch polymers at a range of about 0.01% to about 10%, and/or from about 0.05% to about 5%, by weight, of the composition.

The cationically modified starch polymers disclosed herein can have a percent of bound nitrogen of from about 0.5% to about 4%.

The dispersion compositions can include starch polymers that is chemically modified by the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a relatively small weight average molecular weight or the cationic groups may be added after such modification.

The cationically modified starch polymers can generally have a degree of substitution of a cationic group from about 0.1 to about 7. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassava starch, waxy barley, waxy rice starch, glutenous rice starch, sweet rice starch, amioca, potato starch, tapioca starch, oat starch, sago starch, sweet rice, or mixtures thereof.

Cationically modified starch polymers can be selected from degraded cationic maize starch, cationic tapioca, cationic potato starch, and mixtures thereof.

The starch, prior to degradation or after modification to achieve a relatively small weight average molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance.gtoreq.80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in compositions is available from known starch suppliers. Nonionic modified starch that could be further derivatized to a cationically modified starch as is known in the art can be suitable. Other suitable modified starch starting materials may be quaternized, as is known in the art, to produce the cationically modified starch polymer suitable for use in the invention.

Starch Degradation Procedure: A starch slurry is prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

Cationic Copolymer of an Acrylamide Monomer and a Cationic Monomer

The dispersion composition can comprise a cationic copolymer of an acrylamide monomer and a cationic monomer. The cationic copolymer can be a synthetic cationic copolymer of acrylamide monomers and cationic monomers.

The cationic copolymer can comprise:
(i) an acrylamide monomer of the following Formula AM:

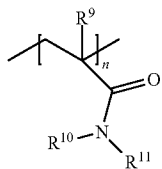

Formula AM
where $R^9$ is H or $C_{1-4}$ alkyl; and $R^{19}$ and $R^H$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and
(ii) a cationic monomer conforming to Formula CM:

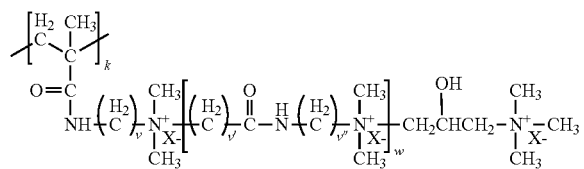

Formula CM
where k=1, each of v, v', and v" is independently an integer of from 1 to 6, w is zero or an integer of from 1 to 10, and $X^-$ is an anion.

The cationic monomer can conform to Formula CM and where k=1, v=3 and w=0, z=1 and $X^-$ is $Cl^-$ to form the following structure:

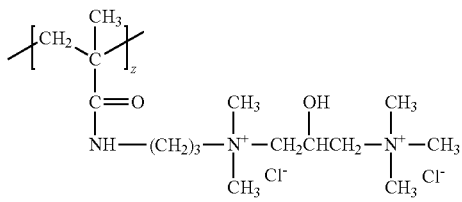

The above structure may be referred to as diquat. The cationic monomer can conform to Formula CM and wherein v and v" are each 3, v'=1, w=1, y=1 and $X^-$ is $Cl^-$, such as:

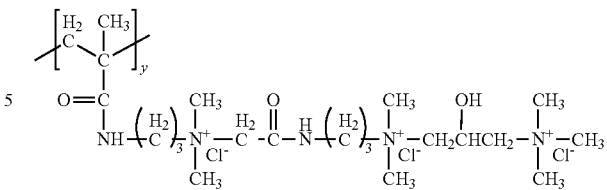

The above structure may be referred to as triquat.

The acrylamide monomer can be either acrylamide or methacrylamide.

The cationic copolymer (b) can be AM:TRIQUAT which is a copolymer of acrylamide and 1,3-Propanediaminium, N-[2-[[[dimethyl[3-[(2-methyl-1-oxo-2-propenyl)amino]propyl]ammonio]acetyl]amino]ethyl]2-hydroxy-N,N,N',N'-pentamethyl-, trichloride. AM:TRIQUAT is also known as polyquaternium 76 (PQ76). AM:TRIQUAT may have a charge density of 1.6 meq/g and a M.Wt. of 1.1 million g/mol.

The cationic copolymer can be an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer comprises a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be water-soluble. The cationic copolymer can be formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. Cationized esters of the (meth)acrylic acid containing a quaternized N atom can be quaternized dialkylaminoalkyl (meth)acrylates with C1 to C3 in the alkyl and alkylene groups. The cationized esters of the (meth)acrylic acid containing a quaternized N atom are selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. The cationized esters of the (meth)acrylic acid containing a quaternized N atom can be dimethylaminoethyl acrylate, which may be quaternized with an alkyl halide, or with methyl chloride or benzyl chloride or dimethyl sulfate (ADAME-Quat). The cationic monomer when based on (meth)acrylamides can be quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

The cationic monomer based on a (meth)acrylamide is a quaternized dialkylaminoalkyl(meth)acrylate with C1 to C3 in the alkyl and alkylene groups. The cationic monomer based on a (meth)acrylamide is dimethylaminopropylacrylamide, which is quaternized with an alkyl halide, especially methyl chloride or benzyl chloride or dimethyl sulfate.

The cationic monomer is a hydrolysis-stable cationic monomer. Hydrolysis-stable cationic monomers can be, in addition to a dialkylaminoalkyl(meth)acrylamide, all monomers that can be regarded as stable to the OECD hydrolysis test. The cationic monomer is hydrolysis-stable and the hydrolysis-stable cationic monomer is selected from the group consisting of: diallyldimethylammonium chloride and water-soluble, cationic styrene derivatives.

The cationic copolymer is a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer is formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer is a trimethylammoniopropylmethacrylamide chloride-N-Acrylamide copolymer, which is also known as AM:MAPTAC. AM:MAPTAC may have a charge density of about 1.3 meq/g and a M.Wt. of about 1.1 million g/mol. The cationic copolymer is AM:ATPAC. AM:ATPAC may have a charge density of about 1.8 meq/g and a M.Wt. of about 1.1 million g/mol.

Cationic Cellulose Polymers

Suitable cationic cellulose polymers are salts of hydroxyethyl cellulose reacted with trimethyl ammonium substituted epoxide, referred to in the industry (CTFA) as Polyquaternium 10 and available from Dow/Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

Extensional Aids

The fibrous elements can contain extensional aids. Nonlimiting examples of extensional aids can include polymers, other extensional aids, and combinations thereof.

In one example, the extensional aids have a weight average molecular weight of at least about 500,000 Da. The weight average molecular weight of the extensional aid is from about 500,000 Da to about 25,000,000 Da, alternatively from about 800,000 Da to about 22,000,000 Da, alternatively from about 1,000,000 Da to about 20,000,000 Da, and alternatively from about 2,000,000 Da to about 15,000,000 Da. The relatively high weight average molecular weight extensional aids can be preferred in some examples of the invention due to the ability to increase extensional melt viscosity and reducing melt fracture.

The extensional aid, when used in a meltblowing process, can be added to the composition of the present invention in an amount effective to visibly reduce the melt fracture and capillary breakage of fibers during the spinning process such that substantially continuous fibers having relatively consistent diameter can be melt spun. Regardless of the process employed to produce fibrous elements and/or particles, the extensional aids, when used, can be present from about 0.001% to about 10%, by weight on a dry fibrous element basis and/or dry fibrous article basis, in one example, and in another example from about 0.005 to about 5%, by weight on a dry fibrous element basis and/or dry fibrous article basis, in yet another example from about 0.01 to about 1%, by weight on a dry fibrous element basis and/or dry fibrous article basis, and in another example from about 0.05% to about 0.5%, by weight on a dry fibrous element basis and/or dry fibrous article basis.

Non-limiting examples of polymers that can be used as extensional aids can include alginates, carrageenans, pectin, chitin, guar gum, xanthum gum, agar, gum arabic, karaya gum, tragacanth gum, locust bean gum, alkylcellulose, hydroxyalkylcellulose, carboxyalkylcellulose, and mixtures thereof.

Nonlimiting examples of other extensional aids can include modified and unmodified polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide, and mixtures thereof.

Optional Ingredients

The article can optionally comprise from about 1 wt. % to about 25 wt. % plasticizer, in one embodiment from about 3 wt. % to about 20 wt. % plasticizer, in one embodiment from about 5 wt. % to about 15 wt. % plasticizer.

When present in the articles, non-limiting examples of suitable plasticizing agents include polyols, copolyols, polycarboxylic acids, polyesters and dimethicone copolyols.

Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol, isosorbide, glucamine, N-methylglucamine and other mono- and polyhydric relatively low weight average molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable plasticizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other relatively low weight average molecular weight esters (e.g., esters of $C_2$-$C_{10}$ alcohols and acids); and any other water soluble plasticizer known to one skilled in the art of the foods and plastics industries; and mixtures thereof.

EP 0283165 B1 discloses suitable plasticizers, including glycerol derivatives such as propoxylated glycerol.

The article may comprise other optional ingredients that are known for use or otherwise useful in compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1992.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, antidandruff agents, perfumes, exfoliating agents, acids, bases, humectants, enzymes, suspending agents, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials. Further non-limiting examples of optional ingredients include encapsulated perfumes, such as by β-cyclodetrins, polymer microcapsules, starch encapsulated accords and combinations thereof.

Suitable conditioning agents can optionally be added to the articles and can include high melting point fatty materials and silicone conditioning agents. Suitable materials are discussed in US 2008/0019935, US 2008/0242584 and US 2006/0217288.

Methods of Use

The compositions described herein may be used for cleaning, conditioning, and/or treating hair, hair follicles, and/or skin including the scalp. The method for treating these consumer substrates may comprise the steps of: a) applying an effective amount of the article to the hand, b) wetting the article with water to dissolve the solid, c) applying the dissolved material to the target consumer substrate to form a lather to clean and optionally condition, and d) rinsing the diluted treatment composition from the consumer substrate. These steps can be repeated as many times as desired to achieve the desired cleansing and or treatment benefit.

A method useful for providing a benefit to hair, hair follicles, and/or skin including the scalp, includes the step of applying a composition according to the first embodiment to these target consumer substrates in need of regulating.

Alternatively, a useful method for regulating the condition of hair, hair follicles, skin, and/or skin including the scalp, includes the step of applying one or more compositions described herein to these target consumer substrates in need of regulation.

The amount of the composition applied, the frequency of application and the period of use will vary widely depending upon the purpose of application, the level of components of a given composition and the level of regulation desired. For example, when the composition is applied for whole body or hair treatment, effective amounts generally range from about 0.5 grams to about 10 grams, alternatively from about 1.0 grams to about 5 grams, and alternatively from about 1.5 grams to about 3 grams.

Product Types and Articles of Commerce

Non-limiting examples of products that utilize the fibrous article include hand cleansing substrates, hair shampoo, hair conditioner or other hair treatment substrates, body cleansing substrates, shaving preparation substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and so forth.

Described herein is an article of commerce comprising one or more fibrous articles described herein, and a communication directing a consumer to dissolve the article and apply the dissolved mixture to hair, hair follicles, and/or skin including the scalp, to achieve a benefit to the target consumer substrate, a rapidly lathering foam, a rapidly rinsing foam, a clean rinsing foam, a conditioning treatment and combinations thereof. The communication may be printed material attached directly or indirectly to packaging that contains the fibrous article or on the fibrous article itself. Alternatively, the communication may be an electronic or a broadcast message that is associated with the article of manufacture. Alternatively, the communication may describe at least one possible use, capability, distinguishing feature and/or property of the article of manufacture.

Exposure to Triggering Condition

The shampoo ingredients, including the surfactant and optionally the cationic polymer, may be released from the fibrous element and/or fibrous article when the fibrous element and/or fibrous article is exposed to a triggering condition. In one example, one or more active agents may be released from the fibrous element and/or fibrous article or a part thereof when the fibrous element and/or fibrous article or the part thereof loses its identity, in other words, loses its physical structure. For example, a fibrous element and/or fibrous article loses its physical structure when the polymeric structurant dissolves, melts or undergoes some other transformative step such that its structure is lost. In one example, the one or more active agents are released from the fibrous element and/or fibrous article when the fibrous element's and/or fibrous article's morphology changes.

In another example, one or more active agents may be released from the fibrous element and/or fibrous article or a part thereof when the fibrous element and/or fibrous article or the part thereof alters its identity, in other words, alters its physical structure rather than loses its physical structure. For example, a fibrous element and/or fibrous article alters its physical structure when the polymeric structurant swells, shrinks, lengthens, and/or shortens, but retains its filament-forming properties.

In another example, one or more active agents may be released from the fibrous element and/or fibrous article with its morphology not changing (not losing or altering its physical structure).

In one example, the fibrous element and/or fibrous article may release an active agent upon the fibrous element and/or fibrous article being exposed to a triggering condition that results in the release of the active agent, such as by causing the fibrous element and/or fibrous article to lose or alter its identity as discussed above. Non-limiting examples of triggering conditions include exposing the fibrous element and/or fibrous article to solvent, a polar solvent, such as alcohol and/or water, and/or a non-polar solvent, which may be sequential, depending upon whether the filament-forming composition comprises a polar solvent-soluble material and/or a non-polar solvent-soluble material; exposing the fibrous element and/or particle and/or fibrous article to heat, such as to a temperature of greater than 75° F. and/or greater than 100° F. and/or greater than 150° F. and/or greater than 200° F. and/or greater than 212° F.; exposing the fibrous element and/or particle and/or fibrous article to cold, such as to a temperature of less than 40° F. and/or less than 32° F. and/or less than 0° F.; exposing the fibrous element and/or fibrous article to a force, such as a stretching force applied by a consumer using the fibrous element and/or fibrous article; and/or exposing the fibrous element and/or fibrous article to a chemical reaction; exposing the fibrous element and/or fibrous article to a condition that results in a phase change; exposing the fibrous element and/or fibrous article to a pH change and/or a pressure change and/or temperature change; exposing the fibrous element and/or fibrous article to one or more chemicals that result in the fibrous element and/or fibrous article releasing one or more of its active agents; exposing the fibrous element and/or particle and/or fibrous article to ultrasonics; exposing the fibrous element and/or fibrous article to light and/or certain wavelengths; exposing the fibrous element and/or fibrous article to a different ionic strength; and/or exposing the fibrous element and/or fibrous article to an active agent released from another fibrous element and/or fibrous article.

In one example, one or more active agents may be released from the fibrous elements of the present invention when a fibrous article product comprising the fibrous elements is subjected to a triggering step such as forming a wash liquor by contacting the fibrous article product with water.

Method for Making Fibrous Elements and Articles

The fibrous elements of the present invention may be made by any suitable process. A non-limiting example of a suitable process for making the fibrous elements is described below.

Figure 8:
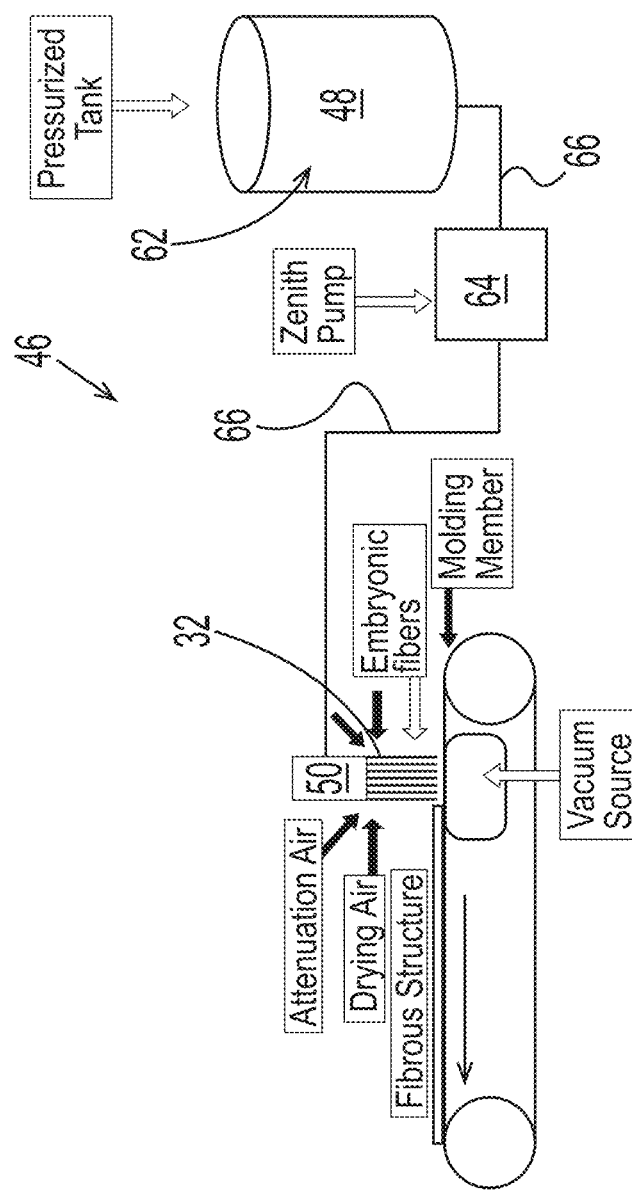
FIG. 8 is a schematic representation of an example of a process for making fibrous elements of the present invention.
Figure 9:
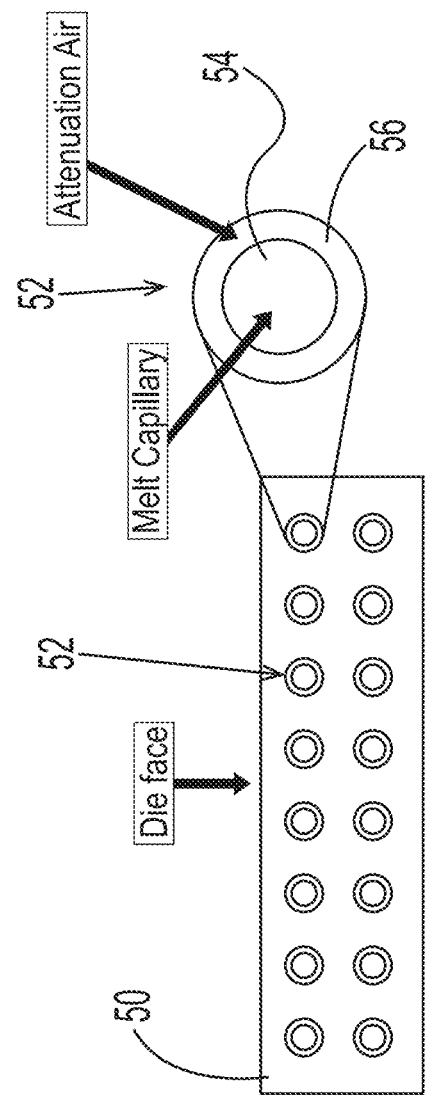
FIG. 9 is a schematic representation of an example of a die with a magnified view used in the process of FIG. 8.

In one example, as shown in FIGS. 8 and 9 a method 46 for making a fibrous element 32 according to the present invention comprises the steps of:

a. providing a filament-forming composition 48 comprising one or polymeric structurants, and optionally one or more other ingredients including high melting point fatty materials and/or one or more surfactants, wherein the filament-forming composition can comprise a pH of greater than about 5.5, alternatively greater than about 5.8, alternatively greater than 6.0; and b. spinning the filament-forming composition 48, such as via a spinning die 50, into one or more fibrous elements 32, such as filaments, comprising the one or more polymeric structurants and optionally, the one or more other ingredients. The one or more other ingredients may be releasable from the fibrous element when exposed to conditions of intended use. The total level of the one or more polymeric structurants present in the fibrous element 32, may be less than 80% and/or less than 70% and/or less than 65% and/or 50% or less by weight on a dry fibrous element basis and/or dry fibrous article basis and the total level of the one or more active agents, when present in the fibrous element may be greater than 20% and/or greater than 35% and/or 50% or greater 65% or greater and/or 80% or greater by weight on a dry fibrous element basis and/or dry fibrous article basis.

As shown in FIG. 9, the spinning die 50 may comprise a plurality of fibrous element-forming holes 52 that include a melt capillary 54 encircled by a concentric attenuation fluid hole 56 through which a fluid, such as air, passes to facilitate attenuation of the filament-forming composition 48 into a fibrous element 32 as it exits the fibrous element-forming hole 52. It was found that if the filament forming composition had a pH of greater than about 5.5, better filaments can form after drying.

In one example, during the method for making fibrous elements, any volatile solvent, such as water, present in the filament-forming composition 48 is removed, such as by drying, as the fibrous element 32 is formed. In one example, greater than 30% and/or greater than 40% and/or greater than 50% and/or greater than 60% and/or greater than 70% of the weight of the filament-forming composition's volatile solvent, such as water, is removed during the spinning step, such as by drying the fibrous element being produced.

It was found that during the spinning step, the inventive examples in Table 1, Table 2, and Table 3, below, can be sensitive to excessive heat exposure during the method for making fibrous elements. For example, if the fibrous elements are exposed to excessive heat for too long the fibrous elements can have active degradation and/or color change and/or odor change. However, the temperature needs to be high enough so the solvent can evaporate within an acceptable time period.

In one example, when the fibrous element exits the fibrous element-forming hole 52, they are collected on a belt above a vacuum source called the forming zone. The fibrous elements can remain on the forming zone for the following times and temperatures: from about 150° F. (65.6° C.) to about 160° F. (71.1° C.) for about 50 to about 60 seconds and/or from about 170° F. (65.6° C.) to about 180° F. (82.2° C.) for about 30 to about 40 seconds and/or from about 200° F. (93.3° C.) to about 215° F. (101.7° C.) for about 5 to about 20 seconds.

In one example, to enable the balance of solvent evaporation, dwell time, and heat exposure it is apparent that melt spinning temperature could be from about 70° F. to about 95° F. while enabling drying with heat such as about 340° F. (171.1° C.) to about 350° F. (176.7° C.) for about 50 to about 60 seconds or from about 390° F. (198.9° C.) to about 400° F. (204° C.) for about 30 to about 40 seconds or 415° F. (212.8° C.) to 470° F. (243.3° C.) for about 5 to about 20 seconds.

The filament-forming composition may comprise any suitable total level of polymeric structurant and any suitable level of active agents so long as the fibrous element produced from the filament-forming composition comprises a total level of polymeric structurant in the fibrous element of from about 5% to 50% or less by weight on a dry fibrous element basis and/or dry fibrous article basis and a total level of active agents in the fibrous element of from 50% to about 95% by weight on a dry fibrous element basis and/or dry fibrous article basis.

In one example, the filament-forming composition may comprise any suitable total level of polymeric structurant and any suitable level of active agents so long as the fibrous element produced from the filament-forming composition comprises a total level of polymeric structurant in the fibrous element and/or particle of from about 5% to 50% or less by weight on a dry fibrous element basis and/or dry fibrous article basis and a total level of active agents in the fibrous element and/or particle of from 50% to about 95% by weight on a dry fibrous element basis and/or dry fibrous article basis, wherein the weight ratio of polymeric structurant to total level of surfactant and/or high melting point fatty material is 1 or less.

In one example, the filament-forming composition comprises from about 1% and/or from about 5% and/or from about 10% to about 50% and/or to about 40% and/or to about 30% and/or to about 20% by weight of the filament-forming composition of polymeric structurant; from about 1% and/or from about 5% and/or from about 10% to about 50% and/or to about 40% and/or to about 30% and/or to about 20% by weight of the filament-forming composition of active agents; and from about 20% and/or from about 25% and/or from about 30% and/or from about 40% and/or to about 80% and/or to about 70% and/or to about 60% and/or to about 50% by weight of the filament-forming composition of a volatile solvent, such as water. The filament-forming composition may comprise minor amounts of other active agents, such as less than 10% and/or less than 5% and/or less than 3% and/or less than 1% by weight of the filament-forming composition of plasticizers, pH adjusting agents, and other active agents.

The filament-forming composition is spun into one or more fibrous elements and/or particles by any suitable spinning process, such as meltblowing, spunbonding, electro-spinning, and/or rotary spinning. In one example, the filament-forming composition is spun into a plurality of fibrous elements and/or particles by meltblowing. For example, the filament-forming composition may be pumped from a tank to a meltblown spinnerette. Upon exiting one or more of the filament-forming holes in the spinnerette, the filament-forming composition is attenuated with air to create one or more fibrous elements and/or particles. The fibrous elements and/or particles may then be dried to remove any remaining solvent used for spinning, such as the water.

The fibrous elements and/or particles of the present invention may be collected on a belt, such as a patterned belt to form a fibrous article comprising the fibrous elements and/or particles.

Examples

The following are non-limiting examples of the shampoo compositions described herein. It will be appreciated that other modifications of the present invention within the skill of those in the art can be undertaken without departing from the spirit and scope of this invention.

All parts, percentages, and ratios herein are by weight unless otherwise specified. Some components may come from suppliers as dilute solutions. The amount stated reflects the weight percent of the added material, unless otherwise specified.

The Examples in the tables below, were made as follows. First, a fibrous element-forming composition (melt composition) was prepared by adding water to a container under sufficient stirring, then adding the polyvinyl alcohol polymer(s). The mixture was heated to about 75° C. for about 2-3 hours until a homogeneuous and smooth polymer solution was formed. Then, the surfactant and other active ingredients are added one by one to the smooth polymer solution with mixing until a homogeneous solution was obtained. The homogenous solution is cooled to about 60° C. and any other ingredients, including additional actives, (cationic polymer, citric acid, etc.) were subsequently added. The resulting mixture was stirred until a uniform mixture was obtained. The mixture is then allowed to degas, and the resulting viscous smooth mixture is used to form the fibrous elements and articles according to the Method for Making Fibrous Elements and Articles described herein.

All examples in Table 1, below, are based on a dry basis weight, the fibrous articles absorb water based on the humidity in which they are stored. The diffusion coefficient and lather, in Table 1, below, were determined in the Methods, described hereafter. The lamellar peaks and lamellar harmonic peaks were determined using the Lamella Structure Test Method, described hereafter.

TABLE 1

| Fibrous article Examples A-B and Comparative Examples A-B | | | | |
|---|---|---|---|---|
| | Ex. A | Ex. B | Comp. Ex. A | Comp. Ex. B |
| Polyvinyl alcohol[1] | 33.6 | 34.0 | 30.0 | 31.46 |
| Disodium cocoyl Glutamate[2] | 43.3 | 42.6 | — | — |
| Lauramidopropyl Betaine (LAPB)[4] | 6.9 | 6.8 | — | 9.67 |
| Sodium cocoyl isethionate[5] | 11.5 | 11.3 | — | — |
| Sodium Laureth 1 sulfate[7] | — | — | 27.8 | — |
| Sodium laureth 3 sulfate[8] | — | — | 3.8 | — |
| Sodium undecyl sulfate[9] | — | — | 17.1 | — |
| Lauryl hydroxysultaine[10] | — | — | 17.9 | — |
| Alcohols, C10-16[23] | — | — | — | 56.55 |
| Ethylenediaminetetraacetic acid (EDTA)[11] | 0.46 | 0.50 | 0.40 | — |
| Citric acid[12] | 3.60 | 3.60 | 1.7 | 0.99 |
| Polyquaternium-6[13] | 0.60 | 0.60 | — | — |
| Polyquaternium-10[14] | — | 0.60 | — | — |
| Polyquaternium-10[15] | — | — | — | 0.99 |

TABLE 1-continued

Fibrous article Examples A-B and Comparative Examples A-B

|  | Ex. A | Ex. B | Comp. Ex. A | Comp. Ex. B |
|---|---|---|---|---|
| Polyquaternium-76[16] | — | — | 0.22 | — |
| Guar Hydroxypropyltrimonium Chloride | — | — | 1.18 | — |
| Sodium benzoate[22] | — | — | — | 0.34 |
| Lamellar peak present | No | No | Yes | Yes |
| Lamellar harmonic peaks | No harmonic peaks | No harmonic peaks | 43A, 21.5A, 14.5A | 32A, 16A, 10.5A |
| Diffusion coefficient | 2.04E−12 | 1.56E−12 | 5.57E−13 | 4.53E−12 |
| % improvement in diffusion coefficient | 366% | 280% | reference | 813% |
| Lather (SD = 1.4) | 5.83 | 5.59 | 6.06 | <1 |

Figure 10:
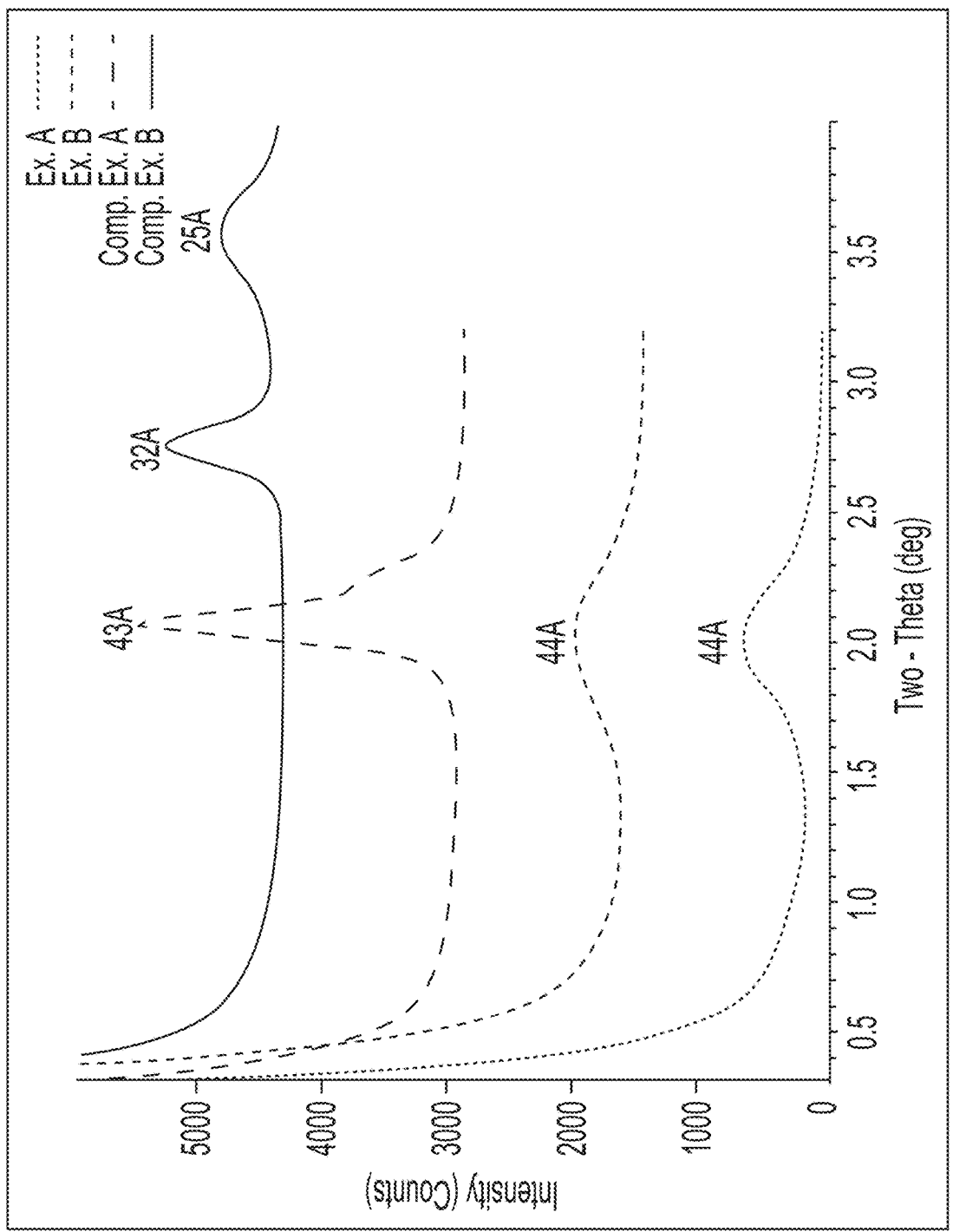
FIG. 10 is a chart showing the SAXS (small-angle X-ray scattering) for Examples A-B and Comparative Examples A-B.
Figure 11:
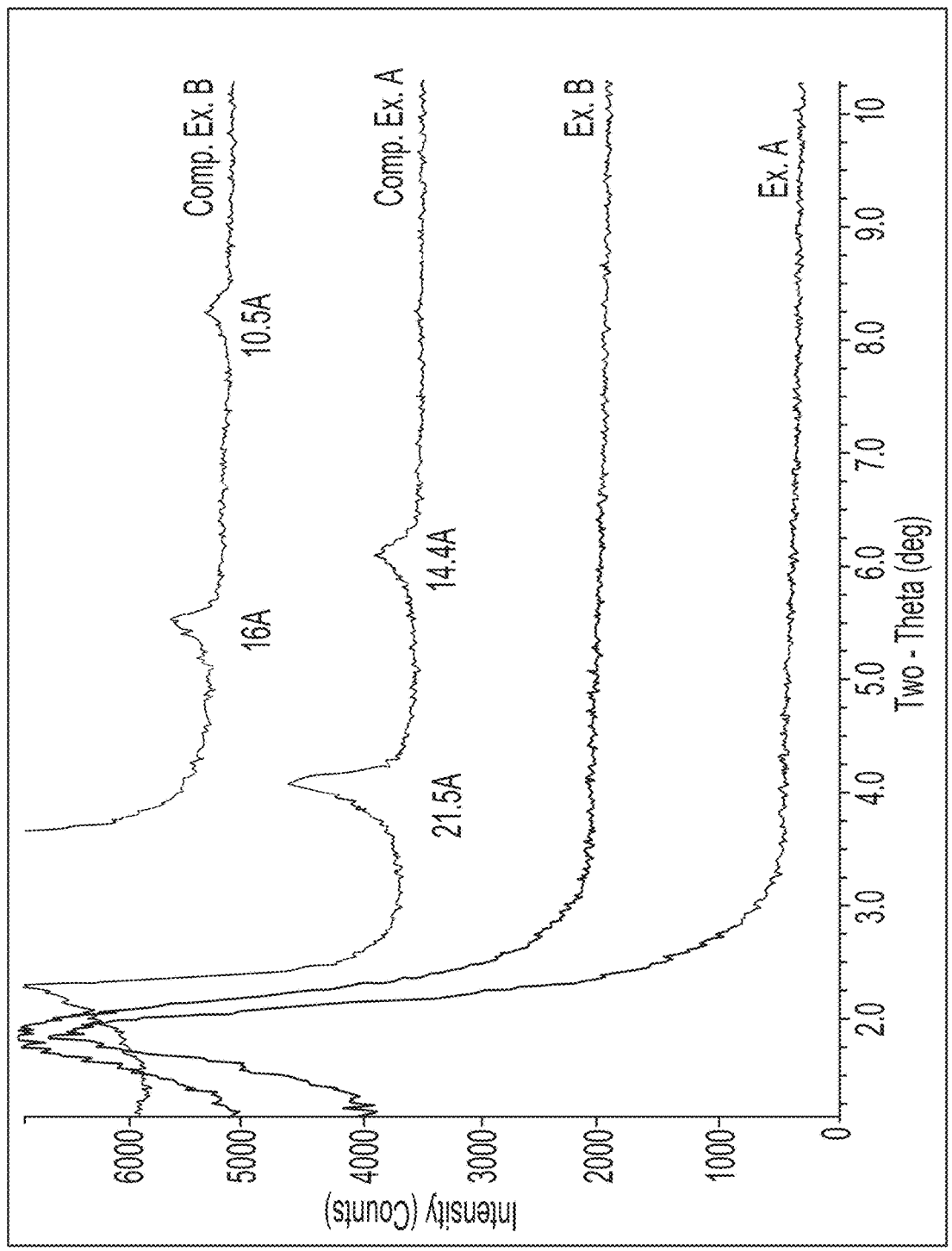
FIG. 11 is a chart showing the WAXS (wide-angle X-ray scattering) for Examples A-B and Comparative Examples A-B.

FIG. 10 is a chart showing the SAXS pattern for Examples A-B and Comparative Examples A-B and FIG. 11 is a chart showing the WAXS pattern for Examples A-B and Comparative Examples A-B. FIG. 10 shows whether there is a lamellar peak and FIG. 11 shows the lamellar harmonic peaks.

The fibrous article in Comparative Example A had a consumer acceptable level of lather. However, some consumers complain that the fibrous article does not always turn into a smooth cream after adding water in the shower and large chunks can still be felt in between hands. The chunks do not become smooth, even after vigorous rubbing between hands. In some instances, if the composition is applied to hair, even after rinsing chunks of the article can remain on the hair.

The fibrous article in Comparative Example B may dissolve very quickly, based on the diffusion coefficient, however the lather is poor and therefore this example would not be consumer preferred. Consumers like lather, since they perceive it as an indication that the shampoo is cleaning their hair.

The fibrous articles in Examples A-B both lack a lamellar peak and lamellar harmonic peaks as determined by the Lamellar Structure Test Method and shown in FIGS. 10-11. Therefore, Examples A-B lack a lamellar structure. The lack of lamellar structure can allow the article to quickly hydrate and dissolve into a smooth liquid shampoo composition without chunks, that is dispersible throughout a user's hair and rinses out of a user's hair without leaving chunks of shampoo behind. Examples A-B may also dissolve faster than Comparative Example A, while still having a similar amount of lather.

The dissolution (# of strokes), in Table 2, below, was determined using the Hand Dissolution Method, described hereafter. The wt. % moisture, in Table 2, below, was determined using the Water Content Method, described hereafter.

TABLE 2

Fibrous article Examples C-D and Comparative Examples C-D

|  | Ex. C | Ex. D | Comp. Ex. C | Comp. Ex. D |
|---|---|---|---|---|
| Polyvinyl alcohol[1] | 28.66 | 29.0 | 34.4 | 25.58 |
| Disodium cocoyl Glutamate[2] | 36.96 | 36.37 | — | — |
| LAPB[4] | 5.90 | 5.81 | 12.31 | — |
| Sodium cocoyl isethionate[5] | 9.83 | 9.65 | — | — |
| Sodium lauroyl Sarcosinate[18] | — | — | 31.77 | — |
| Sorbitol[19] | — | — | 6.16 | — |
| Polyox N60K[20] | — | — | 0.30 | — |
| Sodium laureth 1 sulfate[7] | — | — | — | 23.74 |
| Sodium laureth 3 sulfate[8] | — | — | — | 3.22 |
| Sodium undecyl sulfate[9] | — | — | — | 14.58 |
| Lauryl hydroxysultaine[10] | — | — | — | 15.27 |
| Ethylenediaminetetraacetic acid (EDTA)[11] | 0.39 | 0.43 | — | 0.34 |
| Citric acid[12] | 3.14 | 3.23 | 0.37 | 1.45 |
| Polyquaternium-6[13] | 0.49 | 0.51 | — | — |
| Polyquaternium-10[14] | — | 0.51 | — | — |
| Polyquaternium-76[16] | — | — | — | 0.19 |
| Guar Hydroxypropyltrimonium Chloride | — | — | — | 1.0 |
| Perfume | 6.78 | 6.78 | 6.78 | 6.78 |
| Silicone[21] | 4.74 | 4.74 | 4.74 | 4.74 |
| Moisture | 3.1 | 3.1 | 3.1 | 3.1 |
| Dissolution (# of strokes) | 6 +/− 3 | 6 +/− 3 | >30 | 12 +/− 3 |

The Fibrous articles in Examples C and D have a surfactant system that is substantially free of sulfate-based surfactants. The primary surfactant in Examples C and D is disodium cocoyl glutamate and the co-surfactants include sodium cocoyl isethionate and LAPB. The dissolution (# of strokes) for Examples C and D are 6+/−3, which is on average faster than Comparative Example D, which contains sulfate-based surfactants (e.g. sodium laureth 1 sulfate, sodium laureth 3 sulfate, and sodium undecyl sulfate). Interestingly, Comparative Example C also has a surfactant system that is substantially free of sulfate-based surfactants. The primary surfactant in Comparative Example C is sodium lauroyl sarcosinate and the co-surfactant is LAPB. Comparative Example C took more than 30 strokes to dissolve, which is too long to be consumer acceptable. In some examples, the fibrous articles can be free of or substantially free of sodium lauroyl sarcosinate. Alternatively, the primary surfactant can be free of or substantially free of sodium lauroyl sarcosinate.

Phase stability, in Table 3 and Table 4, below, was determined by visual detection of the Melt Composition. The Melt Composition was determined to be phase stable if by visual detection there is no phase separation, which includes precipitates, and the example appears homogeneous. As used herein, "visual detection" means that a human viewer can visually discern the quality of the example with the unaided eye (excepting standard corrective lenses adapted to compensate for near-sightedness, farsightedness, or astigmatism, or other corrected vision) in lighting at least equal to the illumination of a standard 100-watt incandescent white light bulb at a distance of approximately 1 foot (0.30 m).

Fiber spinnability, in Table 3 and Table 4, below, was determined by spinning the melt composition, according to the Method for Making Fibrous Elements and Articles described herein. If when spun the melt composition had the proper extensional rheology so it could extend to form filaments without breaking or retracting, then the melt was spinnable (see current invention spin ability criteria described in methods of making fibrous articles) described in forming section. If when spun, filaments are not formed, the melt is not spinnable. If the melt composition was stable and spinnable you can form filaments according to the method described herein.

TABLE 3

Inventive Melt Compositions Examples 1-6

| | Ex. 1 | Ex. 2 | Ex. 3 | Ex.4 | Ex. 5 | Ex. 6 |
|---|---|---|---|---|---|---|
| Polyvinyl alcohol[1] | 11.7 | 11.7 | 11.7 | 11.7 | 12.0 | 12.0 |
| Disodium cocoyl Glutamate[2] | 31.11 (50% solids) | 31.11 (50% solids) | 31.11 (50% solids) | 31.11 (50% solids) | — | — |
| Disodium cocoyl Glutamate[3] | — | — | — | — | 24.58 (30% solids) | — |
| Disodium laureth sulfosuccinate | — | — | — | — | — | 24.57 (29.3% solids) |
| Sodium cocoyl isethionate[5] | 4.0 | 4.0 | 4.0 | 4.0 | 3.2 | 3.6 |
| LAPB[5] | 6.86 (35% solids) | 6.86 (35% solids) | 6.86 (35% solids) | 6.86 (35% solids) | 12.4 (35% solids) | 20.57 (35% solids) |
| Decyl glucoside[6] | — | — | — | — | 6.3 (50% solids) | — |
| EDTA[11] | 0.16 | 0.16 | 0.16 | 0.16 | 0.16 | 0.16 |
| Citric acid[12] | 1.28 | 1.28 | 1.28 | 1.28 | 0.68 | 0.50 |
| Polyquaternium-6[13] | 0.50 (40% solids) | — | 0.50 (40% solids) | 0.50 (40% solids) | 0.50 (40% solids) | 0.50 (40% solids) |
| Polyquaternium-10[14] | — | 0.20 | 0.20 | — | 0.20 | 0.20 |
| Guar hydroxypropyltrimonium chloride[17] | — | — | — | 0.2 | — | — |
| Water | Q.S. | Q.S. | Q.S. | Q.S. | Q.S. | Q.S. |
| % solids | 35.3 | 35.3 | 35.5 | 35.5 | 31.3 | 31.1 |
| pH | 5.9 | 5.9 | 6.0 | 6.0 | 6.0 | 6.0 |
| Phase stability | Stable | Stable | Stable | Stable | Stable | Stable |
| Fiber spinnability | Easy to spin | Easy to spin | Easy to spin | Easy to spin | Easy to spin | Easy to spin |

TABLE 4

Melt Compositions Comparative Examples 1-5

| | Comp. Ex. 1 | Comp. Ex. 2 | Comp. Ex. 3 | Comp. Ex. 4 | Comp. Ex.5 |
|---|---|---|---|---|---|
| Polyvinyl alcohol[1] | 14.0 | 14.0 | 12.3 | 12.3 | 11.7 |
| Disodium cocoyl Glutamate[2] | — | — | — | — | 31.11 (50% solids) |
| Sodium cocoyl isethionate[5] | 4.0 | — | — | — | 4.0 |
| LAPB[4] | 6.86 (35% solids) | 10.86 (35% solids) | — | — | 6.86 (35% solids) |
| Sodium lauroyl Sarcosinate[18] | 36.9 (35% solids) | 36.9 (35% solids) | — | — | — |
| Sodium Laureth 1 sulfate[7] | — | — | 16.12 | 16.12 | — |
| Sodium laureth 3 sulfate[8] | — | — | 5.47 | 5.47 | — |
| Sodium undecyl sulfate[9] | — | — | 9.90 | 9.90 | — |
| Lauryl hydroxysultaine[10] | — | — | 14.52 | 14.52 | — |
| EDTA[11] | 0.16 | 0.16 | 0.16 | 0.16 | 0.16 |
| Citric acid[12] | 0.2 | 0.2 | 0.69 | 0.69 | 1.73 |
| Polyquaternium-6[13] | 0.50 | 0.50 | 0.5 | 0.5 | 0.5 |
| Polyquaternium-10[14] | — | — | — | 0.20 | — |
| Water | Q.S. | Q.S. | Q.S. | Q.S. | Q.S. |
| Total | 100.00 | 100.00 | 100.00 | 100.00 | 100.00 |
| pH | 6.0 | 6.0 | 4.5 | 4.5 | 5.4 |
| Phase stability | Not stable | Not stable | Not stable | Not stable | Not stable |
| Fiber spinnability | Not spinnable | Not spinnable | Not spinnable | Not spinnable | Not spinnable |

Examples 1-6 contain a surfactant system that is compatible with cationic polymers that have a relatively high molecular weight and a relatively high charge density. The surfactant systems for Examples 1-6 are substantially free of sulfate-based surfactants. Examples 1-5 contain disodium cocoyl glutamate as the primary surfactant and sodium cocoyl isethionate and LAPB as the co-surfactants. Example 5 contains a surfactant system with disodium laureth sulfosuccinate, sodium cocoyl isethionate and LAPB. Examples 1-5 contain polyquaternium-6 and/or polyquaternium-10 and/or guar hydroxypropyltrimonium chloride. Polyquaternium-6, polyquaternium-10 and guar hydroxypropyltrimonium chloride are examples of relatively high molecular weight polymers with relatively high charge densities can help provide a wet conditioning benefit. It is hypothesized that other relatively high molecular weight, relatively high charge density cationic polymers including cationic guars could also be phase stable and spinnable in the melt compositions. Examples 1-6 are spinnable because they are phase stable, have the proper rheology, and have the proper extensional rheology so the melt can extend to form filaments without breaking or retracting.

Comparative Examples 1-5 are not phase stable and they are not spinnable. In these examples, the surfactant systems are not compatible with the cationic polymers. Comparative Examples 1-2 have a surfactant system that is substantially free of sulfate-based surfactants, containing sodium lauroyl sarcosinate as the primary surfactant. The fibrous articles can be substantially free of sodium lauroyl sarcosinate, alternatively if sodium lauroyl sarcosinate is present it may not be the primary surfactant in the surfactant system. Comparative Examples 3 and 4 contains sulfate-based surfactants. Comparative Example 5 contains sulfate free surfactants with a low pH of about 5.4. This composition is inhomogeneous and does not have the right rheology to spin fibers.

Suppliers for raw materials for the Examples in Tables 1-4.
1. Poval 32-80, Poval 3-80 (50:50 blend) from Kuraray®
2. Eversoft™ UCS-50SG from Sino-Lion
3. Hostapon® CGN from Clariant™
4. Mackam® DAB ULS from Solvay®
5. Jordapon® CI Prill from BASF®
6. Decyl glucoside from BASF®
7. SLE1S (70%): Tianjin Tianzhi Fine Chemical
8. SLE3S (28%): P&G Chemicals
9. Sodium undecyl sulfate (70%): P&G Chemicals
10. Mackam® LHS from Solvay®
11. Versene™ 220 from Dow®
12. Citric acid from ADM™
13. Polyquaternium-6, PolyDADMAC, MW of 150,000, CD of 6.2, trade name: Mirapol® 100s, 31.5% active, 40% solids from Solvay®
14. Polyquaternium-10, UCARE™ Polymer JR-30M from Amerchol®, MW of 2,000,000, CD of 1.25
15. Polyquaternium-10, Poly. LR400 from Amerchol® MW 400,000, CD 0.7
16. Polyquat-76: Mirapol® AT 1 from Rhodia® MW 1,100,000, CD 1.6
17. Jaguar® C500, MW of 500,000, CD of 0.7, from Solvay®
18. Crodasinic™ LS35-LQ-(RB) from Croda
19. Sobitol from ADM™
20. Polyox™ N60K, polyethylene oxide from Dow®
21. Y-14945, amodimethicone, from Momentive®
22. Sodium benzoate from Kalama® Chemical
23. IsalChem123 AS: alkyl sulfate from P&G Chemicals Test Methods Unless otherwise specified, all tests described herein including those described under the Definitions section and the following test methods are conducted on samples that have been conditioned in a conditioned room at a temperature of 22° C.±2° C. and a relative humidity of 42%±4% for a minimum of 2 hours prior to the test. The samples tested are "usable units." "Usable units" as used herein means sheets, flats from roll stock, pre-converted flats, and/or single or multi-ply products. All tests are conducted under the same environmental conditions and in such conditioned room. Do not test samples that have defects such as wrinkles, tears, holes, and like. Samples conditioned as described herein are considered dry samples (such as "dry filaments") for testing purposes. All instruments are calibrated according to manufacturer's specifications.

Basis Weight Test Method

Basis weight of a fibrous article is measured on stacks of twelve usable units using a top loading analytical balance with a resolution of ±0.001 g. The balance is protected from air drafts and other disturbances using a draft shield. A precision cutting die, measuring 3.500 in ±0.0035 in by 3.500 in ±0.0035 in is used to prepare all samples.

With a precision cutting die, cut the samples into squares. Combine the cut squares to form a stack twelve samples thick. Measure the mass of the sample stack and record the result to the nearest 0.001 g.

The Basis Weight is calculated in lbs/3000 ft$^2$ or g/m$^2$ as follows:

Basis Weight=(Mass of stack)/[(Area of 1 square in stack)×(No. of squares in stack)]

For example,

Basis Weight (lbs/3000 ft$^2$)=[[Mass of stack (g)/ 453.6 (g/lbs)]/[12.25 (in$^2$)/144 (in$^2$/ft$^2$)×12]]× 3000 or,

Basis Weight (g/m$^2$)=Mass of stack (g)/[79.032 (cm$^2$)/10,000 (cm$^2$/m$^2$)×12]

Report result to the nearest 0.1 lbs/3000 ft$^2$ or 0.1 g/m$^2$. Sample dimensions can be changed or varied using a similar precision cutter as mentioned above, so as at least 100 square inches of sample area in stack.

Charge Density Test Method

If one has identified or knows the soil adsorbing agent in and/or on an article of manufacture, then the charge density of the soil adsorbing agent can be determined by using a Mutek PCD-04 Particle Charge Detector available from BTG, or equivalent instrument. The following guidelines provided by BTG are used. Clearly, manufacturers of articles of manufacture comprising soil adsorbing agents know what soil adsorbing agent(s) are being included in their articles of manufacture. Therefore, such manufacturers and/or suppliers of the soil adsorbing agents used in the articles of manufacture can determine the charge density of the soil adsorbing agent.

1. Start with a 0.1% solution (0.1 g soil adsorbing agent+99.9 g deionized water). Preparation of dilute aqueous solutions in deionized water from inverse or dewatered inverse emulsions are performed as instructed by the supplier of the emulsions and is well known to one of ordinary skill in the art. Depending on the titrant consumption increase or decrease soil adsorbing agent content. Solution pH is adjusted prior to final dilution as charge density of many additives is dependent upon solution pH. A pH of 4.5 is used here for cationic polymers and between 6-7 for anionic polymers. No pH adjustment was necessary for the anionic polymers included in this study.

2. Place 20 grams of sample in the PCD measuring cell and insert piston.

3. Put the measuring cell with piston and sample in the PCD, the electrodes are facing the rear. Slide the cell along the guide until it touches the rear.

4. Pull piston upwards and turn it counter-clock-wise to lock the piston in place.

5. Switch on the motor. The streaming potential is shown on the touch panel. Wait 2 minutes until the signal is stable.

6. Use an oppositely charged titrant (for example for a cationic sample having a positive streaming potential: use an anionic titrant). Titrants are available from BTG consisting of 0.001N PVSK or 0.001N PolyDADMAC.

7. An automatic titrator available from BTG is utilized. After selecting the proper titrant, set the titrator to rinse the tubing by dispensing 10 mL insuring that all air bubbles have been purged.

8. Place tubing tip below the surface of the sample and start titration. The automatic titrator is set to stop automatically when the potential reaches 0 mV.

9. Record consumption of titrant, ideally, the consumption of titrant should be 0.2 mL to 10 mL; otherwise decrease or increase soil adsorbing agent content.

10. Repeat titration of a second 20 grams aliquot of the soil adsorbing agent sample.

11. Calculate charge density (charge demand) of the material.

$$\text{Charge Density} = \text{Charge Demand}\left(\frac{\text{meq}}{\text{g}}\right)$$

$$= \frac{V \text{ titrant used (mL)} \times \text{Conc. of titrant in NOrmality}\left(\frac{\text{meq}}{\text{mL}}\right)}{\text{Wt. soil absorbing agent in measured sample}}$$

The charge density (charge demand) of a soil adsorbing agent is reported in meq/g units.

Diameter Test Method

The diameter of a discrete fibrous element or a fibrous element within a fibrous article is determined by using a Scanning Electron Microscope (SEM) or an Optical Microscope and an image analysis software. A magnification of 200 to 10,000 times is chosen such that the fibrous elements are suitably enlarged for measurement. When using the SEM, the samples are sputtered with gold or a palladium compound to avoid electric charging and vibrations of the fibrous element in the electron beam. A manual procedure for determining the fibrous element diameters is used from the image (on monitor screen) taken with the SEM or the optical microscope. Using a mouse and a cursor tool, the edge of a randomly selected fibrous element is sought and then measured across its width (i.e., perpendicular to fibrous element direction at that point) to the other edge of the fibrous element. A scaled and calibrated image analysis tool provides the scaling to get actual reading in µm. For fibrous elements within a fibrous article, several fibrous elements are randomly selected across the sample of the fibrous article using the SEM or the optical microscope. At least two portions of the fibrous article are cut and tested in this manner Altogether at least 100 such measurements are made and then all data are recorded for statistical analysis. The recorded data are used to calculate average (mean) of the fibrous element diameters, standard deviation of the fibrous element diameters, and median of the fibrous element diameters.

Another useful statistic is the calculation of the amount of the population of fibrous elements that is below a certain upper limit. To determine this statistic, the software is programmed to count how many results of the fibrous element diameters are below an upper limit and that count (divided by total number of data and multiplied by 100%) is reported in percent as percent below the upper limit, such as percent below 1 micrometer diameter or %-submicron, for example. We denote the measured diameter (in µm) of an individual circular fibrous element as di.

In the case that the fibrous elements have non-circular cross-sections, the measurement of the fibrous element diameter is determined as and set equal to the hydraulic diameter which is four times the cross-sectional area of the fibrous element divided by the perimeter of the cross-section of the fibrous element (outer perimeter in case of hollow fibrous elements). The number-average diameter, alternatively average diameter is calculated as:

$$d_{num} = \frac{\sum_{i=1}^{n} d_i}{n}$$

Diffusion Coefficient Measurement

Spectrometer: Bruker Avance™ 700 MHz

Probe: Bruker Diff30 high power diffusion probe equipped with Z axis gradients

Amplifier: GREAT 40 A

Pulse sequence: ledbpgp2s

Gradient pulse durations (p30) were set to 3500 us, with big delta periods (d20) set at 200 ms. Thirty-two linearly-spaced gradient values were used ranging from 2%-98% of the amplifier capacity.

Sample prep consisted of weighing approximately 0.5 g of webbing and 2.5 g of D20 into a scintillation vial. The webbing was kept at ambient conditions prior to weighing. The samples were then vortexed until uniform and pipetted into standard borosilicate 5 mm NMR tubes. Data acquisition was performed at 25° C.

Data were processed using vendor supplied software (Topspin version 2.1) utilizing single exponential decay fitting. Three peaks in the proton spectrum were averaged to obtain the reported average diffusion coefficient.

Fibrous Element Composition Test Method

In order to prepare fibrous elements for fibrous element composition measurement, the fibrous elements must be conditioned by removing any coating compositions and/or materials present on the external surfaces of the fibrous elements that are removable. An example of a method for doing so is washing the fibrous elements 3 times with a suitable solvent that will remove the external coating while leaving the fibrous elements unaltered. The fibrous elements are then air dried at 23° C.±1.0° C. until the fibrous elements comprise less than 10% moisture. A chemical analysis of the conditioned fibrous elements is then completed to determine the compositional make-up of the fibrous elements with respect to the filament-forming materials and the active agents and the level of the filament-forming materials and active agents present in the fibrous elements.

The compositional make-up of the fibrous elements with respect to the filament-forming material and the active agents can also be determined by completing a cross-section analysis using TOF-SIMs or SEM. Still another method for determining compositional make-up of the fibrous elements uses a fluorescent dye as a marker. In addition, as always, a manufacturer of fibrous elements should know the compositions of their fibrous elements.

Hand Dissolution Method

Materials Needed:

Fibrous articles to be tested: 3-5 fibrous articles (finished product samples) are tested so that an average of the number of strokes for each if the individual fibrous article samples is calculated and recorded as the Average Hand Dissolution value for the fibrous article. For this method, the entire consumer saleable or consumer use fibrous article is tested. If the entire consumer saleable or consumer use fibrous article has a footprint greater than 50 cm$^2$, then first cut the fibrous article to have a footprint of 50 cm$^2$.

Nitrile Gloves 10 cc syringe

Plastic Weigh boat (~3 in×3 in)

100 mL Glass beaker

Water (City of Cincinnati Water or equivalent having the following properties: Total Hardness=155 mg/L as $CaCO_2$; Calcium content=33.2 mg/L; Magnesium content=17.5 mg/L; Phosphate content=0.0462 mg/L). Water used is water 7 grains per gallon (gpg) hardness and 40° C.+/−5° C.

Protocol:

Add 80 mL of water to glass beaker.

Heat water in beaker until water is at a temperature of 40° C.+/−5° C.

Transfer 15 mL of the water from the beaker into the weigh boat via the syringe.

Within 10 seconds of transferring the water to the weigh boat, place fibrous article sample in palm of gloved hand (hand in cupped position in non-dominant hand to hold fibrous article sample).

Using dominant hand, add water quickly from the weigh boat to the fibrous article sample and allow to immediately wet for a period of 5-10 seconds.

Rub with opposite dominant hand (also gloved) in 2 rapid circular strokes.

Visually examine the fibrous article sample in hand after the 2 strokes. If fibrous article sample is completely dissolved, record number of strokes=2 Dissolution Strokes. If not completely dissolved, rub remaining fibrous article sample for 2 more circular strokes (4 total) and observe degree of dissolution. If the fibrous article sample contains no solid pieces after the 2 additional strokes, record number of strokes=4 Dissolution Strokes. If after the 4 strokes total, the fibrous article sample still contains solid pieces of un-dissolved fibrous article sample, continue rubbing remaining fibrous article sample in additional 2 circular strokes and check if there are any remaining solid pieces of fibrous article sample after each additional 2 strokes until fibrous article sample is completely dissolved or until reaching a total of 30 strokes, whichever comes first. Record the total number of strokes. Record 30 Dissolution Strokes even if solid fibrous article sample pieces remain after the maximum of 30 strokes.

Repeat this process for each of the additional 4 fibrous article samples.

Calculate the arithmetic mean of the recorded values of Dissolution Strokes for the 5 individual fibrous article samples and record as the Average Hand Dissolution Value for the fibrous article. The Average Hand Dissolution Value is reported to the nearest single Dissolution Stroke unit.

Lamellar Structure Test Method

The Lamellar Structure Test Method makes use of small-angle x-ray scattering (SAXS) and wide-angle x-ray scattering (WAXS) to determine if a lamellar structure is present in the article either in a conditioned, dry state or upon wetting after having been previously in a conditioned, dry state. The article is conditioned at a temperature of 22° C.±2° C. and a relative humidity of 42%±4% for a minimum of 2 hours prior to the test. The dissolvable articles as described herein are in a conditioned, dry state for the purposes of this invention. All instruments are calibrated according to manufacturer's specifications.

Dry Sample Preparation

To prepare a sample to be analyzed directly in the conditioned, dry state, a specimen of about 1.0 cm diameter disc is isolated from the center of an article and is loaded into a conventional X-Ray solid sample holder with aperture diameter between 4 and 5 mm (Multiple specimen discs may be extracted from multiple articles and stacked, if necessary, to ensure sufficient scattering cross-section.) The loaded sample holder is immediately placed in the appropriate instrument for data collection.

Wet Sample Preparation

Three samples are analyzed upon wetting from the dry, conditioned state. Specimens are extracted from dry, conditioned dissolvable articles and hydrated with water in order to achieve three separate preparations each possessing a different material-to-water mass ratio. The three different material-to-water mass ratios to be prepared are 1:5; 1:9; and 1:20. For each mass ratio, one or more specimens (as needed) 1 cm in diameter are extracted from the geometric centers of one or more articles in the dry, conditioned state are hydrated with 23° C.±2.0° C. filtered deionized (DI) water in order to achieve the intended material-to-water mass ratio. Each of the three material/water mixtures (each corresponding to a different mass ratio) is stirred under low shear gently by hand at room temperature using a spatula until visibly homogenous. Each material/water mixture is then immediately loaded into a separate quartz capillary tube with outer diameter 2.0 mm in diameter and 0.01 mm wall thickness. The capillary tubes are immediately sealed with a sealant such as an epoxy resin to prevent the evaporation of water from the preparations. The sealant is permitted to dry for at least 2 hours and until dry at a temperature of 23° C.±2.0° C. prior to sample analysis. Each prepared wet sample is introduced into an appropriate X-Ray instrument and data are collected.

Testing and Analysis

Samples are tested using SAXS in 2-dimension (2D) transmission mode over an angular range in of 0.3° to 3.0° 2θ, to observe the presence and spacing of any intensity bands in the x-ray scatter pattern. The test is conducted using a SAXS instrument (such as the NanoSTAR, Bruker AXS Inc., Madison, Wis., U.S.A., or equivalent). The micro-focus Cu x-ray tube was operated at 50 kV, 0.60 mA with 550 um ScanTex Pinholes. The sample to detector distance was 107.39 cm and the detector a Vantec2K 2-dimensional area detector. Samples were placed in the solid sample holder and analyzed under atmospheric conditions with an analysis time of 600 s. Sealed liquid samples are analyzed in the instrument under vacuum.

As needed the samples are also tested using WAXS in transmission mode over a range of 0° to 72° 2θ with a step size of 3° 2θ and 15 seconds per step. The test is also conducted using a WAXS instrument (such as the STOE STADI MP, STOE & Cie GmbH, Darmstadt, Germany). The generator is operated at 40 kV/40 mA, powering a copper anode long-fine-focus Cu x-ray tube. The diffractometer incorporates an incident-beam curved germanium-crystal monochromator, standard incident-beam slit system, and Mythen PSD detector.

All samples are analyzed at a temperature of 23° C.±2.0° C. The x-ray tube of the instrument is operated sufficient power to ensure that any scattering bands present are clearly detected. The beam diameter is 550±50 μm. The raw 2-D SAXS scattering pattern is integrated azimuthally to determine intensity (I) as a function of the scattering vector (q), which are expressed throughout this method units of reciprocal angstroms ($Å^{-1}$). The values for q are calculated by the SAXS (or as needed the WAXS) instrument according to the following equation:

$$q = \frac{4\pi}{\lambda}\sin\theta$$

where:
2θ is the scattering angle; and
λ is the wavelength used.

For each integrated SAXS (or WAXS) analyzed, the value of q in $Å^{-1}$ corresponding to each intensity peak on the plot of I vs q is identified and recorded from smallest to largest. (One of skill in the art knows that a sharp peak in q near the origin corresponds to scatter off of the beam stop and is disregarded in this method.) The value of q corresponding to the first intensity peak (the lowest value of q) is referred to as q*.

For a sample analyzed directly in the dry, conditioned state, if an intensity peak is present at $2q^*\pm0.002$ $Å^{-1}$, the sample is determined to exhibit a lamellar structure, and the characteristic d-spacing parameter is defined as $2\pi/q^*$. If no intensity peak if present at $2q^*\pm0.002$ $Å^{-1}$, the sample analyzed directly in the dry, conditioned state is determined to not exhibit a lamellar structure.

For a sample analyzed upon wetting from the dry, conditioned state, if an intensity peak is present at $2q^*\pm0.002$ $Å^{-1}$, the sample is determined to exhibit a lamellar structure, and the characteristic d-spacing parameter is defined as $2\pi/q^*$. If no intensity peak is present at $2q^*\pm0.002$ $Å^{-1}$, the sample is determined to not exhibit a lamellar structure. If a lamellar structure is determined to be present in at least any one of the three material/water ratios prepared, then this material is determined to exhibit a lamellar structure upon wetting. If no intensity peak is present at $2q^*\pm0.002$ $Å^{-1}$, in any of the three material/water ratios prepared, the material is determined to not exhibit a lamellar structure upon wetting.

Lather Method

Expert panelists determined the amount of lather on a qualitative scale of 0 (small amount) to 8 (large amount).

The amount of lather was determined using hair switches at the following test conditions:
Water Temp is set at 100 F+/−2 degrees
Water Pressure 1.5 GPM+/−0.1 GPM
Water hardness: Lab water typically between 8 and 11 grain per gallon hardness An 8-inch (20.32 cm), 20-gram hair switch was wet under running water for 6 seconds (3 seconds on each side following metronome, a metronome is used to ensure unity and keep panelists timing). The wet hair was squeegeed between the thumb and index and middle fingers from top to bottom three times.

With the dominant hand holding the top (bound end) of the hair, the hair was pulled upward while squeezing the switch between the thumb and index finger of the non-dominant hand using 8-10 ounces of pressure. All lather was accumulated into the palm of the non-dominant hand. The switch was then set aside. The amount of lather was rated and recorded.

Thickness Method

Thickness of a fibrous article is measured by cutting 5 samples of a fibrous article sample such that each cut sample is larger in size than a load foot loading surface of a VIR Electronic Thickness Tester Model II available from Thwing-Albert Instrument Company, Philadelphia, Pa. Typically, the load foot loading surface has a circular surface area of about 3.14 $in^2$. The sample is confined between a horizontal flat surface and the load foot loading surface. The load foot loading surface applies a confining pressure to the sample of 15.5 $g/cm^2$. The thickness of each sample is the resulting gap between the flat surface and the load foot loading surface. The thickness is calculated as the average thickness of the five samples. The result is reported in millimeters (mm).

Water Content Test Method

The water (moisture) content present in a fibrous element and/or particle and/or fibrous article is measured using the following Water Content Test Method. A fibrous element and/or particle and/or fibrous article or portion thereof ("sample") in the form of a pre-cut sheet is placed in a conditioned room at a temperature of 22° C.±2° C. and a relative humidity of 42%±4% for at least 24 hours prior to testing. Each fibrous article sample has an area of at least 4 square inches, but small enough in size to fit appropriately on the balance weighing plate. Under the temperature and humidity conditions mentioned above, using a balance with at least four decimal places, the weight of the sample is recorded every five minutes until a change of less than 0.5% of previous weight is detected during a 10-minute period. The final weight is recorded as the "equilibrium weight". Within 10 minutes, the samples are placed into the forced air oven on top of foil for 24 hours at 22° C.±2° C. and a relative humidity of 42%±4% for drying. After the 24 hours of drying, the sample is removed and weighed within 15 seconds. This weight is designated as the "dry weight" of the sample.

The water (moisture) content of the sample is calculated as follows:

$$\% \text{ Water in sample} = 100\% \times \frac{(\text{Equilibrium weight of sample} - \text{Dry weight of sample})}{\text{Dry weight of sample}}$$

The % Water (moisture) in sample for 3 replicates is averaged to give the reported % Water (moisture) in sample. Report results to the nearest 0.1%.

Combinations

A. A dissolvable solid fibrous shampoo article comprising fibrous elements comprising:
   a. from about 1% to about 90%, by weight on a dry article basis, of a polymeric structurant;
   b. from about 10% to about 90%, preferably from about 20% to about 80%, preferably from about 30% to about 70%, more preferably from about 40% to about 65%, by weight on a dry article basis, of a surfactant system; wherein the fibrous article is substantially free of a lamellar structure as determined by the Lamellar Structure Test Method.
B. The article of Paragraph A, wherein the article comprises a hand dissolution value of less than 15 strokes, preferably less than 12 strokes and preferably less than 15 strokes as determined by the Hand Dissolution Test Method.
C. The article of Paragraphs A-B, wherein the article comprises a hand dissolution value of from 1 to about 25 strokes, preferably from about 2 to about 15 strokes, more preferably from about 3 to about 10 strokes.
D. The article of Paragraphs A-C, wherein the article comprises from about 1% to about 50%, preferably from about 10% to about 40%, by weight on a dry article basis, of the polymeric structurant.
E. The article of Paragraphs A-D, wherein the polymeric structurant is selected from the group consisting of carboxymethyl cellulose, starch, polyvinyl alcohol, and combinations thereof.
F. The article of Paragraphs A-E, wherein the polymeric structurant comprises polyvinyl alcohol comprising a weight average molecular weight of from about 10,000 g/mol to about 40,000,000 g/mol, preferably from about 35,000 g/mol to about 20,000,000 g/mol, more preferably from about 40,000 g/mol to about 5,000,000 g/mol, and even more preferably from about 40,000 g/mol to about 500,000 g/mol.
G. The article of Paragraphs A-F, wherein the article comprises from about 10% to about 80%, preferably from about 20% to about 70%, more preferably from about 30% to about 65%, and even more preferably from about 35% to about 60%, by weight on a dry article basis, of the polymeric structurant.
H. The article of Paragraphs A-G, wherein the surfactant system is substantially free of sulfate-based surfactants.
I. The article of Paragraphs A-H, wherein the surfactant system comprises a glutamate surfactant selected from the group consisting of sodium cocoyl glutamate, disodium cocoyl glutamate, potassium cocoyl glutamate, dipotassium cocoyl glutamate, ammonium cocoyl glutamate, diammonium cocoyl glutamate, TEA-cocoyl glutamate, and mixtures thereof.
J. The article of Paragraphs A-I, wherein the surfactant system comprises:
   a. from about 35% to about 90%, preferably from about 40% to about 85%, more preferably from about 45% to about 80%, even more preferably from about 48% to about 76%, by weight of the surfactant system on a dry article basis, of a primary anionic surfactant; and
   b. from about from about 10% to about 65%, preferably from about 15% to about 55%, more preferably from about 23% to about 50%, by weight of the surfactant system on a dry article basis, of a co-surfactant.
K. The article of Paragraphs A-J, wherein the surfactant system is substantially free of sodium lauroyl sarcosinate.
L. The article of Paragraphs A-K, wherein the primary anionic surfactant comprises a glutamate surfactant selected from the group consisting of sodium cocoyl glutamate, disodium cocoyl glutamate, potassium cocoyl glutamate, dipotassium cocoyl glutamate, ammonium cocoyl glutamate, diammonium cocoyl glutamate, TEA-cocoyl glutamate, and mixtures thereof.
M. The article of Paragraphs A-L, wherein the primary anionic surfactant is selected from the group consisting of disodium cocoyl glutamate, disodium laureth sulfosuccinate, and combinations thereof.
N. The article of Paragraphs A-M, wherein the primary anionic surfactant is a surfactant comprising two negatively charged hydrophilic groups.
O. The article of Paragraphs A-N, wherein the primary anionic surfactant is not sodium lauroyl sarcosinate.
P. The article of Paragraphs A-O, wherein the co-surfactant is selected from the group consisting of lauramidopropyl betaine, sodium cocoyl isethionate, and combinations thereof.
Q. The article of Paragraphs A-P, wherein the surfactant is selected from the group consisting of disodium cocoyl glutamate, disodium laureth sulfosuccinate, disodium cocoamphodiacetate, disodium lauroamphodiacetate, sodium cocoyl alaninate, and combinations thereof.
R. The article of Paragraphs A-Q, wherein the fibrous elements are homogeneous.
S. The article of Paragraphs A-R, wherein the fibrous article is free of the lamellar structure as determined by the Lamellar Structure Test Method.
T. The article of Paragraphs A-S, further comprising from about 0.05% to about 5%, preferably from about 0.1% to about 2% cationic polymer, more preferably from about 0.2% to about 1.5% cationic polymer, even more preferably from about 0.3% to about 1.0% cationic polymer, on a dry article basis, of a cationic polymer.
U. The article of Paragraph T, wherein the cationic polymer comprises a weight average molecular weight of greater than 500,000 g/mol, preferably greater than 1 million g/mol as measured by gel permeation chromatography.
V. The article of Paragraph T, wherein the cationic polymer comprises a weight average molecular weight of from about 500,000 g/mol to about 2.5 million g/mol, preferably from about 500,000 g/mol to about 2 million g/mol, more preferably from about 500,000 g/mol to about 1.5 million g/mol, and even more preferably from about 500,000 g/mol to about 1 million as measured by gel permeation chromatography.
W. The article of Paragraphs T-V, wherein the cationic polymer comprises a weight average charge density of greater than 0.4 meg/g, preferably greater than about 1.0 meg/g, more preferably greater than about 2 meg/g, as measured according to the Charge Density Test Method.
X. The article of Paragraphs T-V, wherein the cationic polymer comprises a weight average charge density of from about 0.4 meg/g to about 5 meg/g, alternatively from about 1 meg/g to about 3 meg/g, alternatively from about 1 meg/g to about 2.5 meg/g as measured according to the Charge Density Test Method.
Y. The article of Paragraphs A-X, wherein the cationic polymer is selected from the group consisting of Polyquaternium-6, Polyquaternum-10, and combinations thereof.
Z. The article of Paragraphs A-Y, further comprising from about 0.001% to about 10%, by weight on a dry element basis, of an extensional aid comprising a weight average molecular weight from about 500,000 Da to about 25,000,000 Da, preferably from about 800,000 Da to about 22,000,000 Da, more preferably from about 1,000,000 Da to about 20,000,000 Da, and even more preferably from about 2,000,000 Da to about 15,000,000 Da.

AA. The article of Paragraph Z, wherein the extensional aid is selected from the group consisting of polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide BB. The article of Paragraphs A-AA, wherein the article has a diffusion coefficient of greater than 5.5e-13, preferably greater than 7e-13, more preferably greater than 1e-12, even more preferably greater than 2e-12 according to the Diffusion Coefficient Measurement Test Method.

CC. The article of Paragraphs A-BB, wherein the article has a diffusion coefficient of from about 5.5e-13 to about 1e-11, preferably from about 5.3e-13 to about 6e-12, more preferably from about 1e-12 to about 5e-12, even more preferably from about 1.3e-12 to about 4.5e-12.

DD. The article of Paragraphs A-CC, wherein the article comprises a lather score of greater than 2, preferably greater than 3, more preferably greater than 4, and even more preferably greater than 5, according to the Lather Method.

EE. A method of making the article of Paragraphs A-DD, comprising the steps of:
  a. providing a filament-forming composition comprising the polymeric structurant and the surfactant system, wherein the filament forming composition comprises a pH of greater than about 5.5;
  b. spinning the filament-forming composition into one or more filaments, wherein the filament-forming composition is spinnable;
  c. drying the filaments at a temperature from about 340° F. (171.1° C.) to about 350° F. (176.7° C.) for about 50 to about 60 seconds or from about 390° F. (198.9° C.) to about 400° F. (204° C.) for about 30 to about 40 seconds or 415° F. (212.8° C.) to 470° F. (243.3° C.) for about 5 to about 20 seconds;
  d. forming the article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dissolvable solid fibrous shampoo article comprising fibrous elements comprising:
  a. from about 1% to about 50%, by weight on a dry article basis of a polymeric structurant;
  b. from about 10% to about 90%, by weight on a dry article basis, of a surfactant system comprising a primary anionic surfactant and one or more co-surfactants; wherein the primary anionic surfactant comprises a glutamate surfactant; wherein the surfactant system is free of sulfate-based surfactants; and
  c. optionally a cationic polymer comprising a weight average molecular weight from about 100,000 g/mol to about 2.5 million g/mol as measured by gel permeation chromatography and a charge density of greater than 0.5 meg/g as measured according to the Charge Density Test Method;
  wherein the fibrous article is substantially free of a lamellar structure as determined by the Lamellar Structure Test Method in a conditioned, dry state;
  wherein the fibrous article comprises a hand dissolution of less than 15 strokes according to the Hand Dissolution Test Method;
  wherein the fibrous elements comprise filaments;
  wherein the plurality of fibrous elements are interentangled or otherwise associated with one another to form the fibrous structure.

2. The article of claim 1 wherein the polymeric structurant is selected from the group consisting of carboxymethyl cellulose, starch, polyvinyl alcohol, and combinations thereof.

3. The article of claim 1 wherein each fibrous element is homogeneous.

4. The article of claim 1, wherein the fibrous article is free of the lamellar structure as determined by the Lamellar Structure Test Method in a conditioned, dry state.

5. The article of claim 1, wherein the glutamate surfactant is selected from the group consisting of disodium cocoyl glutamate, dipotassium cocoyl glutamate, diammonium cocoyl glutamate, and mixtures thereof.

6. The article of claim 1, wherein the article comprises a lather score of greater than 4 according to the Lather Method.

7. The article of claim 1, wherein the one or more co-surfactants comprises lauramidopropyl betaine, sodium cocoyl isethionate, lauryl hydroxysultaine, cocoamidopropyl betaine, or a combination thereof.

8. A dissolvable solid fibrous shampoo article comprising fibrous elements comprising:
  a. from about 1% to about 50%, by weight on a dry article basis, polymeric structurant; and
  b. from about 20% to about 70%, by weight on a dry article basis, of a surfactant system comprising:
    i. from about 35% to about 90%, by weight of the surfactant system on a dry article basis, of a primary anionic surfactant comprising a glutamate surfactant; and
    ii. from about from about 10% to about 65%, by weight of the surfactant system on a dry article basis, of a co-surfactant comprising sodium cocoyl isethionate and lauramidopropyl betaine;
  wherein the fibrous article is substantially free of a lamellar structure as determined by the Lamellar Structure Test Method in a conditioned, dry state;

wherein the fibrous article comprises a hand dissolution of less than 15 strokes;
wherein the fibrous elements comprise filaments;
wherein the plurality of fibrous elements are inter-entangled or otherwise associated with one another to form the fibrous structure.

9. The article of claim 8, wherein the glutamate surfactant comprises disodium cocoyl glutamate.

10. The article of claim 8, wherein the surfactant system is substantially free of sodium lauroyl sarcosinate.

11. The article of claim 8, further comprising from about 0.1% to about 2%, on a dry article basis, of a cationic polymer comprising a weight average molecular weight from about 100,000 g/mol to about 2.5 million g/mol as measured by gel permeation chromatography and a charge density of greater than 0.5 meg/g as measured according to the Charge Density Test Method.

12. The article of claim 11, wherein the cationic polymer is selected from the group consisting of Polyquaternium-6, Polyquaternium-10, cationic guars, and combinations thereof.

13. The article of claim 8, wherein the article comprises a lather score of greater than 4 according to the Lather Method in a conditioned, dry state.

14. The article of claim 8, wherein the fibrous article comprises a hand dissolution of less than 15 strokes according to the Hand Dissolution Test Method.

15. A method of making the article of claim 8 comprising the steps of:
  a. providing a filament-forming composition comprising the polymeric structurant and the surfactant system, wherein the filament forming composition comprises a pH of greater than about 5.5;
  b. spinning the filament-forming composition into one or more filaments, wherein the filament-forming composition is spinnable;
  c. drying the filaments at a temperature from about 340° F. (171.1° C.) to about 350° F. (176.7° C.) for about 50 to about 60 seconds or from about 390° F. (198.9° C.) to about 400° F. (204° C.) for about 30 to about 40 seconds or 415° F. (212.8° C.) to 470° F. (243.3° C.) for about 5 to about 20 seconds;
  d. forming the article.

16. A dissolvable solid fibrous shampoo article comprising fibrous elements comprising:
  a. from about 10% to about 40%, on a dry article basis, of a polyvinyl alcohol;
  b. from about 20% to about 80%, on a dry article basis, of a surfactant system comprising:
    i. from about 45% to about 80%, by weight of the surfactant system on a dry article basis, of a primary anionic surfactant selected from the group consisting of disodium cocoyl glutamate, disodium laureth sulfosuccinate, and combinations thereof;
    ii. from about 20% to about 55%, by weight of the surfactant system on a dry article basis, of a co-surfactant selected from the group consisting of lauramidopropyl betaine, sodium cocoyl isethionate, lauryl hydroxysultaine, cocoamidopropyl betaine, decyl glucoside, and combinations thereof; and
  c. from about 0.1% to about 2%, on a dry article basis, of a cationic polymer;
  wherein the cationic polymer is selected from the group consisting of Polyquaternium-6, Polyquaternium-10, cationic guar comprising a weight average molecular weight from about 500,000 g/mol to about 2.5 million g/mol as measured by gel permeation chromatography and a charge density of greater than 0.5 meg/g, and combinations thereof;
  wherein the fibrous elements comprise filaments;
  wherein the plurality of fibrous elements are inter-entangled or otherwise associated with one another to form the fibrous structure.

17. The article of claim 16, wherein the fibrous article is substantially free of a lamellar structure as determined by the Lamellar Structure Test Method in a conditioned, dry state.

18. The article of claim 16, wherein the fibrous article comprises a hand dissolution of less than 15 strokes according to the Hand Dissolution Test Method.

19. The article of claim 16, wherein the fibrous article comprises a diffusion coefficient of from about 5.5e-13 to about 1e-11.

* * * * *